US008440797B2

(12) United States Patent
Watanabe et al.

(10) Patent No.: US 8,440,797 B2
(45) Date of Patent: May 14, 2013

(54) HUMAN MONOCLONAL ANTIBODY

(75) Inventors: Takamasa Watanabe, Osaka (JP); Tadahiko Yoshima, Osaka (JP); Mikael Mattsson, Loddekopinge (SE); Anna Sarnefalt, Malmo (SE); Takuya Hasezaki, Osaka (JP)

(73) Assignee: Dainippon Sumitomo Pharma Co., Ltd., Osaka-shi (JP)

( * ) Notice: Subject to any disclaimer, the term of this patent is extended or adjusted under 35 U.S.C. 154(b) by 0 days.

(21) Appl. No.: 13/311,124

(22) Filed: Dec. 5, 2011

(65) Prior Publication Data

US 2012/0141486 A1 Jun. 7, 2012

Related U.S. Application Data

(60) Provisional application No. 61/420,136, filed on Dec. 6, 2010.

(51) Int. Cl.
*C07K 16/00* (2006.01)

(52) U.S. Cl.
USPC .......... 530/387.1

(58) Field of Classification Search .......... None
See application file for complete search history.

(56) References Cited

U.S. PATENT DOCUMENTS

| | | | | |
|---|---|---|---|---|
| 6,423,501 | B2 | 7/2002 | Fleming et al. | |
| 6,632,927 | B2 * | 10/2003 | Adair et al. | 530/387.3 |
| 7,026,283 | B2 * | 4/2006 | Fleming et al. | 514/12.2 |
| 2006/0275289 | A1 | 12/2006 | Watanabe et al. | |
| 2007/0264272 | A1 | 11/2007 | Perreault et al. | |
| 2009/0022720 | A1 | 1/2009 | Fischer et al. | |
| 2010/0168210 | A1 | 7/2010 | Edwards, III et al. | |
| 2010/0248254 | A1 | 9/2010 | Perreault et al. | |
| 2011/0034373 | A1 | 2/2011 | Coskun et al. | |

FOREIGN PATENT DOCUMENTS

| | | | |
|---|---|---|---|
| JP | 2009-538599 | A | 11/2009 |
| JP | 2010-528662 | A | 8/2010 |
| JP | 2010-534212 | A | 11/2010 |
| JP | 2010-535781 | A | 11/2010 |
| WO | WO 98/25647 | A1 | 6/1998 |
| WO | WO 00/67796 | A1 | 11/2000 |
| WO | WO 2005/021792 | A1 | 3/2005 |
| WO | WO 2005/082410 | A1 | 9/2005 |
| WO | WO 2010/019570 | A2 | 2/2010 |
| WO | WO 2011/108638 | A1 | 9/2011 |

OTHER PUBLICATIONS

Rudikoff et al. 1982, Proc. Natl. Acad. Sci. USA, 79: 1979-1983.*
Panka et al., 1988, Proc. Natl. Acad. Sci. USA, 85: 3080-3084.*
Dijkstra et al., *Neurobiology of Disease*, 31: 413-421 (2008).
Domanico et al., *Mol. Biol. Cell*, 8(11): 2253-2265 (1997).
Lagaudriere-Gesbert et al., *Cell. Immunol.*, 182: 105-112 (1997).
Pal et al., *Protein Sci.*, 14(9): 2405-13 (2005).
Volkov et al., *Gastroenterol.*, 130(2): 482-492 (2006).
Wright et al., *Immunol. Today*, 15(12): 588-594 (1994).
Yanez-Mo et al., *J. Cell Biol.*, 141(3): 791-804 (1998).
Japanese Patent Office, International Search Report in International Patent Application No. PCT/JP2011/078110 (Mar. 13, 2012).
Cather et al., *Expert Opinion Biol. Ther.*, 3(2): 361-370 (2003).
Cosnes et al., *Inflammatory Bowel Disease*, 8(4): 244-250 (2002).
Dotan et al., *Inflammatory Bowel Disease*, 16(4): 583-592 (2010).
Honey, Karen, *The Journal of Clinical Investigation*, 118(3): 825-826 (2008).
Katz, Seymour, *J. Clin. Gastroenterol.*, 41(9): 799-809 (2007).
McRae et al., *Journal of Neuroimmunology*, 60: 17-28 (1995).
Mikami et al., *The Journal of Pharmacology and Experimental Therapeutics*, 327(2): 383-392 (2008).
Miller et al., *Blood*, 62(5): 988-995 (1983).
Pileri et al., *Science*, 282: 938-941 (1998).
Rutgeerts et al., *The New England Journal of Medicine*, 353(23): 2462-2476 (2005).
Sandborn, William, *Current Gastroenterology Reports*, 5: 501-505 (2003).
Schroff et al., *Cancer Research*, 45: 879-885 (1985).

* cited by examiner

*Primary Examiner* — Ilia Ouspenski
(74) *Attorney, Agent, or Firm* — Leydig, Voit & Mayer, Ltd.

(57) ABSTRACT

The present invention provides an anti-CD81 antibody usable as a pharmaceutical product for human. Specifically, the present invention provides an anti-human CD81 antibody capable of binding to a peptide region consisting of the amino acid sequence of the amino acid numbers 80 to 175 in the amino acid sequence shown in SEQ ID NO:22.

18 Claims, No Drawings

SEQUENCE LISTING

```
<160> NUMBER OF SEQ ID NOS: 166

<210> SEQ ID NO 1
<211> LENGTH: 15
<212> TYPE: PRT
<213> ORGANISM: Homo sapiens

<400> SEQUENCE: 1

Cys Thr Gly Ser Thr Ser Asn Ile Gly Ala Gly Tyr Asp Thr His
1               5                   10                  15


<210> SEQ ID NO 2
<211> LENGTH: 7
<212> TYPE: PRT
<213> ORGANISM: Homo sapiens

<400> SEQUENCE: 2

Gly Asn Ser Asn Arg Pro Ser
1               5


<210> SEQ ID NO 3
<211> LENGTH: 12
<212> TYPE: PRT
<213> ORGANISM: Homo sapiens

<400> SEQUENCE: 3

Cys Gln Ser Tyr Asp Thr Asn Leu Ser Val Trp Val
1               5                   10


<210> SEQ ID NO 4
<211> LENGTH: 14
<212> TYPE: PRT
<213> ORGANISM: Homo sapiens

<400> SEQUENCE: 4

Phe Ser Ser Asn Tyr Met Ser Trp Val Arg Gln Ala Pro Gly
1               5                   10


<210> SEQ ID NO 5
```

<211> LENGTH: 19
<212> TYPE: PRT
<213> ORGANISM: Homo sapiens

<400> SEQUENCE: 5

Ser Tyr Ile Ser Ser Ser Ser Thr Tyr Thr Asp Tyr Ala Asp Ser Val
1 5 10 15

Lys Gly Arg

<210> SEQ ID NO 6
<211> LENGTH: 12
<212> TYPE: PRT
<213> ORGANISM: Homo sapiens

<400> SEQUENCE: 6

Ala Arg Tyr Ser Tyr Gly Arg Asp Asn Phe Asp Tyr
1 5 10

<210> SEQ ID NO 7
<211> LENGTH: 336
<212> TYPE: DNA
<213> ORGANISM: Homo sapiens
<220> FEATURE:
<221> NAME/KEY: CDS
<222> LOCATION: (1)..(336)

<400> SEQUENCE: 7 cag tct gtg ctg act cag cca ccc tca gcg tct ggg acc ccc ggg cag 48
Gln Ser Val Leu Thr Gln Pro Pro Ser Ala Ser Gly Thr Pro Gly Gln
1 5 10 15 agg gtc acc atc tcc tgc act ggg agc acc tcc aac atc ggg gca ggt 96
Arg Val Thr Ile Ser Cys Thr Gly Ser Thr Ser Asn Ile Gly Ala Gly
20 25 30 tat gac aca cac tgg tat cag cag ctc cca gga acg gcc ccc aaa ctc 144
Tyr Asp Thr His Trp Tyr Gln Gln Leu Pro Gly Thr Ala Pro Lys Leu
35 40 45 ctc atc tat ggt aac agc aat cgg ccc tca ggg gtc cct gac cga ttc 192
Leu Ile Tyr Gly Asn Ser Asn Arg Pro Ser Gly Val Pro Asp Arg Phe
50 55 60 tct ggc tcc aag tct ggc acc tca gcc tcc ctg gcc atc agt ggg ctc 240
Ser Gly Ser Lys Ser Gly Thr Ser Ala Ser Leu Ala Ile Ser Gly Leu
65 70 75 80 cgg tcc gag gat gag gct gat tat tac tgc cag tcc tat gac acc aac 288
Arg Ser Glu Asp Glu Ala Asp Tyr Tyr Cys Gln Ser Tyr Asp Thr Asn
85 90 95 ctg agt gtt tgg gtg ttc ggc gga gga acc aag ctg acg gtc cta ggt 336
Leu Ser Val Trp Val Phe Gly Gly Gly Thr Lys Leu Thr Val Leu Gly
100 105 110

<210> SEQ ID NO 8
<211> LENGTH: 112
<212> TYPE: PRT
<213> ORGANISM: Homo sapiens

<400> SEQUENCE: 8

Gln Ser Val Leu Thr Gln Pro Pro Ser Ala Ser Gly Thr Pro Gly Gln
1 5 10 15

Arg Val Thr Ile Ser Cys Thr Gly Ser Thr Ser Asn Ile Gly Ala Gly
20 25 30

Tyr Asp Thr His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

```
Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110


<210> SEQ ID NO 9
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 9

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttc agt agc aac       96
Ser Leu Arg Leu Ser Cys Ala Ala Ser Gly Phe Thr Phe Ser Ser Asn
            20                  25                  30

tac atg agc tgg gtc cgc cag gct cca ggg aag ggg ctg gag tgg gtt      144
Tyr Met Ser Trp Val Arg Gln Ala Pro Gly Lys Gly Leu Glu Trp Val
        35                  40                  45

tca tac att agt agt agt agt act tac aca gac tac gca gac tct gtg      192
Ser Tyr Ile Ser Ser Ser Ser Thr Tyr Thr Asp Tyr Ala Asp Ser Val
    50                  55                  60

aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac act gcc gtg tat tac tgt      288
Leu Gln Met Asn Ser Leu Arg Ala Glu Asp Thr Ala Val Tyr Tyr Cys
                85                  90                  95

gcg aga tac agt tat ggc cgc gac aat ttt gac tac tgg ggc caa ggt      336
Ala Arg Tyr Ser Tyr Gly Arg Asp Asn Phe Asp Tyr Trp Gly Gln Gly
            100                 105                 110

aca ctg gtc acc gtg agc tca                                          357
Thr Leu Val Thr Val Ser Ser
        115


<210> SEQ ID NO 10
<211> LENGTH: 119
<212> TYPE: PRT
<213> ORGANISM: Homo sapiens

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
```

```
            100                 105                 110

Thr Leu Val Thr Val Ser Ser
        115


<210> SEQ ID NO 11
<211> LENGTH: 14
<212> TYPE: PRT
<213> ORGANISM: Homo sapiens

<400> SEQUENCE: 11

Cys Ser Gly Ser Ser Ser Asn Leu Gly Ser Asn Thr Val Asn
1               5                   10


<210> SEQ ID NO 12
<211> LENGTH: 7
<212> TYPE: PRT
<213> ORGANISM: Homo sapiens

<400> SEQUENCE: 12

Gly Asn Ser Asn Arg Pro Ser
1               5


<210> SEQ ID NO 13
<211> LENGTH: 11
<212> TYPE: PRT
<213> ORGANISM: Homo sapiens

<400> SEQUENCE: 13

Cys Glu Val Trp Asp Ser Asp Ser Tyr Val Thr
1               5                   10


<210> SEQ ID NO 14
<211> LENGTH: 14
<212> TYPE: PRT
<213> ORGANISM: Homo sapiens

<400> SEQUENCE: 14

Leu Gly Ser Tyr Trp Met Ser Trp Val Arg Gln Val Pro Gly
1               5                   10


<210> SEQ ID NO 15
<211> LENGTH: 19
<212> TYPE: PRT
<213> ORGANISM: Homo sapiens

<400> SEQUENCE: 15

Ser Ser Ile Ser Ser Ser Ser Ser Tyr Ile Tyr Tyr Ala Asp Ser Val
1               5                   10                  15

Lys Gly Arg


<210> SEQ ID NO 16
<211> LENGTH: 16
<212> TYPE: PRT
<213> ORGANISM: Homo sapiens

<400> SEQUENCE: 16

Ala Arg Gln Arg Ile Gly Asp Leu Val Val His Tyr Gly Leu Asp Val
1               5                   10                  15


<210> SEQ ID NO 17
<211> LENGTH: 330
<212> TYPE: DNA
<213> ORGANISM: Homo sapiens
<220> FEATURE:
<221> NAME/KEY: CDS
```

<222> LOCATION: (1)..(330)

<400> SEQUENCE: 17

```
cag tct gtg ctg act cag cca ccc tca gcg tct ggg acc ccc ggg cag       48
Gln Ser Val Leu Thr Gln Pro Pro Ser Ala Ser Gly Thr Pro Gly Gln
1               5                   10                  15

agg gtc acc atc tct tgt tct gga agc agc tcc aac ctc gga agt aat       96
Arg Val Thr Ile Ser Cys Ser Gly Ser Ser Ser Asn Leu Gly Ser Asn
            20                  25                  30

act gta aac tgg tat cag cag ctc cca gga acg gcc ccc aaa ctc ctc      144
Thr Val Asn Trp Tyr Gln Gln Leu Pro Gly Thr Ala Pro Lys Leu Leu
        35                  40                  45

atc tat ggt aac agc aat cgg ccc tca ggg gtc cct gac cga ttc tct      192
Ile Tyr Gly Asn Ser Asn Arg Pro Ser Gly Val Pro Asp Arg Phe Ser
    50                  55                  60

ggc tcc aag tct ggc acc aca gcc tcc ctg gcc atc agt ggg ctc cgg      240
Gly Ser Lys Ser Gly Thr Thr Ala Ser Leu Ala Ile Ser Gly Leu Arg
65                  70                  75                  80

tcc gag gat gag gct gat tat tac tgt gaa gtc tgg gac agt gac tct      288
Ser Glu Asp Glu Ala Asp Tyr Tyr Cys Glu Val Trp Asp Ser Asp Ser
                85                  90                  95

tat gtg aca ttc ggc gga gga acc aag ctg acg gtc cta ggt              330
Tyr Val Thr Phe Gly Gly Gly Thr Lys Leu Thr Val Leu Gly
            100                 105                 110
```

<210> SEQ ID NO 18
<211> LENGTH: 110
<212> TYPE: PRT
<213> ORGANISM: Homo sapiens

<400> SEQUENCE: 18

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Leu Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Thr Ala Ser Leu Ala Ile Ser Gly Leu Arg
65                  70                  75                  80

Ser Glu Asp Glu Ala Asp Tyr Tyr Cys Glu Val Trp Asp Ser Asp Ser
                85                  90                  95

Tyr Val Thr Phe Gly Gly Gly Thr Lys Leu Thr Val Leu Gly
            100                 105                 110
```

<210> SEQ ID NO 19
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 19

```
gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttg ggt agc tat       96
Ser Leu Arg Leu Ser Cys Ala Ala Ser Gly Phe Thr Leu Gly Ser Tyr
            20                  25                  30
```

```
tgg atg agc tgg gtc cgc cag gtt cca ggg aag ggg ctg gag tgg gtc      144
Trp Met Ser Trp Val Arg Gln Val Pro Gly Lys Gly Leu Glu Trp Val
        35                  40                  45

tca tcc att agt agt agt agt agt tac ata tac tac gca gac tca gtg      192
Ser Ser Ile Ser Ser Ser Ser Ser Tyr Ile Tyr Tyr Ala Asp Ser Val
    50                  55                  60

aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac act gcc gtg tat tac tgt      288
Leu Gln Met Asn Ser Leu Arg Ala Glu Asp Thr Ala Val Tyr Tyr Cys
                85                  90                  95

gcg aga caa cgg att ggc gac tta gtg gtt cac tac ggt ttg gac gtc      336
Ala Arg Gln Arg Ile Gly Asp Leu Val Val His Tyr Gly Leu Asp Val
            100                 105                 110

tgg ggc caa ggt aca ctg gtc acc gtg agc tca                          369
Trp Gly Gln Gly Thr Leu Val Thr Val Ser Ser
        115                 120


<210> SEQ ID NO 20
<211> LENGTH: 123
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Gly Ser Tyr
            20                  25                  30

Trp Met Ser Trp Val Arg Gln Val Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Ile Gly Asp Leu Val Val His Tyr Gly Leu Asp Val
            100                 105                 110

Trp Gly Gln Gly Thr Leu Val Thr Val Ser Ser
        115                 120


<210> SEQ ID NO 21
<211> LENGTH: 711
<212> TYPE: DNA
<213> ORGANISM: Homo sapiens
<220> FEATURE:
<221> NAME/KEY: CDS
<222> LOCATION: (1)..(711)

<400> SEQUENCE: 21

atg gga gtg gag ggc tgc acc aag tgc atc aag tac ctg ctc ttc gtc       48
Met Gly Val Glu Gly Cys Thr Lys Cys Ile Lys Tyr Leu Leu Phe Val
1               5                   10                  15

ttc aat ttc gtc ttc tgg ctg gct gga ggc gtg atc ctg ggt gtg gcc       96
Phe Asn Phe Val Phe Trp Leu Ala Gly Gly Val Ile Leu Gly Val Ala
            20                  25                  30

ctg tgg ctc cgc cat gac ccg cag acc acc aac ctc ctg tat ctg gag      144
Leu Trp Leu Arg His Asp Pro Gln Thr Thr Asn Leu Leu Tyr Leu Glu
        35                  40                  45

ctg gga gac aag ccc gcg ccc aac acc ttc tat gta ggc atc tac atc      192
```

```
Leu Gly Asp Lys Pro Ala Pro Asn Thr Phe Tyr Val Gly Ile Tyr Ile
    50                  55                  60

ctc atc gct gtg ggc gct gtc atg atg ttc gtt ggc ttc ctg ggc tgc      240
Leu Ile Ala Val Gly Ala Val Met Met Phe Val Gly Phe Leu Gly Cys
65                  70                  75                  80

tac ggg gcc atc cag gaa tcc cag tgc ctg ctg ggg acg ttc ttc acc      288
Tyr Gly Ala Ile Gln Glu Ser Gln Cys Leu Leu Gly Thr Phe Phe Thr
                85                  90                  95

tgc ctg gtc atc ctg ttt gcc tgt gag gtg gcc gcc ggc atc tgg ggc      336
Cys Leu Val Ile Leu Phe Ala Cys Glu Val Ala Ala Gly Ile Trp Gly
            100                 105                 110

ttt gtc aac aag gac cag atc gcc aag gat gtg aag cag ttc tat gac      384
Phe Val Asn Lys Asp Gln Ile Ala Lys Asp Val Lys Gln Phe Tyr Asp
        115                 120                 125

cag gcc cta cag cag gcc gtg gtg gat gat gac gcc aac aac gcc aag      432
Gln Ala Leu Gln Gln Ala Val Val Asp Asp Asp Ala Asn Asn Ala Lys
    130                 135                 140

gct gtg gtg aag acc ttc cac gag acg ctt gac tgc tgt ggc tcc agc      480
Ala Val Val Lys Thr Phe His Glu Thr Leu Asp Cys Cys Gly Ser Ser
145                 150                 155                 160

aca ctg act gct ttg acc acc tca gtg ctc aag aac aat ttg tgt ccc      528
Thr Leu Thr Ala Leu Thr Thr Ser Val Leu Lys Asn Asn Leu Cys Pro
                165                 170                 175

tcg ggc agc aac atc atc agc aac ctc ttc aag gag gac tgc cac cag      576
Ser Gly Ser Asn Ile Ile Ser Asn Leu Phe Lys Glu Asp Cys His Gln
            180                 185                 190

aag atc gat gac ctc ttc tcc ggg aag ctg tac ctc atc ggc att gct      624
Lys Ile Asp Asp Leu Phe Ser Gly Lys Leu Tyr Leu Ile Gly Ile Ala
        195                 200                 205

gcc atc gtg gtc gct gtg atc atg atc ttc gag atg atc ctg agc atg      672
Ala Ile Val Val Ala Val Ile Met Ile Phe Glu Met Ile Leu Ser Met
    210                 215                 220

gtg ctg tgc tgt ggc atc cgg aac agc tcc gtg tac tga                  711
Val Leu Cys Cys Gly Ile Arg Asn Ser Ser Val Tyr
225                 230                 235


<210> SEQ ID NO 22
<211> LENGTH: 236
<212> TYPE: PRT
<213> ORGANISM: Homo sapiens

<400> SEQUENCE: 22

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Asn Leu Leu Tyr Leu Glu
        35                  40                  45

Leu Gly Asp Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Val Asp Asp Asp Ala Asn Asn Ala Lys
```

```
    130                 135                 140

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
                165                 170                 175

Ser Gly Ser Asn Ile Ile Ser Asn Leu Phe Lys Glu Asp Cys His Gln
            180                 185                 190

Lys Ile Asp Asp Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
    210                 215                 220

Val Leu Cys Cys Gly Ile Arg Asn Ser Ser Val Tyr
225                 230                 235


<210> SEQ ID NO 23
<211> LENGTH: 714
<212> TYPE: DNA
<213> ORGANISM: Gallus gallus
<220> FEATURE:
<221> NAME/KEY: CDS
<222> LOCATION: (1)..(714)

<400> SEQUENCE: 23

atg ggg gtg gaa ggc tgc acc aag tgc atc aaa tat ctg ctc ttc gtc       48
Met Gly Val Glu Gly Cys Thr Lys Cys Ile Lys Tyr Leu Leu Phe Val
1               5                   10                  15

ttc aac ttc atc ttc tgg ctg gcc ggg ggc atc atc ctg gga gta gcc       96
Phe Asn Phe Ile Phe Trp Leu Ala Gly Gly Ile Ile Leu Gly Val Ala
            20                  25                  30

ctg tgg ctc cgc cat gac tcg cag acc acc aac atc ctc tac ctg cag      144
Leu Trp Leu Arg His Asp Ser Gln Thr Thr Asn Ile Leu Tyr Leu Gln
        35                  40                  45

ctg ggt gac aag cag gct ccc aac acc ttc tat gtc gga atc tac atc      192
Leu Gly Asp Lys Gln Ala Pro Asn Thr Phe Tyr Val Gly Ile Tyr Ile
    50                  55                  60

ctg att gca gtt ggt gct gtc atg atg ttc gtg ggc ttc ctg gga tgc      240
Leu Ile Ala Val Gly Ala Val Met Met Phe Val Gly Phe Leu Gly Cys
65                  70                  75                  80

tac ggt gca atc cag gag tcg cag tgc ctt ctg ggg gcg ttc ttc acc      288
Tyr Gly Ala Ile Gln Glu Ser Gln Cys Leu Leu Gly Ala Phe Phe Thr
                85                  90                  95

tgc ctg gtg att ctg ttt gcc tgt gag gtt gca gct gga atc tgg ggg      336
Cys Leu Val Ile Leu Phe Ala Cys Glu Val Ala Ala Gly Ile Trp Gly
            100                 105                 110

ttt gtc aac aaa gac cag ata gcc aaa gac gtg aag cag ttc tac gac      384
Phe Val Asn Lys Asp Gln Ile Ala Lys Asp Val Lys Gln Phe Tyr Asp
        115                 120                 125

caa gcg ttc caa cag gcg ctc atg gcg gat tcg gac tcg agc aac ggg      432
Gln Ala Phe Gln Gln Ala Leu Met Ala Asp Ser Asp Ser Ser Asn Gly
    130                 135                 140

aag gct gtg gtg aag act ttc cat gaa acg ttg gac tgc tgt ggt cct      480
Lys Ala Val Val Lys Thr Phe His Glu Thr Leu Asp Cys Cys Gly Pro
145                 150                 155                 160

gat act atg gtt gga acg ctc act cct ctg tgg aga gat gac ctg tgc      528
Asp Thr Met Val Gly Thr Leu Thr Pro Leu Trp Arg Asp Asp Leu Cys
                165                 170                 175

tcg aag gac tta ctg aaa ggc ttg ctg aag cgt gag gaa aac tgc cac      576
Ser Lys Asp Leu Leu Lys Gly Leu Leu Lys Arg Glu Glu Asn Cys His
            180                 185                 190

aaa aag atc gac gag ctc ttc tct ggg aag ctg tac ctg atc ggt att      624
```

```
Lys Lys Ile Asp Glu Leu Phe Ser Gly Lys Leu Tyr Leu Ile Gly Ile
        195                 200                 205

gct gcc atc gtg gtt gcc gtg atc atg atc ttc gaa atg atc ctg agc      672
Ala Ala Ile Val Val Ala Val Ile Met Ile Phe Glu Met Ile Leu Ser
    210                 215                 220

atg gtg ctg tgc tgc ggc ata agg aac agc tcc gtc tac tga              714
Met Val Leu Cys Cys Gly Ile Arg Asn Ser Ser Val Tyr
225                 230                 235


<210> SEQ ID NO 24
<211> LENGTH: 237
<212> TYPE: PRT
<213> ORGANISM: Gallus gallus

<400> SEQUENCE: 24

Met Gly Val Glu Gly Cys Thr Lys Cys Ile Lys Tyr Leu Leu Phe Val
1               5                   10                  15

Phe Asn Phe Ile Phe Trp Leu Ala Gly Gly Ile Ile Leu Gly Val Ala
            20                  25                  30

Leu Trp Leu Arg His Asp Ser Gln Thr Thr Asn Ile Leu Tyr Leu Gln
        35                  40                  45

Leu Gly Asp Lys Gln Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Ala Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Phe Gln Gln Ala Leu Met Ala Asp Ser Asp Ser Ser Asn Gly
    130                 135                 140

Lys Ala Val Val Lys Thr Phe His Glu Thr Leu Asp Cys Cys Gly Pro
145                 150                 155                 160

Asp Thr Met Val Gly Thr Leu Thr Pro Leu Trp Arg Asp Asp Leu Cys
                165                 170                 175

Ser Lys Asp Leu Leu Lys Gly Leu Leu Lys Arg Glu Glu Asn Cys His
            180                 185                 190

Lys Lys Ile Asp Glu Leu Phe Ser Gly Lys Leu Tyr Leu Ile Gly Ile
        195                 200                 205

Ala Ala Ile Val Val Ala Val Ile Met Ile Phe Glu Met Ile Leu Ser
    210                 215                 220

Met Val Leu Cys Cys Gly Ile Arg Asn Ser Ser Val Tyr
225                 230                 235


<210> SEQ ID NO 25
<211> LENGTH: 651
<212> TYPE: DNA
<213> ORGANISM: Artificial Sequence
<220> FEATURE:
<223> OTHER INFORMATION: Synthetic Light chain of 002-A07 IgG antibody
<220> FEATURE:
<221> NAME/KEY: CDS
<222> LOCATION: (1)..(651)

<400> SEQUENCE: 25

cag tct gtg ctg act cag cca ccc tca gcg tct ggg acc ccc ggg cag       48
Gln Ser Val Leu Thr Gln Pro Pro Ser Ala Ser Gly Thr Pro Gly Gln
1               5                   10                  15
```

-continued

```
agg gtc acc atc tcc tgc act ggg agc acc tcc aac atc ggg gca ggt      96
Arg Val Thr Ile Ser Cys Thr Gly Ser Thr Ser Asn Ile Gly Ala Gly
            20                  25                  30

tat gac aca cac tgg tat cag cag ctc cca gga acg gcc ccc aaa ctc     144
Tyr Asp Thr His Trp Tyr Gln Gln Leu Pro Gly Thr Ala Pro Lys Leu
        35                  40                  45

ctc atc tat ggt aac agc aat cgg ccc tca ggg gtc cct gac cga ttc     192
Leu Ile Tyr Gly Asn Ser Asn Arg Pro Ser Gly Val Pro Asp Arg Phe
    50                  55                  60

tct ggc tcc aag tct ggc acc tca gcc tcc ctg gcc atc agt ggg ctc     240
Ser Gly Ser Lys Ser Gly Thr Ser Ala Ser Leu Ala Ile Ser Gly Leu
65                  70                  75                  80

cgg tcc gag gat gag gct gat tat tac tgc cag tcc tat gac acc aac     288
Arg Ser Glu Asp Glu Ala Asp Tyr Tyr Cys Gln Ser Tyr Asp Thr Asn
                85                  90                  95

ctg agt gtt tgg gtg ttc ggc gga gga acc aag ctg acg gtc cta ggt     336
Leu Ser Val Trp Val Phe Gly Gly Gly Thr Lys Leu Thr Val Leu Gly
            100                 105                 110

cag ccc aag gct gcc ccc tcg gtc act ctg ttc ccg ccc tcc tct gag     384
Gln Pro Lys Ala Ala Pro Ser Val Thr Leu Phe Pro Pro Ser Ser Glu
        115                 120                 125

gag ctt caa gcc aac aag gcc aca ctg gtg tgt ctc ata agt gac ttc     432
Glu Leu Gln Ala Asn Lys Ala Thr Leu Val Cys Leu Ile Ser Asp Phe
    130                 135                 140

tac ccg gga gcc gtg aca gtg gcc tgg aag gca gat agc agc ccc gtc     480
Tyr Pro Gly Ala Val Thr Val Ala Trp Lys Ala Asp Ser Ser Pro Val
145                 150                 155                 160

aag gcg gga gtg gag acc acc aca ccc tcc aaa caa agc aac aac aag     528
Lys Ala Gly Val Glu Thr Thr Thr Pro Ser Lys Gln Ser Asn Asn Lys
                165                 170                 175

tac gcg gcc agc agc tat ctg agc ctg acg cct gag cag tgg aag tcc     576
Tyr Ala Ala Ser Ser Tyr Leu Ser Leu Thr Pro Glu Gln Trp Lys Ser
            180                 185                 190

cac aga agc tac agc tgc cag gtc acg cat gaa ggg agc acc gtg gag     624
His Arg Ser Tyr Ser Cys Gln Val Thr His Glu Gly Ser Thr Val Glu
        195                 200                 205

aag aca gtg gcc cct aca gaa tgt tca                                 651
Lys Thr Val Ala Pro Thr Glu Cys Ser
    210                 215
```

<210> SEQ ID NO 26
<211> LENGTH: 217
<212> TYPE: PRT
<213> ORGANISM: Artificial Sequence
<220> FEATURE:
<223> OTHER INFORMATION: Synthetic Construct

<400> SEQUENCE: 26

```
Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95
```

```
Leu Ser Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 27
<211> LENGTH: 1338
<212> TYPE: DNA
<213> ORGANISM: Artificial Sequence
<220> FEATURE:
<223> OTHER INFORMATION: Synthetic heavy chain of 002-A07 IgG antibody
<220> FEATURE:
<221> NAME/KEY: CDS
<222> LOCATION: (1)..(1338)

<400> SEQUENCE: 27

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttc agt agc aac       96
Ser Leu Arg Leu Ser Cys Ala Ala Ser Gly Phe Thr Phe Ser Ser Asn
            20                  25                  30

tac atg agc tgg gtc cgc cag gct cca ggg aag ggg ctg gag tgg gtt      144
Tyr Met Ser Trp Val Arg Gln Ala Pro Gly Lys Gly Leu Glu Trp Val
        35                  40                  45

tca tac att agt agt agt agt act tac aca gac tac gca gac tct gtg      192
Ser Tyr Ile Ser Ser Ser Ser Thr Tyr Thr Asp Tyr Ala Asp Ser Val
    50                  55                  60

aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac act gcc gtg tat tac tgt      288
Leu Gln Met Asn Ser Leu Arg Ala Glu Asp Thr Ala Val Tyr Tyr Cys
                85                  90                  95

gcg aga tac agt tat ggc cgc gac aat ttt gac tac tgg ggc caa ggt      336
Ala Arg Tyr Ser Tyr Gly Arg Asp Asn Phe Asp Tyr Trp Gly Gln Gly
            100                 105                 110

aca ctg gtc acc gtg agc tca gct tcc acc aag ggc cca tcc gtc ttc      384
Thr Leu Val Thr Val Ser Ser Ala Ser Thr Lys Gly Pro Ser Val Phe
        115                 120                 125

ccc ctg gcg ccc tgc tcc agg agc acc tcc gag agc aca gcc gcc ctg      432
Pro Leu Ala Pro Cys Ser Arg Ser Thr Ser Glu Ser Thr Ala Ala Leu
    130                 135                 140

ggc tgc ctg gtc aag gac tac ttc ccc gaa ccg gtg acg gtg tcg tgg      480
Gly Cys Leu Val Lys Asp Tyr Phe Pro Glu Pro Val Thr Val Ser Trp
145                 150                 155                 160

aac tca ggc gcc ctg acc agc ggc gtg cac acc ttc ccg gct gtc cta      528
Asn Ser Gly Ala Leu Thr Ser Gly Val His Thr Phe Pro Ala Val Leu
```

```
            165                 170                 175

cag tcc tca gga ctc tac tcc ctc agc agc gtg gtg acc gtg ccc tcc      576
Gln Ser Ser Gly Leu Tyr Ser Leu Ser Ser Val Val Thr Val Pro Ser
        180                 185                 190

agc agc ttg ggc acg aag acc tac acc tgc aac gta gat cac aag ccc      624
Ser Ser Leu Gly Thr Lys Thr Tyr Thr Cys Asn Val Asp His Lys Pro
    195                 200                 205

agc aac acc aag gtg gac aag aga gtt gag tcc aaa tat ggt ccc cca      672
Ser Asn Thr Lys Val Asp Lys Arg Val Glu Ser Lys Tyr Gly Pro Pro
    210                 215                 220

tgc cca cca tgc cca gca cct gag ttc ctg ggg gga cca tca gtc ttc      720
Cys Pro Pro Cys Pro Ala Pro Glu Phe Leu Gly Gly Pro Ser Val Phe
225                 230                 235                 240

ctg ttc ccc cca aaa ccc aag gac act ctc atg atc tcc cgg acc cct      768
Leu Phe Pro Pro Lys Pro Lys Asp Thr Leu Met Ile Ser Arg Thr Pro
            245                 250                 255

gag gtc acg tgc gtg gtg gtg gac gtg agc cag gaa gac ccc gag gtc      816
Glu Val Thr Cys Val Val Val Asp Val Ser Gln Glu Asp Pro Glu Val
        260                 265                 270

cag ttc aac tgg tac gtg gat ggc gtg gag gtg cat aat gcc aag aca      864
Gln Phe Asn Trp Tyr Val Asp Gly Val Glu Val His Asn Ala Lys Thr
    275                 280                 285

aag ccg cgg gag gag cag ttc aac agc acg tac cgt gtg gtc agc gtc      912
Lys Pro Arg Glu Glu Gln Phe Asn Ser Thr Tyr Arg Val Val Ser Val
    290                 295                 300

ctc acc gtc ctg cac cag gac tgg ctg aac ggc aag gag tac aag tgc      960
Leu Thr Val Leu His Gln Asp Trp Leu Asn Gly Lys Glu Tyr Lys Cys
305                 310                 315                 320

aag gtc tcc aac aaa ggc ctc ccg tcc tcc atc gag aaa acc atc tcc     1008
Lys Val Ser Asn Lys Gly Leu Pro Ser Ser Ile Glu Lys Thr Ile Ser
            325                 330                 335

aaa gcc aaa ggg cag ccc cga gag cca cag gtg tac acc ctg ccc cca     1056
Lys Ala Lys Gly Gln Pro Arg Glu Pro Gln Val Tyr Thr Leu Pro Pro
        340                 345                 350

tcc cag gag gag atg acc aag aac cag gtc agc ctg acc tgc ctg gtc     1104
Ser Gln Glu Glu Met Thr Lys Asn Gln Val Ser Leu Thr Cys Leu Val
    355                 360                 365

aaa ggc ttc tac ccc agc gac atc gcc gtg gag tgg gag agc aat ggg     1152
Lys Gly Phe Tyr Pro Ser Asp Ile Ala Val Glu Trp Glu Ser Asn Gly
    370                 375                 380

cag ccg gag aac aac tac aag acc acg cct ccc gtg ctg gac tcc gac     1200
Gln Pro Glu Asn Asn Tyr Lys Thr Thr Pro Pro Val Leu Asp Ser Asp
385                 390                 395                 400

ggc tcc ttc ttc ctc tac agc agg cta acc gtg gac aag agc agg tgg     1248
Gly Ser Phe Phe Leu Tyr Ser Arg Leu Thr Val Asp Lys Ser Arg Trp
            405                 410                 415

cag gag ggg aat gtc ttc tca tgc tcc gtg atg cat gag gct ctg cac     1296
Gln Glu Gly Asn Val Phe Ser Cys Ser Val Met His Glu Ala Leu His
        420                 425                 430

aac cac tac aca cag aag agc ctc tcc ctg tct ctg ggt aaa             1338
Asn His Tyr Thr Gln Lys Ser Leu Ser Leu Ser Leu Gly Lys
    435                 440                 445

<210> SEQ ID NO 28
<211> LENGTH: 446
<212> TYPE: PRT
<213> ORGANISM: Artificial Sequence
<220> FEATURE:
<223> OTHER INFORMATION: Synthetic Construct

<400> SEQUENCE: 28
```

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430
```

-continued

```
Asn His Tyr Thr Gln Lys Ser Leu Ser Leu Ser Leu Gly Lys
        435                 440                 445


<210> SEQ ID NO 29
<211> LENGTH: 645
<212> TYPE: DNA
<213> ORGANISM: Artificial Sequence
<220> FEATURE:
<223> OTHER INFORMATION: Synthetic light chain of 005-C01 IgG antiboy
<220> FEATURE:
<221> NAME/KEY: CDS
<222> LOCATION: (1)..(645)

<400> SEQUENCE: 29

cag tct gtg ctg act cag cca ccc tca gcg tct ggg acc ccc ggg cag       48
Gln Ser Val Leu Thr Gln Pro Pro Ser Ala Ser Gly Thr Pro Gly Gln
1               5                   10                  15

agg gtc acc atc tct tgt tct gga agc agc tcc aac ctc gga agt aat       96
Arg Val Thr Ile Ser Cys Ser Gly Ser Ser Ser Asn Leu Gly Ser Asn
            20                  25                  30

act gta aac tgg tat cag cag ctc cca gga acg gcc ccc aaa ctc ctc      144
Thr Val Asn Trp Tyr Gln Gln Leu Pro Gly Thr Ala Pro Lys Leu Leu
        35                  40                  45

atc tat ggt aac agc aat cgg ccc tca ggg gtc cct gac cga ttc tct      192
Ile Tyr Gly Asn Ser Asn Arg Pro Ser Gly Val Pro Asp Arg Phe Ser
    50                  55                  60

ggc tcc aag tct ggc acc aca gcc tcc ctg gcc atc agt ggg ctc cgg      240
Gly Ser Lys Ser Gly Thr Thr Ala Ser Leu Ala Ile Ser Gly Leu Arg
65                  70                  75                  80

tcc gag gat gag gct gat tat tac tgt gaa gtc tgg gac agt gac tct      288
Ser Glu Asp Glu Ala Asp Tyr Tyr Cys Glu Val Trp Asp Ser Asp Ser
                85                  90                  95

tat gtg aca ttc ggc gga gga acc aag ctg acg gtc cta ggt cag ccc      336
Tyr Val Thr Phe Gly Gly Gly Thr Lys Leu Thr Val Leu Gly Gln Pro
            100                 105                 110

aag gct gcc ccc tcg gtc act ctg ttc ccg ccc tcc tct gag gag ctt      384
Lys Ala Ala Pro Ser Val Thr Leu Phe Pro Pro Ser Ser Glu Glu Leu
        115                 120                 125

caa gcc aac aag gcc aca ctg gtg tgt ctc ata agt gac ttc tac ccg      432
Gln Ala Asn Lys Ala Thr Leu Val Cys Leu Ile Ser Asp Phe Tyr Pro
    130                 135                 140

gga gcc gtg aca gtg gcc tgg aag gca gat agc agc ccc gtc aag gcg      480
Gly Ala Val Thr Val Ala Trp Lys Ala Asp Ser Ser Pro Val Lys Ala
145                 150                 155                 160

gga gtg gag acc acc aca ccc tcc aaa caa agc aac aac aag tac gcg      528
Gly Val Glu Thr Thr Thr Pro Ser Lys Gln Ser Asn Asn Lys Tyr Ala
                165                 170                 175

gcc agc agc tat ctg agc ctg acg cct gag cag tgg aag tcc cac aga      576
Ala Ser Ser Tyr Leu Ser Leu Thr Pro Glu Gln Trp Lys Ser His Arg
            180                 185                 190

agc tac agc tgc cag gtc acg cat gaa ggg agc acc gtg gag aag aca      624
Ser Tyr Ser Cys Gln Val Thr His Glu Gly Ser Thr Val Glu Lys Thr
        195                 200                 205

gtg gcc cct aca gaa tgt tca                                          645
Val Ala Pro Thr Glu Cys Ser
    210                 215


<210> SEQ ID NO 30
<211> LENGTH: 215
<212> TYPE: PRT
<213> ORGANISM: Artificial Sequence
<220> FEATURE:
<223> OTHER INFORMATION: Synthetic Construct
```

<400> SEQUENCE: 30

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Leu Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Thr Ala Ser Leu Ala Ile Ser Gly Leu Arg
65                  70                  75                  80

Ser Glu Asp Glu Ala Asp Tyr Tyr Cys Glu Val Trp Asp Ser Asp Ser
                85                  90                  95

Tyr Val Thr Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 31
<211> LENGTH: 1350
<212> TYPE: DNA
<213> ORGANISM: Artificial Sequence
<220> FEATURE:
<223> OTHER INFORMATION: Synthetic heavy chain of 005-C01 IgG antibody
<220> FEATURE:
<221> NAME/KEY: CDS
<222> LOCATION: (1)..(1350)

<400> SEQUENCE: 31

```
gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttg ggt agc tat       96
Ser Leu Arg Leu Ser Cys Ala Ala Ser Gly Phe Thr Leu Gly Ser Tyr
            20                  25                  30

tgg atg agc tgg gtc cgc cag gtt cca ggg aag ggg ctg gag tgg gtc      144
Trp Met Ser Trp Val Arg Gln Val Pro Gly Lys Gly Leu Glu Trp Val
        35                  40                  45

tca tcc att agt agt agt agt agt tac ata tac tac gca gac tca gtg      192
Ser Ser Ile Ser Ser Ser Ser Ser Tyr Ile Tyr Tyr Ala Asp Ser Val
    50                  55                  60

aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac act gcc gtg tat tac tgt      288
Leu Gln Met Asn Ser Leu Arg Ala Glu Asp Thr Ala Val Tyr Tyr Cys
```

-continued

```
                85                  90                  95

gcg aga caa cgg att ggc gac tta gtg gtt cac tac ggt ttg gac gtc      336
Ala Arg Gln Arg Ile Gly Asp Leu Val Val His Tyr Gly Leu Asp Val
            100                 105                 110

tgg ggc caa ggt aca ctg gtc acc gtg agc tca gct tcc acc aag ggc      384
Trp Gly Gln Gly Thr Leu Val Thr Val Ser Ser Ala Ser Thr Lys Gly
        115                 120                 125

cca tcc gtc ttc ccc ctg gcg ccc tgc tcc agg agc acc tcc gag agc      432
Pro Ser Val Phe Pro Leu Ala Pro Cys Ser Arg Ser Thr Ser Glu Ser
    130                 135                 140

aca gcc gcc ctg ggc tgc ctg gtc aag gac tac ttc ccc gaa ccg gtg      480
Thr Ala Ala Leu Gly Cys Leu Val Lys Asp Tyr Phe Pro Glu Pro Val
145                 150                 155                 160

acg gtg tcg tgg aac tca ggc gcc ctg acc agc ggc gtg cac acc ttc      528
Thr Val Ser Trp Asn Ser Gly Ala Leu Thr Ser Gly Val His Thr Phe
                165                 170                 175

ccg gct gtc cta cag tcc tca gga ctc tac tcc ctc agc agc gtg gtg      576
Pro Ala Val Leu Gln Ser Ser Gly Leu Tyr Ser Leu Ser Ser Val Val
            180                 185                 190

acc gtg ccc tcc agc agc ttg ggc acg aag acc tac acc tgc aac gta      624
Thr Val Pro Ser Ser Ser Leu Gly Thr Lys Thr Tyr Thr Cys Asn Val
        195                 200                 205

gat cac aag ccc agc aac acc aag gtg gac aag aga gtt gag tcc aaa      672
Asp His Lys Pro Ser Asn Thr Lys Val Asp Lys Arg Val Glu Ser Lys
    210                 215                 220

tat ggt ccc cca tgc cca cca tgc cca gca cct gag ttc ctg ggg gga      720
Tyr Gly Pro Pro Cys Pro Pro Cys Pro Ala Pro Glu Phe Leu Gly Gly
225                 230                 235                 240

cca tca gtc ttc ctg ttc ccc cca aaa ccc aag gac act ctc atg atc      768
Pro Ser Val Phe Leu Phe Pro Pro Lys Pro Lys Asp Thr Leu Met Ile
                245                 250                 255

tcc cgg acc cct gag gtc acg tgc gtg gtg gtg gac gtg agc cag gaa      816
Ser Arg Thr Pro Glu Val Thr Cys Val Val Val Asp Val Ser Gln Glu
            260                 265                 270

gac ccc gag gtc cag ttc aac tgg tac gtg gat ggc gtg gag gtg cat      864
Asp Pro Glu Val Gln Phe Asn Trp Tyr Val Asp Gly Val Glu Val His
        275                 280                 285

aat gcc aag aca aag ccg cgg gag gag cag ttc aac agc acg tac cgt      912
Asn Ala Lys Thr Lys Pro Arg Glu Glu Gln Phe Asn Ser Thr Tyr Arg
    290                 295                 300

gtg gtc agc gtc ctc acc gtc ctg cac cag gac tgg ctg aac ggc aag      960
Val Val Ser Val Leu Thr Val Leu His Gln Asp Trp Leu Asn Gly Lys
305                 310                 315                 320

gag tac aag tgc aag gtc tcc aac aaa ggc ctc ccg tcc tcc atc gag     1008
Glu Tyr Lys Cys Lys Val Ser Asn Lys Gly Leu Pro Ser Ser Ile Glu
                325                 330                 335

aaa acc atc tcc aaa gcc aaa ggg cag ccc cga gag cca cag gtg tac     1056
Lys Thr Ile Ser Lys Ala Lys Gly Gln Pro Arg Glu Pro Gln Val Tyr
            340                 345                 350

acc ctg ccc cca tcc cag gag gag atg acc aag aac cag gtc agc ctg     1104
Thr Leu Pro Pro Ser Gln Glu Glu Met Thr Lys Asn Gln Val Ser Leu
        355                 360                 365

acc tgc ctg gtc aaa ggc ttc tac ccc agc gac atc gcc gtg gag tgg     1152
Thr Cys Leu Val Lys Gly Phe Tyr Pro Ser Asp Ile Ala Val Glu Trp
    370                 375                 380

gag agc aat ggg cag ccg gag aac aac tac aag acc acg cct ccc gtg     1200
Glu Ser Asn Gly Gln Pro Glu Asn Asn Tyr Lys Thr Thr Pro Pro Val
385                 390                 395                 400

ctg gac tcc gac ggc tcc ttc ttc ctc tac agc agg cta acc gtg gac     1248
Leu Asp Ser Asp Gly Ser Phe Phe Leu Tyr Ser Arg Leu Thr Val Asp
```

```
            405                 410                 415

aag agc agg tgg cag gag ggg aat gtc ttc tca tgc tcc gtg atg cat      1296
Lys Ser Arg Trp Gln Glu Gly Asn Val Phe Ser Cys Ser Val Met His
            420                 425                 430

gag gct ctg cac aac cac tac aca cag aag agc ctc tcc ctg tct ctg      1344
Glu Ala Leu His Asn His Tyr Thr Gln Lys Ser Leu Ser Leu Ser Leu
        435                 440                 445

ggt aaa                                                              1350
Gly Lys
    450


<210> SEQ ID NO 32
<211> LENGTH: 450
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Gly Ser Tyr
            20                  25                  30

Trp Met Ser Trp Val Arg Gln Val Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Ile Gly Asp Leu Val Val His Tyr Gly Leu Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450


<210> SEQ ID NO 33
<211> LENGTH: 804
<212> TYPE: DNA
<213> ORGANISM: Artificial Sequence
<220> FEATURE:
<223> OTHER INFORMATION: Synthetic scFv-002-A07
<220> FEATURE:
<221> NAME/KEY: CDS
<222> LOCATION: (1)..(804)

<400> SEQUENCE: 33

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttc agt agc aac       96
Ser Leu Arg Leu Ser Cys Ala Ala Ser Gly Phe Thr Phe Ser Ser Asn
            20                  25                  30

tac atg agc tgg gtc cgc cag gct cca ggg aag ggg ctg gag tgg gtt      144
Tyr Met Ser Trp Val Arg Gln Ala Pro Gly Lys Gly Leu Glu Trp Val
        35                  40                  45

tca tac att agt agt agt agt act tac aca gac tac gca gac tct gtg      192
Ser Tyr Ile Ser Ser Ser Ser Thr Tyr Thr Asp Tyr Ala Asp Ser Val
    50                  55                  60

aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac act gcc gtg tat tac tgt      288
Leu Gln Met Asn Ser Leu Arg Ala Glu Asp Thr Ala Val Tyr Tyr Cys
                85                  90                  95

gcg aga tac agt tat ggc cgc gac aat ttt gac tac tgg ggc caa ggt      336
Ala Arg Tyr Ser Tyr Gly Arg Asp Asn Phe Asp Tyr Trp Gly Gln Gly
            100                 105                 110

aca ctg gtc acc gtg agc agc ggt gga ggc ggt tca ggc gga ggt gga      384
Thr Leu Val Thr Val Ser Ser Gly Gly Gly Gly Ser Gly Gly Gly Gly
        115                 120                 125

tcc ggc ggt ggc gga tcg cag tct gtg ctg act cag cca ccc tca gcg      432
Ser Gly Gly Gly Gly Ser Gln Ser Val Leu Thr Gln Pro Pro Ser Ala
    130                 135                 140
```

```
tct ggg acc ccc ggg cag agg gtc acc atc tcc tgc act ggg agc acc      480
Ser Gly Thr Pro Gly Gln Arg Val Thr Ile Ser Cys Thr Gly Ser Thr
145                 150                 155                 160

tcc aac atc ggg gca ggt tat gac aca cac tgg tat cag cag ctc cca      528
Ser Asn Ile Gly Ala Gly Tyr Asp Thr His Trp Tyr Gln Gln Leu Pro
                165                 170                 175

gga acg gcc ccc aaa ctc ctc atc tat ggt aac agc aat cgg ccc tca      576
Gly Thr Ala Pro Lys Leu Leu Ile Tyr Gly Asn Ser Asn Arg Pro Ser
            180                 185                 190

ggg gtc cct gac cga ttc tct ggc tcc aag tct ggc acc tca gcc tcc      624
Gly Val Pro Asp Arg Phe Ser Gly Ser Lys Ser Gly Thr Ser Ala Ser
        195                 200                 205

ctg gcc atc agt ggg ctc cgg tcc gag gat gag gct gat tat tac tgc      672
Leu Ala Ile Ser Gly Leu Arg Ser Glu Asp Glu Ala Asp Tyr Tyr Cys
    210                 215                 220

cag tcc tat gac acc aac ctg agt gtt tgg gtg ttc ggc gga gga acc      720
Gln Ser Tyr Asp Thr Asn Leu Ser Val Trp Val Phe Gly Gly Gly Thr
225                 230                 235                 240

aag ctg acg gtc cta ggt gaa caa aaa ctc atc tca gaa gag gat ctg      768
Lys Leu Thr Val Leu Gly Glu Gln Lys Leu Ile Ser Glu Glu Asp Leu
                245                 250                 255

tct gga tca gcg gcc gcc cat cat cat cat cat cat                      804
Ser Gly Ser Ala Ala Ala His His His His His His
            260                 265


<210> SEQ ID NO 34
<211> LENGTH: 268
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Ser Val Leu Thr Gln Pro Pro Ser Ala
    130                 135                 140

Ser Gly Thr Pro Gly Gln Arg Val Thr Ile Ser Cys Thr Gly Ser Thr
145                 150                 155                 160

Ser Asn Ile Gly Ala Gly Tyr Asp Thr His Trp Tyr Gln Gln Leu Pro
                165                 170                 175

Gly Thr Ala Pro Lys Leu Leu Ile Tyr Gly Asn Ser Asn Arg Pro Ser
            180                 185                 190

Gly Val Pro Asp Arg Phe Ser Gly Ser Lys Ser Gly Thr Ser Ala Ser
        195                 200                 205
```

```
Leu Ala Ile Ser Gly Leu Arg Ser Glu Asp Glu Ala Asp Tyr Tyr Cys
    210                 215                 220

Gln Ser Tyr Asp Thr Asn Leu Ser Val Trp Val Phe Gly Gly Gly Thr
225                 230                 235                 240

Lys Leu Thr Val Leu Gly Glu Gln Lys Leu Ile Ser Glu Glu Asp Leu
                245                 250                 255

Ser Gly Ser Ala Ala Ala His His His His His His
            260                 265


<210> SEQ ID NO 35
<211> LENGTH: 810
<212> TYPE: DNA
<213> ORGANISM: Artificial Sequence
<220> FEATURE:
<223> OTHER INFORMATION: Synthetic scFv-005-C01
<220> FEATURE:
<221> NAME/KEY: CDS
<222> LOCATION: (1)..(810)

<400> SEQUENCE: 35

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttg ggt agc tat       96
Ser Leu Arg Leu Ser Cys Ala Ala Ser Gly Phe Thr Leu Gly Ser Tyr
            20                  25                  30

tgg atg agc tgg gtc cgc cag gtt cca ggg aag ggg ctg gag tgg gtc      144
Trp Met Ser Trp Val Arg Gln Val Pro Gly Lys Gly Leu Glu Trp Val
        35                  40                  45

tca tcc att agt agt agt agt agt tac ata tac tac gca gac tca gtg      192
Ser Ser Ile Ser Ser Ser Ser Ser Tyr Ile Tyr Tyr Ala Asp Ser Val
    50                  55                  60

aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac act gcc gtg tat tac tgt      288
Leu Gln Met Asn Ser Leu Arg Ala Glu Asp Thr Ala Val Tyr Tyr Cys
                85                  90                  95

gcg aga caa cgg att ggc gac tta gtg gtt cac tac ggt ttg gac gtc      336
Ala Arg Gln Arg Ile Gly Asp Leu Val Val His Tyr Gly Leu Asp Val
            100                 105                 110

tgg ggc caa ggt aca ctg gtc acc gtg agc agc ggt gga ggc ggt tca      384
Trp Gly Gln Gly Thr Leu Val Thr Val Ser Ser Gly Gly Gly Gly Ser
        115                 120                 125

ggc gga ggt gga tcc ggc ggt ggc gga tcg cag tct gtg ctg act cag      432
Gly Gly Gly Gly Ser Gly Gly Gly Gly Ser Gln Ser Val Leu Thr Gln
    130                 135                 140

cca ccc tca gcg tct ggg acc ccc ggg cag agg gtc acc atc tct tgt      480
Pro Pro Ser Ala Ser Gly Thr Pro Gly Gln Arg Val Thr Ile Ser Cys
145                 150                 155                 160

tct gga agc agc tcc aac ctc gga agt aat act gta aac tgg tat cag      528
Ser Gly Ser Ser Ser Asn Leu Gly Ser Asn Thr Val Asn Trp Tyr Gln
                165                 170                 175

cag ctc cca gga acg gcc ccc aaa ctc ctc atc tat ggt aac agc aat      576
Gln Leu Pro Gly Thr Ala Pro Lys Leu Leu Ile Tyr Gly Asn Ser Asn
            180                 185                 190

cgg ccc tca ggg gtc cct gac cga ttc tct ggc tcc aag tct ggc acc      624
Arg Pro Ser Gly Val Pro Asp Arg Phe Ser Gly Ser Lys Ser Gly Thr
        195                 200                 205

aca gcc tcc ctg gcc atc agt ggg ctc cgg tcc gag gat gag gct gat      672
Thr Ala Ser Leu Ala Ile Ser Gly Leu Arg Ser Glu Asp Glu Ala Asp
```

```
    210                 215                 220

tat tac tgt gaa gtc tgg gac agt gac tct tat gtg aca ttc ggc gga      720
Tyr Tyr Cys Glu Val Trp Asp Ser Asp Ser Tyr Val Thr Phe Gly Gly
225                 230                 235                 240

gga acc aag ctg acg gtc cta ggt gaa caa aaa ctc atc tca gaa gag      768
Gly Thr Lys Leu Thr Val Leu Gly Glu Gln Lys Leu Ile Ser Glu Glu
                245                 250                 255

gat ctg tct gga tca gcg gcc gcc cat cat cat cat cat cat              810
Asp Leu Ser Gly Ser Ala Ala Ala His His His His His His
            260                 265                 270
```

```
<210> SEQ ID NO 36
<211> LENGTH: 270
<212> TYPE: PRT
<213> ORGANISM: Artificial Sequence
<220> FEATURE:
<223> OTHER INFORMATION: Synthetic Construct

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Gly Ser Tyr
            20                  25                  30

Trp Met Ser Trp Val Arg Gln Val Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Ile Gly Asp Leu Val Val His Tyr Gly Leu Asp Val
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gln Ser Val Leu Thr Gln
    130                 135                 140

Pro Pro Ser Ala Ser Gly Thr Pro Gly Gln Arg Val Thr Ile Ser Cys
145                 150                 155                 160

Ser Gly Ser Ser Ser Asn Leu Gly Ser Asn Thr Val Asn Trp Tyr Gln
                165                 170                 175

Gln Leu Pro Gly Thr Ala Pro Lys Leu Leu Ile Tyr Gly Asn Ser Asn
            180                 185                 190

Arg Pro Ser Gly Val Pro Asp Arg Phe Ser Gly Ser Lys Ser Gly Thr
        195                 200                 205

Thr Ala Ser Leu Ala Ile Ser Gly Leu Arg Ser Glu Asp Glu Ala Asp
    210                 215                 220

Tyr Tyr Cys Glu Val Trp Asp Ser Asp Ser Tyr Val Thr Phe Gly Gly
225                 230                 235                 240

Gly Thr Lys Leu Thr Val Leu Gly Glu Gln Lys Leu Ile Ser Glu Glu
                245                 250                 255

Asp Leu Ser Gly Ser Ala Ala Ala His His His His His His
            260                 265                 270
```

```
<210> SEQ ID NO 37
<211> LENGTH: 12
<212> TYPE: PRT
<213> ORGANISM: Artificial Sequence
```

<220> FEATURE:
<223> OTHER INFORMATION: Synthetic Construct

<400> SEQUENCE: 37

Cys Gln Ser Tyr Asp Thr Gly Leu Ser Val Trp Val
1 5 10

<210> SEQ ID NO 38
<211> LENGTH: 112
<212> TYPE: PRT
<213> ORGANISM: Artificial Sequence
<220> FEATURE:
<223> OTHER INFORMATION: Synthetic Construct

<400> SEQUENCE: 38

Gln Ser Val Leu Thr Gln Pro Pro Ser Ala Ser Gly Thr Pro Gly Gln
1 5 10 15

Arg Val Thr Ile Ser Cys Thr Gly Ser Thr Ser Asn Ile Gly Ala Gly
20 25 30

Tyr Asp Thr His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Ser Gly Leu
65 70 75 80

Arg Ser Glu Asp Glu Ala Asp Tyr Tyr Cys Gln Ser Tyr Asp Thr Gly
85 90 95

Leu Ser Val Trp Val Phe Gly Gly Gly Thr Lys Leu Thr Val Leu Gly
100 105 110

<210> SEQ ID NO 39
<211> LENGTH: 217
<212> TYPE: PRT
<213> ORGANISM: Artificial Sequence
<220> FEATURE:
<223> OTHER INFORMATION: Synthetic Construct

<400> SEQUENCE: 39

Gln Ser Val Leu Thr Gln Pro Pro Ser Ala Ser Gly Thr Pro Gly Gln
1 5 10 15

Arg Val Thr Ile Ser Cys Thr Gly Ser Thr Ser Asn Ile Gly Ala Gly
20 25 30

Tyr Asp Thr His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Ser Gly Leu
65 70 75 80

Arg Ser Glu Asp Glu Ala Asp Tyr Tyr Cys Gln Ser Tyr Asp Thr Gly
85 90 95

Leu Ser Val Trp Val Phe Gly Gly Gly Thr Lys Leu Thr Val Leu Gly
100 105 110

Gln Pro Lys Ala Ala Pro Ser Val Thr Leu Phe Pro Pro Ser Ser Glu
115 120 125

Glu Leu Gln Ala Asn Lys Ala Thr Leu Val Cys Leu Ile Ser Asp Phe
130 135 140

Tyr Pro Gly Ala Val Thr Val Ala Trp Lys Ala Asp Ser Ser Pro Val
145 150 155 160

Lys Ala Gly Val Glu Thr Thr Thr Pro Ser Lys Gln Ser Asn Asn Lys

```
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 40
<211> LENGTH: 12
<212> TYPE: PRT
<213> ORGANISM: Artificial Sequence
<220> FEATURE:
<223> OTHER INFORMATION: Synthetic Construct

<400> SEQUENCE: 40

Cys Gln Ser Tyr Asp Thr Gln Leu Ser Val Trp Val
1               5                   10


<210> SEQ ID NO 41
<211> LENGTH: 112
<212> TYPE: PRT
<213> ORGANISM: Artificial Sequence
<220> FEATURE:
<223> OTHER INFORMATION: Synthetic Construct

<400> SEQUENCE: 41

Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Gln
                85                  90                  95

Leu Ser Val Trp Val Phe Gly Gly Gly Thr Lys Leu Thr Val Leu Gly
            100                 105                 110


<210> SEQ ID NO 42
<211> LENGTH: 217
<212> TYPE: PRT
<213> ORGANISM: Artificial Sequence
<220> FEATURE:
<223> OTHER INFORMATION: Synthetic Construct

<400> SEQUENCE: 42

Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80
```

-continued

```
Arg Ser Glu Asp Glu Ala Asp Tyr Tyr Cys Gln Ser Tyr Asp Thr Gln
                85                  90                  95

Leu Ser Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 43
<211> LENGTH: 12
<212> TYPE: PRT
<213> ORGANISM: Artificial Sequence
<220> FEATURE:
<223> OTHER INFORMATION: Synthetic Construct

<400> SEQUENCE: 43

Cys Gln Ser Tyr Asp Thr Ser Leu Ser Val Trp Val
1               5                   10


<210> SEQ ID NO 44
<211> LENGTH: 112
<212> TYPE: PRT
<213> ORGANISM: Artificial Sequence
<220> FEATURE:
<223> OTHER INFORMATION: Synthetic Construct

<400> SEQUENCE: 44

Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Ser
                85                  90                  95

Leu Ser Val Trp Val Phe Gly Gly Gly Thr Lys Leu Thr Val Leu Gly
            100                 105                 110


<210> SEQ ID NO 45
<211> LENGTH: 217
<212> TYPE: PRT
<213> ORGANISM: Artificial Sequence
<220> FEATURE:
<223> OTHER INFORMATION: Synthetic Construct

<400> SEQUENCE: 45
```

```
Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Ser
                85                  90                  95

Leu Ser Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

```
<210> SEQ ID NO 46
<211> LENGTH: 12
<212> TYPE: PRT
<213> ORGANISM: Artificial Sequence
<220> FEATURE:
<223> OTHER INFORMATION: Synthetic Construct

<400> SEQUENCE: 46

Cys Gln Ser Tyr Asp Thr Asn Leu Ala Val Trp Val
1               5                   10
```

```
<210> SEQ ID NO 47
<211> LENGTH: 112
<212> TYPE: PRT
<213> ORGANISM: Artificial Sequence
<220> FEATURE:
<223> OTHER INFORMATION: Synthetic Construct

<400> SEQUENCE: 47

Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80
```

```
Arg Ser Glu Asp Glu Ala Asp Tyr Tyr Cys Gln Ser Tyr Asp Thr Asn
                85                  90                  95

Leu Ala Val Trp Val Phe Gly Gly Gly Thr Lys Leu Thr Val Leu Gly
            100                 105                 110


<210> SEQ ID NO 48
<211> LENGTH: 217
<212> TYPE: PRT
<213> ORGANISM: Artificial Sequence
<220> FEATURE:
<223> OTHER INFORMATION: Synthetic Construct

<400> SEQUENCE: 48

Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ala Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 49
<211> LENGTH: 12
<212> TYPE: PRT
<213> ORGANISM: Artificial Sequence
<220> FEATURE:
<223> OTHER INFORMATION: Synthetic Construct

<400> SEQUENCE: 49

Cys Gln Ser Tyr Asp Thr Asn Leu Gly Val Trp Val
1               5                   10


<210> SEQ ID NO 50
<211> LENGTH: 112
<212> TYPE: PRT
<213> ORGANISM: Artificial Sequence
<220> FEATURE:
<223> OTHER INFORMATION: Synthetic Construct
```

<400> SEQUENCE: 50

```
Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Gly Val Trp Val Phe Gly Gly Gly Thr Lys Leu Thr Val Leu Gly
            100                 105                 110
```

<210> SEQ ID NO 51
<211> LENGTH: 217
<212> TYPE: PRT
<213> ORGANISM: Artificial Sequence
<220> FEATURE:
<223> OTHER INFORMATION: Synthetic Construct

<400> SEQUENCE: 51

```
Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Gly Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 52
<211> LENGTH: 12
<212> TYPE: PRT
<213> ORGANISM: Artificial Sequence
<220> FEATURE:
<223> OTHER INFORMATION: Synthetic Construct

<400> SEQUENCE: 52

Cys Gln Ser Tyr Asp Thr Asn Leu Asn Val Trp Val
1 5 10

<210> SEQ ID NO 53
<211> LENGTH: 112
<212> TYPE: PRT
<213> ORGANISM: Artificial Sequence
<220> FEATURE:
<223> OTHER INFORMATION: Synthetic Construct

<400> SEQUENCE: 53

Gln Ser Val Leu Thr Gln Pro Pro Ser Ala Ser Gly Thr Pro Gly Gln
1 5 10 15

Arg Val Thr Ile Ser Cys Thr Gly Ser Thr Ser Asn Ile Gly Ala Gly
20 25 30

Tyr Asp Thr His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Ser Gly Leu
65 70 75 80

Arg Ser Glu Asp Glu Ala Asp Tyr Tyr Cys Gln Ser Tyr Asp Thr Asn
85 90 95

Leu Asn Val Trp Val Phe Gly Gly Gly Thr Lys Leu Thr Val Leu Gly
100 105 110

<210> SEQ ID NO 54
<211> LENGTH: 217
<212> TYPE: PRT
<213> ORGANISM: Artificial Sequence
<220> FEATURE:
<223> OTHER INFORMATION: Synthetic Construct

<400> SEQUENCE: 54

Gln Ser Val Leu Thr Gln Pro Pro Ser Ala Ser Gly Thr Pro Gly Gln
1 5 10 15

Arg Val Thr Ile Ser Cys Thr Gly Ser Thr Ser Asn Ile Gly Ala Gly
20 25 30

Tyr Asp Thr His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Ser Gly Leu
65 70 75 80

Arg Ser Glu Asp Glu Ala Asp Tyr Tyr Cys Gln Ser Tyr Asp Thr Asn
85 90 95

Leu Asn Val Trp Val Phe Gly Gly Gly Thr Lys Leu Thr Val Leu Gly
100 105 110

Gln Pro Lys Ala Ala Pro Ser Val Thr Leu Phe Pro Pro Ser Ser Glu
115 120 125

Glu Leu Gln Ala Asn Lys Ala Thr Leu Val Cys Leu Ile Ser Asp Phe
130 135 140

Tyr Pro Gly Ala Val Thr Val Ala Trp Lys Ala Asp Ser Ser Pro Val
145 150 155 160

Lys Ala Gly Val Glu Thr Thr Thr Pro Ser Lys Gln Ser Asn Asn Lys

-continued 165 170 175

Tyr Ala Ala Ser Ser Tyr Leu Ser Leu Thr Pro Glu Gln Trp Lys Ser
180 185 190

His Arg Ser Tyr Ser Cys Gln Val Thr His Glu Gly Ser Thr Val Glu
195 200 205

Lys Thr Val Ala Pro Thr Glu Cys Ser
210 215

<210> SEQ ID NO 55
<211> LENGTH: 12
<212> TYPE: PRT
<213> ORGANISM: Artificial Sequence
<220> FEATURE:
<223> OTHER INFORMATION: Synthetic Construct

<400> SEQUENCE: 55

Ala Arg Tyr Ser Tyr Gly Arg Asp Thr Phe Asp Tyr
1 5 10

<210> SEQ ID NO 56
<211> LENGTH: 112
<212> TYPE: PRT
<213> ORGANISM: Artificial Sequence
<220> FEATURE:
<223> OTHER INFORMATION: Synthetic Construct

<400> SEQUENCE: 56

Gln Ser Val Leu Thr Gln Pro Phe Ser Ala Ser Gly Thr Pro Gly Gln
1 5 10 15

Arg Val Thr Ile Ser Cys Thr Gly Ser Thr Ser Asn Ile Gly Ala Gly
20 25 30

Tyr Asp Thr His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Ser Gly Leu
65 70 75 80

Arg Pro Glu Asp Glu Ala Asp Tyr Tyr Cys Gln Ser Tyr Asp Thr Ser
85 90 95

Leu Ser Val Trp Val Phe Gly Gly Gly Thr Lys Leu Thr Val Leu Gly
100 105 110

<210> SEQ ID NO 57
<211> LENGTH: 119
<212> TYPE: PRT
<213> ORGANISM: Artificial Sequence
<220> FEATURE:
<223> OTHER INFORMATION: Synthetic Construct

<400> SEQUENCE: 57

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Asn
20 25 30

Tyr Met Ser Trp Val Arg Gln Ala Pro Gly Lys Gly Leu Glu Trp Val
35 40 45

Ser Tyr Ile Ser Ser Ser Ser Thr Tyr Thr Asp Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Ser Tyr Gly Arg Asp Thr Phe Asp Tyr Trp Gly Gln Gly
100 105 110

Thr Leu Val Thr Val Ser Ser
115

<210> SEQ ID NO 58
<211> LENGTH: 217
<212> TYPE: PRT
<213> ORGANISM: Artificial Sequence
<220> FEATURE:
<223> OTHER INFORMATION: Synthetic Construct

<400> SEQUENCE: 58

Gln Ser Val Leu Thr Gln Pro Phe Ser Ala Ser Gly Thr Pro Gly Gln
1 5 10 15

Arg Val Thr Ile Ser Cys Thr Gly Ser Thr Ser Asn Ile Gly Ala Gly
20 25 30

Tyr Asp Thr His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Ser Gly Leu
65 70 75 80

Arg Pro Glu Asp Glu Ala Asp Tyr Tyr Cys Gln Ser Tyr Asp Thr Ser
85 90 95

Leu Ser Val Trp Val Phe Gly Gly Gly Thr Lys Leu Thr Val Leu Gly
100 105 110

Gln Pro Lys Ala Ala Pro Ser Val Thr Leu Phe Pro Pro Ser Ser Glu
115 120 125

Glu Leu Gln Ala Asn Lys Ala Thr Leu Val Cys Leu Ile Ser Asp Phe
130 135 140

Tyr Pro Gly Ala Val Thr Val Ala Trp Lys Ala Asp Ser Ser Pro Val
145 150 155 160

Lys Ala Gly Val Glu Thr Thr Thr Pro Ser Lys Gln Ser Asn Asn Lys
165 170 175

Tyr Ala Ala Ser Ser Tyr Leu Ser Leu Thr Pro Glu Gln Trp Lys Ser
180 185 190

His Arg Ser Tyr Ser Cys Gln Val Thr His Glu Gly Ser Thr Val Glu
195 200 205

Lys Thr Val Ala Pro Thr Glu Cys Ser
210 215

<210> SEQ ID NO 59
<211> LENGTH: 446
<212> TYPE: PRT
<213> ORGANISM: Artificial Sequence
<220> FEATURE:
<223> OTHER INFORMATION: Synthetic Construct

<400> SEQUENCE: 59

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Asn
20 25 30

Tyr Met Ser Trp Val Arg Gln Ala Pro Gly Lys Gly Leu Glu Trp Val
35 40 45

-continued

```
Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Thr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```

<210> SEQ ID NO 60
<211> LENGTH: 15
<212> TYPE: PRT
<213> ORGANISM: Artificial Sequence
<220> FEATURE:
<223> OTHER INFORMATION: Synthetic Construct

<400> SEQUENCE: 60

Cys Thr Gly Ser Thr Ser Asn Ile Gly Ala Gly Tyr Gly Thr His
1 5 10 15

<210> SEQ ID NO 61
<211> LENGTH: 12
<212> TYPE: PRT
<213> ORGANISM: Artificial Sequence
<220> FEATURE:
<223> OTHER INFORMATION: Synthetic Construct

<400> SEQUENCE: 61

Ala Arg Tyr Ser Tyr Ser Arg Asp Asn Phe Asp Tyr
1 5 10

<210> SEQ ID NO 62
<211> LENGTH: 112
<212> TYPE: PRT
<213> ORGANISM: Artificial Sequence
<220> FEATURE:
<223> OTHER INFORMATION: Synthetic Construct

<400> SEQUENCE: 62

Gln Ser Val Leu Thr Gln Pro Pro Ser Ala Ser Gly Thr Pro Gly Gln
1 5 10 15

Arg Val Thr Ile Ser Cys Thr Gly Ser Thr Ser Asn Ile Gly Ala Gly
20 25 30

Tyr Gly Thr His Trp Tyr Gln Arg Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Ser Gly Leu
65 70 75 80

Arg Ser Glu Asp Glu Ala Asp Tyr Tyr Cys Gln Ser Tyr Asp Thr Asn
85 90 95

Leu Ser Val Trp Val Phe Gly Gly Gly Thr Lys Leu Thr Val Leu Gly
100 105 110

<210> SEQ ID NO 63
<211> LENGTH: 119
<212> TYPE: PRT
<213> ORGANISM: Artificial Sequence
<220> FEATURE:
<223> OTHER INFORMATION: Synthetic Construct

<400> SEQUENCE: 63

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Asn
20 25 30

Tyr Met Ser Trp Val Arg Gln Ala Pro Gly Lys Gly Leu Glu Trp Val
35 40 45

Ser Tyr Ile Ser Ser Ser Ser Thr Tyr Thr Asp Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Ser Tyr Ser Arg Asp Asn Phe Asp Tyr Trp Gly Gln Gly
100 105 110

Thr Leu Val Thr Val Ser Ser
115

<210> SEQ ID NO 64
<211> LENGTH: 217
<212> TYPE: PRT
<213> ORGANISM: Artificial Sequence
<220> FEATURE:
<223> OTHER INFORMATION: Synthetic Construct

<400> SEQUENCE: 64

Gln Ser Val Leu Thr Gln Pro Pro Ser Ala Ser Gly Thr Pro Gly Gln
1 5 10 15

Arg Val Thr Ile Ser Cys Thr Gly Ser Thr Ser Asn Ile Gly Ala Gly
20 25 30

Tyr Gly Thr His Trp Tyr Gln Arg Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Ser Gly Leu
65 70 75 80

Arg Ser Glu Asp Glu Ala Asp Tyr Tyr Cys Gln Ser Tyr Asp Thr Asn
85 90 95

Leu Ser Val Trp Val Phe Gly Gly Gly Thr Lys Leu Thr Val Leu Gly
100 105 110

Gln Pro Lys Ala Ala Pro Ser Val Thr Leu Phe Pro Pro Ser Ser Glu
115 120 125

Glu Leu Gln Ala Asn Lys Ala Thr Leu Val Cys Leu Ile Ser Asp Phe
130 135 140

Tyr Pro Gly Ala Val Thr Val Ala Trp Lys Ala Asp Ser Ser Pro Val
145 150 155 160

Lys Ala Gly Val Glu Thr Thr Thr Pro Ser Lys Gln Ser Asn Asn Lys
165 170 175

Tyr Ala Ala Ser Ser Tyr Leu Ser Leu Thr Pro Glu Gln Trp Lys Ser
180 185 190

His Arg Ser Tyr Ser Cys Gln Val Thr His Glu Gly Ser Thr Val Glu
195 200 205

Lys Thr Val Ala Pro Thr Glu Cys Ser
210 215

<210> SEQ ID NO 65
<211> LENGTH: 446
<212> TYPE: PRT
<213> ORGANISM: Artificial Sequence
<220> FEATURE:
<223> OTHER INFORMATION: Synthetic Construct

<400> SEQUENCE: 65

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Asn
20 25 30

Tyr Met Ser Trp Val Arg Gln Ala Pro Gly Lys Gly Leu Glu Trp Val
35 40 45

Ser Tyr Ile Ser Ser Ser Ser Thr Tyr Thr Asp Tyr Ala Asp Ser Val
50 55 60

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Ser Arg Asp Asn Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```

<210> SEQ ID NO 66
<211> LENGTH: 12
<212> TYPE: PRT
<213> ORGANISM: Artificial Sequence
<220> FEATURE:
<223> OTHER INFORMATION: Synthetic Construct -continued

<400> SEQUENCE: 66

```
Cys Gln Ser Tyr Asp Thr Asn Leu Ser Gly Trp Val
1               5                   10
```

<210> SEQ ID NO 67
<211> LENGTH: 112
<212> TYPE: PRT
<213> ORGANISM: Artificial Sequence
<220> FEATURE:
<223> OTHER INFORMATION: Synthetic Construct

<400> SEQUENCE: 67

```
Gln Ser Val Leu Thr Gln Pro Ser Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Gly Trp Val Phe Gly Gly Gly Thr Lys Leu Thr Val Leu Gly
            100                 105                 110
```

<210> SEQ ID NO 68
<211> LENGTH: 217
<212> TYPE: PRT
<213> ORGANISM: Artificial Sequence
<220> FEATURE:
<223> OTHER INFORMATION: Synthetic Construct

<400> SEQUENCE: 68

```
Gln Ser Val Leu Thr Gln Pro Ser Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Gly Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
```

```
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 69
<211> LENGTH: 19
<212> TYPE: PRT
<213> ORGANISM: Artificial Sequence
<220> FEATURE:
<223> OTHER INFORMATION: Synthetic Construct

<400> SEQUENCE: 69

Ser Tyr Ile Ser Ser Ser Ser Ser Tyr Thr Asp Tyr Ala Asp Thr Val
1               5                   10                  15

Lys Gly Arg


<210> SEQ ID NO 70
<211> LENGTH: 12
<212> TYPE: PRT
<213> ORGANISM: Artificial Sequence
<220> FEATURE:
<223> OTHER INFORMATION: Synthetic Construct

<400> SEQUENCE: 70

Ala Ser Tyr Ser Tyr Gly Arg Asp Ser Phe Asp Tyr
1               5                   10


<210> SEQ ID NO 71
<211> LENGTH: 112
<212> TYPE: PRT
<213> ORGANISM: Artificial Sequence
<220> FEATURE:
<223> OTHER INFORMATION: Synthetic Construct

<400> SEQUENCE: 71

Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Thr Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110


<210> SEQ ID NO 72
<211> LENGTH: 119
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Ser Tyr Thr Asp Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Tyr Ser Tyr Gly Arg Asp Ser Phe Asp Tyr Trp Gly Gln Gly
            100                 105                 110

Thr Leu Val Thr Val Ser Ser
        115
```

<210> SEQ ID NO 73
<211> LENGTH: 217
<212> TYPE: PRT
<213> ORGANISM: Artificial Sequence
<220> FEATURE:
<223> OTHER INFORMATION: Synthetic Construct

<400> SEQUENCE: 73

```
Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Thr Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 74
<211> LENGTH: 446
<212> TYPE: PRT
<213> ORGANISM: Artificial Sequence
<220> FEATURE:
<223> OTHER INFORMATION: Synthetic Construct

<400> SEQUENCE: 74

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Ser Tyr Thr Asp Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Tyr Ser Tyr Gly Arg Asp Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415
```

```
Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 75
<211> LENGTH: 112
<212> TYPE: PRT
<213> ORGANISM: Artificial Sequence
<220> FEATURE:
<223> OTHER INFORMATION: Synthetic Construct

<400> SEQUENCE: 75

Gln Ser Val Leu Thr Gln Pro Ala Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Gly Thr His Trp Tyr Gln Arg Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Gly Trp Val Phe Gly Gly Gly Thr Lys Leu Thr Val Leu Gly
            100                 105                 110


<210> SEQ ID NO 76
<211> LENGTH: 217
<212> TYPE: PRT
<213> ORGANISM: Artificial Sequence
<220> FEATURE:
<223> OTHER INFORMATION: Synthetic Construct

<400> SEQUENCE: 76

Gln Ser Val Leu Thr Gln Pro Ala Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Gly Thr His Trp Tyr Gln Arg Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Gly Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175
```

```
Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 77
<211> LENGTH: 14
<212> TYPE: PRT
<213> ORGANISM: Artificial Sequence
<220> FEATURE:
<223> OTHER INFORMATION: Synthetic Construct

<400> SEQUENCE: 77

Phe Arg Ser Asn Tyr Met Ser Trp Val Arg Gln Ala Pro Gly
1               5                   10


<210> SEQ ID NO 78
<211> LENGTH: 119
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

Thr Leu Val Thr Val Ser Ser
        115


<210> SEQ ID NO 79
<211> LENGTH: 446
<212> TYPE: PRT
<213> ORGANISM: Artificial Sequence
<220> FEATURE:
<223> OTHER INFORMATION: Synthetic Construct

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
```

-continued

```
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```

<210> SEQ ID NO 80
<211> LENGTH: 14
<212> TYPE: PRT
<213> ORGANISM: Artificial Sequence
<220> FEATURE:
<223> OTHER INFORMATION: Synthetic Construct

<400> SEQUENCE: 80

Cys Thr Gly Ser Thr Ser Asn Ile Gly Ala Gly Tyr Ala Thr
1               5                   10

<210> SEQ ID NO 81
<211> LENGTH: 19
<212> TYPE: PRT
<213> ORGANISM: Artificial Sequence
<220> FEATURE:
<223> OTHER INFORMATION: Synthetic Construct

<400> SEQUENCE: 81

Ser Tyr Ile Ser Ser Ser Ser Thr Tyr Ser Asp Tyr Ala Asp Ser Val
1               5                   10                  15

Lys Gly Arg

<210> SEQ ID NO 82
<211> LENGTH: 112
<212> TYPE: PRT
<213> ORGANISM: Artificial Sequence
<220> FEATURE:
<223> OTHER INFORMATION: Synthetic Construct

<400> SEQUENCE: 82

Gln Ser Val Leu Thr Gln Pro Ser Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Ala Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110

<210> SEQ ID NO 83
<211> LENGTH: 119
<212> TYPE: PRT
<213> ORGANISM: Artificial Sequence
<220> FEATURE:
<223> OTHER INFORMATION: Synthetic Construct

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Thr Ser Gly Phe Pro Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Ser Asp Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

```
Thr Leu Val Thr Val Ser Ser
        115


<210> SEQ ID NO 84
<211> LENGTH: 217
<212> TYPE: PRT
<213> ORGANISM: Artificial Sequence
<220> FEATURE:
<223> OTHER INFORMATION: Synthetic Construct

<400> SEQUENCE: 84

Gln Ser Val Leu Thr Gln Pro Ser Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Ala Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 85
<211> LENGTH: 446
<212> TYPE: PRT
<213> ORGANISM: Artificial Sequence
<220> FEATURE:
<223> OTHER INFORMATION: Synthetic Construct

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Thr Ser Gly Phe Pro Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Ser Asp Tyr Ala Asp Ser Val
    50                  55                  60

Lys Gly Arg Phe Ser Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```

<210> SEQ ID NO 86
<211> LENGTH: 112
<212> TYPE: PRT
<213> ORGANISM: Artificial Sequence
<220> FEATURE:
<223> OTHER INFORMATION: Synthetic Construct

<400> SEQUENCE: 86

```
Gln Ser Val Leu Thr Gln Pro Ser Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Val Ser Gly Leu
65                  70                  75                  80

Arg Ser Glu Asp Glu Ala Glu Tyr Tyr Cys Gln Ser Tyr Asp Thr Asn
                85                  90                  95

Leu Ser Gly Trp Val Phe Gly Gly Gly Thr Lys Leu Thr Val Leu Gly
            100                 105                 110


<210> SEQ ID NO 87
<211> LENGTH: 119
<212> TYPE: PRT
<213> ORGANISM: Artificial Sequence
<220> FEATURE:
<223> OTHER INFORMATION: Synthetic Construct

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Pro Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

Thr Leu Val Thr Val Ser Ser
        115


<210> SEQ ID NO 88
<211> LENGTH: 217
<212> TYPE: PRT
<213> ORGANISM: Artificial Sequence
<220> FEATURE:
<223> OTHER INFORMATION: Synthetic Construct

<400> SEQUENCE: 88

Gln Ser Val Leu Thr Gln Pro Ser Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Val Ser Gly Leu
65                  70                  75                  80
```

```
Arg Ser Glu Asp Glu Ala Glu Tyr Tyr Cys Gln Ser Tyr Asp Thr Asn
                85                  90                  95

Leu Ser Gly Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 89
<211> LENGTH: 446
<212> TYPE: PRT
<213> ORGANISM: Artificial Sequence
<220> FEATURE:
<223> OTHER INFORMATION: Synthetic Construct

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Pro Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
```

-continued

```
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 90
<211> LENGTH: 12
<212> TYPE: PRT
<213> ORGANISM: Artificial Sequence
<220> FEATURE:
<223> OTHER INFORMATION: Synthetic Construct

<400> SEQUENCE: 90

Cys Gln Ser Tyr Asp Thr Asn Leu Ser Ala Trp Val
1               5                   10


<210> SEQ ID NO 91
<211> LENGTH: 112
<212> TYPE: PRT
<213> ORGANISM: Artificial Sequence
<220> FEATURE:
<223> OTHER INFORMATION: Synthetic Construct

<400> SEQUENCE: 91

Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
```

-continued

```
                85                  90                  95

Leu Ser Ala Trp Val Phe Gly Gly Gly Thr Lys Leu Thr Val Leu Gly
            100                 105                 110


<210> SEQ ID NO 92
<211> LENGTH: 217
<212> TYPE: PRT
<213> ORGANISM: Artificial Sequence
<220> FEATURE:
<223> OTHER INFORMATION: Synthetic Construct

<400> SEQUENCE: 92

Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Ala Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 93
<211> LENGTH: 12
<212> TYPE: PRT
<213> ORGANISM: Artificial Sequence
<220> FEATURE:
<223> OTHER INFORMATION: Synthetic Construct

<400> SEQUENCE: 93

Ala Arg Tyr Ser Tyr Gly Arg Asp Asp Phe Asp Tyr
1               5                   10


<210> SEQ ID NO 94
<211> LENGTH: 112
<212> TYPE: PRT
<213> ORGANISM: Artificial Sequence
<220> FEATURE:
<223> OTHER INFORMATION: Synthetic Construct

<400> SEQUENCE: 94
```

Gln Ser Val Leu Thr Gln Pro Ala Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Asn Val Trp Val Phe Gly Gly Gly Thr Lys Leu Thr Val Leu Gly
            100                 105                 110

<210> SEQ ID NO 95
<211> LENGTH: 119
<212> TYPE: PRT
<213> ORGANISM: Artificial Sequence
<220> FEATURE:
<223> OTHER INFORMATION: Synthetic Construct

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asp Phe Asp Tyr Trp Gly Gln Gly
            100                 105                 110

Thr Leu Val Thr Val Ser Ser
        115

<210> SEQ ID NO 96
<211> LENGTH: 217
<212> TYPE: PRT
<213> ORGANISM: Artificial Sequence
<220> FEATURE:
<223> OTHER INFORMATION: Synthetic Construct

<400> SEQUENCE: 96

Gln Ser Val Leu Thr Gln Pro Ala Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

```
Arg Ser Glu Asp Glu Ala Asp Tyr Tyr Cys Gln Ser Tyr Asp Thr Asn
                85                  90                  95

Leu Asn Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 97
<211> LENGTH: 446
<212> TYPE: PRT
<213> ORGANISM: Artificial Sequence
<220> FEATURE:
<223> OTHER INFORMATION: Synthetic Construct

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asp Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
```

-continued

```
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 98
<211> LENGTH: 15
<212> TYPE: PRT
<213> ORGANISM: Artificial Sequence
<220> FEATURE:
<223> OTHER INFORMATION: Synthetic Construct

<400> SEQUENCE: 98

Cys Thr Gly Ser Thr Ser Asn Ile Gly Ala Gly Phe Asp Thr His
1               5                   10                  15


<210> SEQ ID NO 99
<211> LENGTH: 12
<212> TYPE: PRT
<213> ORGANISM: Artificial Sequence
<220> FEATURE:
<223> OTHER INFORMATION: Synthetic Construct

<400> SEQUENCE: 99

Ala Arg Tyr Ser Tyr Gly Arg Asp Ser Phe Asp Tyr
1               5                   10


<210> SEQ ID NO 100
<211> LENGTH: 112
<212> TYPE: PRT
<213> ORGANISM: Artificial Sequence
<220> FEATURE:
<223> OTHER INFORMATION: Synthetic Construct

<400> SEQUENCE: 100

Gln Ser Val Leu Thr Gln Pro Phe Ser Ala Ser Gly Thr Pro Gly Gln
1               5                   10                  15
```

```
Arg Val Thr Ile Ser Cys Thr Gly Ser Thr Ser Asn Ile Gly Ala Gly
            20                  25                  30

Phe Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Thr Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110


<210> SEQ ID NO 101
<211> LENGTH: 119
<212> TYPE: PRT
<213> ORGANISM: Artificial Sequence
<220> FEATURE:
<223> OTHER INFORMATION: Synthetic Construct

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Ser Phe Asp Tyr Trp Gly Gln Gly
            100                 105                 110

Thr Leu Val Thr Val Ser Ser
        115


<210> SEQ ID NO 102
<211> LENGTH: 217
<212> TYPE: PRT
<213> ORGANISM: Artificial Sequence
<220> FEATURE:
<223> OTHER INFORMATION: Synthetic Construct

<400> SEQUENCE: 102

Gln Ser Val Leu Thr Gln Pro Phe Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Phe Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Thr Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95
```

Leu Ser Val Trp Val Phe Gly Gly Gly Thr Lys Leu Thr Val Leu Gly
100 105 110

Gln Pro Lys Ala Ala Pro Ser Val Thr Leu Phe Pro Pro Ser Ser Glu
115 120 125

Glu Leu Gln Ala Asn Lys Ala Thr Leu Val Cys Leu Ile Ser Asp Phe
130 135 140

Tyr Pro Gly Ala Val Thr Val Ala Trp Lys Ala Asp Ser Ser Pro Val
145 150 155 160

Lys Ala Gly Val Glu Thr Thr Thr Pro Ser Lys Gln Ser Asn Asn Lys
165 170 175

Tyr Ala Ala Ser Ser Tyr Leu Ser Leu Thr Pro Glu Gln Trp Lys Ser
180 185 190

His Arg Ser Tyr Ser Cys Gln Val Thr His Glu Gly Ser Thr Val Glu
195 200 205

Lys Thr Val Ala Pro Thr Glu Cys Ser
210 215

<210> SEQ ID NO 103
<211> LENGTH: 446
<212> TYPE: PRT
<213> ORGANISM: Artificial Sequence
<220> FEATURE:
<223> OTHER INFORMATION: Synthetic Construct

<400> SEQUENCE: 103

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Asn
20 25 30

Tyr Met Ser Trp Val Arg Gln Ala Pro Gly Lys Gly Leu Glu Trp Val
35 40 45

Ser Tyr Ile Ser Ser Ser Ser Thr Tyr Thr Asp Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Ser Tyr Gly Arg Asp Ser Phe Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Cys Ser Arg Ser Thr Ser Glu Ser Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Lys Thr Tyr Thr Cys Asn Val Asp His Lys Pro
195 200 205

Ser Asn Thr Lys Val Asp Lys Arg Val Glu Ser Lys Tyr Gly Pro Pro
210 215 220

Cys Pro Pro Cys Pro Ala Pro Glu Phe Leu Gly Gly Pro Ser Val Phe
225 230 235 240

Leu Phe Pro Pro Lys Pro Lys Asp Thr Leu Met Ile Ser Arg Thr Pro

```
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 104
<211> LENGTH: 112
<212> TYPE: PRT
<213> ORGANISM: Artificial Sequence
<220> FEATURE:
<223> OTHER INFORMATION: Synthetic Construct

<400> SEQUENCE: 104

Gln Ser Val Leu Thr Gln Pro Ser Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Gly Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110


<210> SEQ ID NO 105
<211> LENGTH: 217
<212> TYPE: PRT
<213> ORGANISM: Artificial Sequence
<220> FEATURE:
<223> OTHER INFORMATION: Synthetic Construct

<400> SEQUENCE: 105

Gln Ser Val Leu Thr Gln Pro Ser Ser Ala Ser Gly Thr Pro Gly Gln
```

```
1               5                   10                  15

Arg Val Thr Ile Ser Cys Thr Gly Ser Thr Ser Asn Ile Gly Ala Gly
            20                  25                  30

Tyr Gly Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 106
<211> LENGTH: 112
<212> TYPE: PRT
<213> ORGANISM: Artificial Sequence
<220> FEATURE:
<223> OTHER INFORMATION: Synthetic Construct

<400> SEQUENCE: 106

Gln Ser Val Leu Thr Gln Pro Ser Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Pro
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Ala Trp Val Phe Gly Gly Gly Thr Lys Leu Thr Val Leu Gly
            100                 105                 110


<210> SEQ ID NO 107
<211> LENGTH: 217
<212> TYPE: PRT
<213> ORGANISM: Artificial Sequence
<220> FEATURE:
<223> OTHER INFORMATION: Synthetic Construct
```

<400> SEQUENCE: 107

```
Gln Ser Val Leu Thr Gln Pro Ser Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Pro
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Ala Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 108
<211> LENGTH: 112
<212> TYPE: PRT
<213> ORGANISM: Artificial Sequence
<220> FEATURE:
<223> OTHER INFORMATION: Synthetic Construct

<400> SEQUENCE: 108

```
Gln Ser Val Leu Thr Gln Pro Phe Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110
```

<210> SEQ ID NO 109
<211> LENGTH: 217
<212> TYPE: PRT
<213> ORGANISM: Artificial Sequence
<220> FEATURE:
<223> OTHER INFORMATION: Synthetic Construct

<400> SEQUENCE: 109

```
Gln Ser Val Leu Thr Gln Pro Phe Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 110
<211> LENGTH: 14
<212> TYPE: PRT
<213> ORGANISM: Artificial Sequence
<220> FEATURE:
<223> OTHER INFORMATION: Synthetic Construct

<400> SEQUENCE: 110

```
Phe Gly Ser Asn Tyr Met Ser Trp Val Arg Gln Ala Pro Gly
1               5                   10
```

<210> SEQ ID NO 111
<211> LENGTH: 112
<212> TYPE: PRT
<213> ORGANISM: Artificial Sequence
<220> FEATURE:
<223> OTHER INFORMATION: Synthetic Construct

<400> SEQUENCE: 111

```
Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
```

```
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Gly Trp Val Phe Gly Gly Gly Thr Lys Leu Thr Val Leu Gly
            100                 105                 110


<210> SEQ ID NO 112
<211> LENGTH: 119
<212> TYPE: PRT
<213> ORGANISM: Artificial Sequence
<220> FEATURE:
<223> OTHER INFORMATION: Synthetic Construct

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

Thr Leu Val Thr Val Ser Ser
        115


<210> SEQ ID NO 113
<211> LENGTH: 217
<212> TYPE: PRT
<213> ORGANISM: Artificial Sequence
<220> FEATURE:
<223> OTHER INFORMATION: Synthetic Construct

<400> SEQUENCE: 113

Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Gly Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
```

-continued

```
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 114
<211> LENGTH: 446
<212> TYPE: PRT
<213> ORGANISM: Artificial Sequence
<220> FEATURE:
<223> OTHER INFORMATION: Synthetic Construct

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285
```

```
Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 115
<211> LENGTH: 12
<212> TYPE: PRT
<213> ORGANISM: Artificial Sequence
<220> FEATURE:
<223> OTHER INFORMATION: Synthetic Construct

<400> SEQUENCE: 115

Ala Arg Tyr Ser Tyr Asp Arg Asp Asn Phe Asp Tyr
1               5                   10


<210> SEQ ID NO 116
<211> LENGTH: 112
<212> TYPE: PRT
<213> ORGANISM: Artificial Sequence
<220> FEATURE:
<223> OTHER INFORMATION: Synthetic Construct

<400> SEQUENCE: 116

Gln Ser Val Leu Thr Gln Pro Phe Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln His Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110


<210> SEQ ID NO 117
<211> LENGTH: 119
<212> TYPE: PRT
<213> ORGANISM: Artificial Sequence
```

```
<220> FEATURE:
<223> OTHER INFORMATION: Synthetic Construct

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Asp Arg Asp Asn Phe Asp Tyr Trp Gly Gln Gly
            100                 105                 110

Thr Leu Val Thr Val Ser Ser
        115


<210> SEQ ID NO 118
<211> LENGTH: 217
<212> TYPE: PRT
<213> ORGANISM: Artificial Sequence
<220> FEATURE:
<223> OTHER INFORMATION: Synthetic Construct

<400> SEQUENCE: 118

Gln Ser Val Leu Thr Gln Pro Phe Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln His Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 119
<211> LENGTH: 446
<212> TYPE: PRT
<213> ORGANISM: Artificial Sequence
<220> FEATURE:
<223> OTHER INFORMATION: Synthetic Construct

<400> SEQUENCE: 119

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Asp Arg Asp Asn Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365
```

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Arg Leu Thr Val Asp Lys Ser Arg Trp
405 410 415

Gln Glu Gly Asn Val Phe Ser Cys Ser Val Met His Glu Ala Leu His
420 425 430

Asn His Tyr Thr Gln Lys Ser Leu Ser Leu Ser Leu Gly Lys
435 440 445

<210> SEQ ID NO 120
<211> LENGTH: 19
<212> TYPE: PRT
<213> ORGANISM: Artificial Sequence
<220> FEATURE:
<223> OTHER INFORMATION: Synthetic Construct

<400> SEQUENCE: 120

Ser Tyr Ile Ser Ser Ser Ser Thr Tyr Ala Asp Tyr Ala Asp Ser Val
1 5 10 15

Lys Gly Arg

<210> SEQ ID NO 121
<211> LENGTH: 112
<212> TYPE: PRT
<213> ORGANISM: Artificial Sequence
<220> FEATURE:
<223> OTHER INFORMATION: Synthetic Construct

<400> SEQUENCE: 121

Gln Ser Val Leu Thr Gln Pro Ser Ser Ala Ser Gly Thr Pro Gly Gln
1 5 10 15

Arg Val Thr Ile Ser Cys Thr Gly Ser Thr Ser Asn Ile Gly Ala Gly
20 25 30

Tyr Asp Thr His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Ser Gly Leu
65 70 75 80

Arg Ser Glu Asp Glu Ala Asp Tyr Tyr Cys Gln Ser Tyr Asp Thr Asn
85 90 95

Leu Ser Ala Trp Val Phe Gly Gly Gly Thr Lys Leu Thr Val Leu Gly
100 105 110

<210> SEQ ID NO 122
<211> LENGTH: 119
<212> TYPE: PRT
<213> ORGANISM: Artificial Sequence
<220> FEATURE:
<223> OTHER INFORMATION: Synthetic Construct

<400> SEQUENCE: 122

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Asn
20 25 30

Tyr Met Ser Trp Val Arg Gln Ala Pro Gly Lys Gly Pro Glu Trp Val
35 40 45

```
Ser Tyr Ile Ser Ser Ser Ser Thr Tyr Ala Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

Thr Leu Val Thr Val Ser Ser
        115


<210> SEQ ID NO 123
<211> LENGTH: 217
<212> TYPE: PRT
<213> ORGANISM: Artificial Sequence
<220> FEATURE:
<223> OTHER INFORMATION: Synthetic Construct

<400> SEQUENCE: 123

Gln Ser Val Leu Thr Gln Pro Ser Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Ala Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 124
<211> LENGTH: 446
<212> TYPE: PRT
<213> ORGANISM: Artificial Sequence
<220> FEATURE:
<223> OTHER INFORMATION: Synthetic Construct

<400> SEQUENCE: 124

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Pro Glu Trp Val
        35                  40                  45

Ser Tyr Ile Ser Ser Ser Ser Thr Tyr Ala Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```

<210> SEQ ID NO 125
<211> LENGTH: 336
<212> TYPE: DNA
<213> ORGANISM: Artificial Sequence
<220> FEATURE:
<223> OTHER INFORMATION: Synthetic Construct

<400> SEQUENCE: 125
cagtctgtgc tgactcagcc accctcagcg tctgggaccc ccgggcagag ggtcaccatc 60
tcctgcactg ggagcacctc caacatcggg gcaggttatg acacacactg gtatcagcag 120
ctcccaggaa cggcccccaa actcctcatc tatggtaaca gcaatcggcc ctcaggggtc 180
cctgaccgat tctctggctc caagtctggc acctcagcct ccctggccat cagtgggctc 240
cggtccgagg atgaggctga ttattactgc cagtcctatg acaccggcct gagtgtttgg 300
gtgttcggcg gaggaaccaa gctgacggtc ctaggt 336

<210> SEQ ID NO 126
<211> LENGTH: 336
<212> TYPE: DNA
<213> ORGANISM: Artificial Sequence
<220> FEATURE:
<223> OTHER INFORMATION: Synthetic Construct

<400> SEQUENCE: 126
cagtctgtgc tgactcagcc accctcagcg tctgggaccc ccgggcagag ggtcaccatc 60
tcctgcactg ggagcacctc caacatcggg gcaggttatg acacacactg gtatcagcag 120
ctcccaggaa cggcccccaa actcctcatc tatggtaaca gcaatcggcc ctcaggggtc 180
cctgaccgat tctctggctc caagtctggc acctcagcct ccctggccat cagtgggctc 240
cggtccgagg atgaggctga ttattactgc cagtcctatg acacccagct gagtgtttgg 300
gtgttcggcg gaggaaccaa gctgacggtc ctaggt 336

<210> SEQ ID NO 127
<211> LENGTH: 336
<212> TYPE: DNA
<213> ORGANISM: Artificial Sequence
<220> FEATURE:
<223> OTHER INFORMATION: Synthetic Construct

<400> SEQUENCE: 127
cagtctgtgc tgactcagcc accctcagcg tctgggaccc ccgggcagag ggtcaccatc 60
tcctgcactg ggagcacctc caacatcggg gcaggttatg acacacactg gtatcagcag 120
ctcccaggaa cggcccccaa actcctcatc tatggtaaca gcaatcggcc ctcaggggtc 180
cctgaccgat tctctggctc caagtctggc acctcagcct ccctggccat cagtgggctc 240
cggtccgagg atgaggctga ttattactgc cagtcctatg acaccagcct gagtgtttgg 300
gtgttcggcg gaggaaccaa gctgacggtc ctaggt 336

<210> SEQ ID NO 128
<211> LENGTH: 336
<212> TYPE: DNA
<213> ORGANISM: Artificial Sequence
<220> FEATURE:
<223> OTHER INFORMATION: Synthetic Construct

<400> SEQUENCE: 128
cagtctgtgc tgactcagcc accctcagcg tctgggaccc ccgggcagag ggtcaccatc 60
tcctgcactg ggagcacctc caacatcggg gcaggttatg acacacactg gtatcagcag 120

```
ctcccaggaa cggcccccaa actcctcatc tatggtaaca gcaatcggcc ctcaggggtc    180

cctgaccgat tctctggctc caagtctggc acctcagcct ccctggccat cagtgggctc    240

cggtccgagg atgaggctga ttattactgc cagtcctatg acaccaacct ggccgtttgg    300

gtgttcggcg gaggaaccaa gctgacggtc ctaggt                              336
```

<210> SEQ ID NO 129
<211> LENGTH: 336
<212> TYPE: DNA
<213> ORGANISM: Artificial Sequence
<220> FEATURE:
<223> OTHER INFORMATION: Synthetic Construct

<400> SEQUENCE: 129

```
cagtctgtgc tgactcagcc accctcagcg tctgggaccc ccgggcagag ggtcaccatc     60

tcctgcactg ggagcacctc caacatcggg gcaggttatg acacacactg gtatcagcag    120

ctcccaggaa cggcccccaa actcctcatc tatggtaaca gcaatcggcc ctcaggggtc    180

cctgaccgat tctctggctc caagtctggc acctcagcct ccctggccat cagtgggctc    240

cggtccgagg atgaggctga ttattactgc cagtcctatg acaccaacct gggcgtttgg    300

gtgttcggcg gaggaaccaa gctgacggtc ctaggt                              336
```

<210> SEQ ID NO 130
<211> LENGTH: 336
<212> TYPE: DNA
<213> ORGANISM: Artificial Sequence
<220> FEATURE:
<223> OTHER INFORMATION: Synthetic Construct

<400> SEQUENCE: 130

```
cagtctgtgc tgactcagcc accctcagcg tctgggaccc ccgggcagag ggtcaccatc     60

tcctgcactg ggagcacctc caacatcggg gcaggttatg acacacactg gtatcagcag    120

ctcccaggaa cggcccccaa actcctcatc tatggtaaca gcaatcggcc ctcaggggtc    180

cctgaccgat tctctggctc caagtctggc acctcagcct ccctggccat cagtgggctc    240

cggtccgagg atgaggctga ttattactgc cagtcctatg acaccaacct gaacgtttgg    300

gtgttcggcg gaggaaccaa gctgacggtc ctaggt                              336
```

<210> SEQ ID NO 131
<211> LENGTH: 336
<212> TYPE: DNA
<213> ORGANISM: Artificial Sequence
<220> FEATURE:
<223> OTHER INFORMATION: Synthetic Construct

<400> SEQUENCE: 131

```
cagtctgtgc tgactcagcc attctcagcg tctgggaccc ccgggcagag ggtcaccatc     60

tcctgcactg ggagcacctc caacatcggg gcaggttatg acacacactg gtatcagcag    120

ctcccaggaa cggcccccaa actcctcatc tatggtaaca gcaatcggcc ctcaggggtc    180

cctgaccgat tctctggctc caagtctggc acctcagcct ccctggccat cagtgggctc    240

cggcccgagg atgaggctga ttattactgc cagtcctatg acaccagcct gagtgtttgg    300

gtgttcggcg gaggaaccaa gctgacggtc ctaggt                              336
```

<210> SEQ ID NO 132
<211> LENGTH: 357
<212> TYPE: DNA
<213> ORGANISM: Artificial Sequence
<220> FEATURE:
<223> OTHER INFORMATION: Synthetic Construct

<400> SEQUENCE: 132
gaggtgcagc tgttggagtc tgggggaggc ttggtacagc ctggggggtc cctgagactc 60
tcctgtgcag cctctggatt caccttcagt agcaactaca tgagctgggt ccgccaggct 120
ccagggaagg ggctggagtg ggtttcatac attagtagta gtagtactta cacagactac 180
gcagactctg tgaagggccg attcaccatc tccagagaca attccaagaa cacgctgtat 240
ctgcaaatga acagcctgag agccgaggac actgccgtgt attactgtgc gagatacagt 300
tatggccgcg acacttttga ctactggggc caaggtaccc tggtcaccgt gagctca 357

<210> SEQ ID NO 133
<211> LENGTH: 336
<212> TYPE: DNA
<213> ORGANISM: Artificial Sequence
<220> FEATURE:
<223> OTHER INFORMATION: Synthetic Construct

<400> SEQUENCE: 133
cagtctgtgc tgactcagcc accctcagcg tctgggaccc ccgggcagag ggtcaccatc 60
tcctgcactg ggagcacctc caacatcggg gcaggttatg gcacacactg gtatcagcgg 120
ctcccaggaa cggcccccaa actcctcatc tatggtaaca gcaatcggcc ctcaggggtc 180
cctgaccgat tctctggctc caagtctggc acctcagcct cccttgccat cagtgggctc 240
cggtccgagg atgaggctga ttattactgc cagtcctatg acaccaacct gagtgtttgg 300
gtgttcggcg gaggaaccaa gctgacggtc ctaggt 336

<210> SEQ ID NO 134
<211> LENGTH: 357
<212> TYPE: DNA
<213> ORGANISM: Artificial Sequence
<220> FEATURE:
<223> OTHER INFORMATION: Synthetic Construct

<400> SEQUENCE: 134
gaggtgcagc tgttggagtc tgggggaggc ttggtacagc ctggggggtc cctgagactc 60
tcctgtgcag cctctggatt caccttcagt agcaactaca tgagctgggt ccgccaggct 120
ccagggaagg ggctggagtg ggtttcatac attagtagta gtagtactta cacagactac 180
gcagactctg tgaagggccg attcaccatc tccagagaca attccaagaa cacgctgtat 240
ctgcaaatga acagcctgag agccgaggac actgccgtgt attactgtgc gagatacagt 300
tatagccgcg acaattttga ctactggggc caaggtaccc tggtcaccgt gagctca 357

<210> SEQ ID NO 135
<211> LENGTH: 336
<212> TYPE: DNA
<213> ORGANISM: Artificial Sequence
<220> FEATURE:
<223> OTHER INFORMATION: Synthetic Construct

<400> SEQUENCE: 135
cagtctgtgc tgactcagcc atcctcagcg tctgggaccc ccgggcagag ggtcaccatc 60
tcctgcactg ggagcacctc caacatcggg gcaggttatg acacacactg gtatcagcag 120
ctcccaggaa cggcccccaa actcctcatc tatggtaaca gcaatcggcc ctcaggggtc 180
cctgaccgat tctctggctc caagtctggc acctcagcct ccctggccat cagtgggctc 240
cggtccgagg atgaggctga ttattactgc cagtcctatg acaccaacct gagtggttgg 300

-continued gtgttcggcg gaggaaccaa gctgacggtc ctaggt 336

<210> SEQ ID NO 136
<211> LENGTH: 357
<212> TYPE: DNA
<213> ORGANISM: Artificial Sequence
<220> FEATURE:
<223> OTHER INFORMATION: Synthetic Construct

<400> SEQUENCE: 136
gaggtgcagc tgttggagtc tgggggaggc ttggtacagc ctggggggtc cctgagactc 60
tcctgtgcag cctctggatt caccttcagt agcaactaca tgagctgggt ccgccaggct 120
ccagggaagg ggctggagtg ggtttcatac attagtagta gtagtactta cacagactac 180
gcagactctg tgaagggccg attcaccatc tccagagaca attccaagaa cacgctgtat 240
ctgcaaatga acagcctgag agccgaggac actgccgtgt attactgtgc gagatacagt 300
tatggccgcg acaattttga ctactggggc caaggtaccc tggtcaccgt gagctca 357

<210> SEQ ID NO 137
<211> LENGTH: 336
<212> TYPE: DNA
<213> ORGANISM: Artificial Sequence
<220> FEATURE:
<223> OTHER INFORMATION: Synthetic Construct

<400> SEQUENCE: 137
cagtctgtgc tgactcagcc accctcagcg tctgggaccc ccgggcagag ggtcaccatc 60
tcctgcactg ggagcacctc caacatcggg gcaggttatg acacacactg gtatcagcag 120
ctcccaggaa cggcccccaa actcctcatc tatggtaaca gcaatcggcc ctcaggggtc 180
cctgaccgat tctctggctc caagtctggc acctcagcct ccctggccat cagtgggctc 240
cggaccgagg atgaggctga ttattactgc cagtcctatg acaccaacct gagtgtttgg 300
gtgttcggcg gaggaaccaa gctgacggtc ctaggt 336

<210> SEQ ID NO 138
<211> LENGTH: 357
<212> TYPE: DNA
<213> ORGANISM: Artificial Sequence
<220> FEATURE:
<223> OTHER INFORMATION: Synthetic Construct

<400> SEQUENCE: 138
gaggtgcagc tgttggagtc tgggggaggc ttggtacagc ctggggggtc cctgagactc 60
tcctgtgcag cctctggatt caccttcagt agcaactaca tgagctgggt ccgccaggct 120
ccagggaagg ggctggagtg ggtttcatac attagtagta gtagttctta cacagactac 180
gcagacactg tgaagggccg attcaccatc tccagagaca attccaagaa cacgctgtat 240
ctgcaaatga acagcctgag agccgaggac actgccgtgt attactgtgc gagttacagt 300
tatggccgcg acagttttga ctactggggc caaggtaccc tggtcaccgt gagctca 357

<210> SEQ ID NO 139
<211> LENGTH: 336
<212> TYPE: DNA
<213> ORGANISM: Artificial Sequence
<220> FEATURE:
<223> OTHER INFORMATION: Synthetic Construct

<400> SEQUENCE: 139
caatctgtgc tgactcagcc agcctcagcg tctgggaccc ccgggcagag ggtcaccatc 60
tcctgcactg ggagcacctc caacatcggg gcaggttatg gcacacactg gtatcagcgg 120
ctcccaggaa cggcccccaa actcctcatc tatggtaaca gcaatcggcc ctcaggggtc 180
cctgaccgat tctctggctc caagtctggc acctcagcct ccctggccat cagtgggctc 240
cggtccgagg atgaggctga ttattactgc cagtcctacg acaccaacct gagtggttgg 300
gtgttcggcg gaggaaccaa gctgacggtc ctaggt 336

<210> SEQ ID NO 140
<211> LENGTH: 357
<212> TYPE: DNA
<213> ORGANISM: Artificial Sequence
<220> FEATURE:
<223> OTHER INFORMATION: Synthetic Construct

<400> SEQUENCE: 140
gaggtgcagc tgttggagtc tgggggaggc ttggtacagc ctggggggtc cctgagactc 60
tcctgtgcag cctctggatt caccttcaga agcaactaca tgagctgggt ccgccaggct 120
ccagggaagg ggctggagtg ggtttcatac attagtagta gtagtactta cacagactac 180
gcagactctg tgaagggccg attcaccatc tccagagaca attccaagaa cacgctgtat 240
ctgcaaatga acagcctgag agccgaggac actgccgtgt attactgtgc gagatacagt 300
tatggccgcg acaattttga ctactggggc caaggtaccc tggtcaccgt gagctca 357

<210> SEQ ID NO 141
<211> LENGTH: 336
<212> TYPE: DNA
<213> ORGANISM: Artificial Sequence
<220> FEATURE:
<223> OTHER INFORMATION: Synthetic Construct

<400> SEQUENCE: 141
cagtctgtgc tgactcagcc atcctcagcg tctgggaccc ccgggcagag ggtcaccatc 60
tcctgcactg ggagcacctc caacatcggg gcaggttatg ccacacactg gtatcagcag 120
ctcccaggaa cggcccccaa actcctcatc tatggtaaca gcaatcggcc ctcaggggtc 180
cctgaccgat tctctggctc caagtctggc acctcagcct ccctggccat cagtgggctc 240
cggtccgagg atgaggctga ttattactgc cagtcctatg acaccaacct gagtgtttgg 300
gtgttcggcg gaggaaccaa gctgacggtc ctaggt 336

<210> SEQ ID NO 142
<211> LENGTH: 357
<212> TYPE: DNA
<213> ORGANISM: Artificial Sequence
<220> FEATURE:
<223> OTHER INFORMATION: Synthetic Construct

<400> SEQUENCE: 142
gaggtgcagc tgttggagtc tgggggaggc ttggtacagc ctggggggtc cctgagactc 60
tcctgtgcaa cctctggatt ccccttcagt agcaactaca tgagctgggt ccgccaggct 120
ccagggaagg ggctggagtg ggtttcatac attagtagta gtagtactta ctcagactac 180
gcagactctg tgaagggccg attctccatc tccagagaca attccaagaa cacactgtat 240
ctgcaaatga acagcctgag agccgaggac actgccgtgt attactgtgc gagatacagt 300
tatggccgcg acaattttga ctactggggc caaggtaccc tggtcaccgt gagctca 357

<210> SEQ ID NO 143
<211> LENGTH: 336

<212> TYPE: DNA
<213> ORGANISM: Artificial Sequence
<220> FEATURE:
<223> OTHER INFORMATION: Synthetic Construct

<400> SEQUENCE: 143
cagtctgtgc tgactcagcc atcctcagcg tctgggaccc ccgggcagag ggtcaccatc 60
tcctgcactg ggagcacctc caacatcggg gcaggttatg acacacactg gtaccagcag 120
ctcccaggaa cggcccccaa actcctcatc tatggtaaca gcaatcggcc ctcaggggtc 180
cctgaccgat tctctggctc caagtctggc acctcagcct ccctggccgt cagtgggctc 240
cggtccgagg atgaggctga atattactgc cagtcctatg acaccaacct gagtggttgg 300
gtgttcggcg gaggaaccaa gctgacggtc ctaggt 336

<210> SEQ ID NO 144
<211> LENGTH: 357
<212> TYPE: DNA
<213> ORGANISM: Artificial Sequence
<220> FEATURE:
<223> OTHER INFORMATION: Synthetic Construct

<400> SEQUENCE: 144
gaggtgcagc tgttggagtc tgggggaggc ttggtacagc ctggggggtc cctgagactc 60
tcctgtgcag cctctggatt caccttcagt agcaactaca tgagctgggt ccgccaggct 120
ccagggaagg ggccggagtg ggtttcatac attagtagta gtagtactta cacagactac 180
gcagactctg tgaagggccg attcaccatc tccagagaca attccaagaa cacgctgtat 240
ctgcaaatga acagcctgag agccgaggac actgccgtgt attactgtgc gagatacagt 300
tatggccgcg acaattttga ctactggggc caaggtaccc tggtcaccgt gagctca 357

<210> SEQ ID NO 145
<211> LENGTH: 336
<212> TYPE: DNA
<213> ORGANISM: Artificial Sequence
<220> FEATURE:
<223> OTHER INFORMATION: Synthetic Construct

<400> SEQUENCE: 145
cagtctgtgc tgactcagcc accctcagcg tctgggaccc ccgggcagag ggtcaccatc 60
tcctgcactg ggagcacctc caacatcggg gcaggttatg acacacactg gtatcagcag 120
ctcccaggaa cggcccccaa actcctcatc tatggtaaca gcaatcggcc ctcaggggtc 180
cctgaccgat tctctggctc caagtctggc acctcagcct ccctggccat cagtgggctc 240
cggtccgagg atgaggctga ttattactgc cagtcctatg acaccaacct gagtgcttgg 300
gtgttcggcg gaggaaccaa gctgacggtc ctaggt 336

<210> SEQ ID NO 146
<211> LENGTH: 336
<212> TYPE: DNA
<213> ORGANISM: Artificial Sequence
<220> FEATURE:
<223> OTHER INFORMATION: Synthetic Construct

<400> SEQUENCE: 146
cagtctgtgc tgactcagcc agcctcagcg tctgggaccc ccgggcagag ggtcaccatc 60
tcctgcactg ggagcacctc caacatcggg gcaggttatg acacacactg gtatcagcag 120
ctcccaggaa cggcccccaa actcctcatc tatggtaaca gcaatcggcc ctcaggggtc 180
cctgaccgat tctctggctc caagtctggc acctcagcct ccctggccat cagtgggctc 240
cggtccgagg atgaggctga ttattactgc cagtcctatg acaccaacct gaacgtttgg 300
gtgttcggcg gaggaaccaa gctgacggtc ctaggt 336

<210> SEQ ID NO 147
<211> LENGTH: 357
<212> TYPE: DNA
<213> ORGANISM: Artificial Sequence
<220> FEATURE:
<223> OTHER INFORMATION: Synthetic Construct

<400> SEQUENCE: 147
gaggtgcagc tgttggagtc tgggggaggc ttggtacagc ctggggggtc cctgaggctc 60
tcctgtgcag cctctggatt caccttcagt agcaactaca tgagctgggt ccgccaggct 120
ccagggaagg ggctggagtg ggtttcatac attagtagta gtagtactta cacagactac 180
gcagactctg tgaagggccg attcaccatc tccagagaca attccaagaa cacgctgtat 240
ctgcaaatga acagcctgag agccgaggac actgccgtgt attactgtgc gagatacagt 300
tatggccgcg acgattttga ctactggggc caaggtaccc tggtcaccgt gagctca 357

<210> SEQ ID NO 148
<211> LENGTH: 336
<212> TYPE: DNA
<213> ORGANISM: Artificial Sequence
<220> FEATURE:
<223> OTHER INFORMATION: Synthetic Construct

<400> SEQUENCE: 148
cagtctgtgc tgactcagcc attctcagcg tctgggaccc ccgggcagag ggtcaccatc 60
tcctgcactg ggagcacctc caacatcggg gcaggttttg acacacactg gtatcagcag 120
ctcccaggaa cggcccccaa actcctcatc tatggtaaca gcaatcggcc ctcaggggtc 180
cctgaccgat tctctggctc caagtctggc accacagcct ccctggccat cagtgggctc 240
cggtccgagg atgaggctga ttattactgc cagtcctatg acaccaacct gagtgtttgg 300
gtgttcggcg gaggaaccaa gctgacggtc ctaggt 336

<210> SEQ ID NO 149
<211> LENGTH: 357
<212> TYPE: DNA
<213> ORGANISM: Artificial Sequence
<220> FEATURE:
<223> OTHER INFORMATION: Synthetic Construct

<400> SEQUENCE: 149
gaggtgcagc tgttggagtc tgggggaggc ttggtacagc ctggggggtc cctgagactc 60
tcctgtgcag cctctggatt caccttcagt agcaactaca tgagctgggt ccgccaggct 120
ccagggaagg ggctggagtg ggtttcatac attagtagta gtagtactta cacagactac 180
gcagactctg tgaagggccg attcaccatc tccagagaca attccaagaa cacgctgtat 240
ctgcaaatga acagcctgag agccgaggac actgccgtgt attactgtgc gagatacagt 300
tatggccgcg acagttttga ctactggggc caaggtaccc tggtcaccgt gagctca 357

<210> SEQ ID NO 150
<211> LENGTH: 336
<212> TYPE: DNA
<213> ORGANISM: Artificial Sequence
<220> FEATURE:
<223> OTHER INFORMATION: Synthetic Construct

<400> SEQUENCE: 150

```
cagtctgtgc tgactcagcc atcctcagcg tctgggaccc ccgggcagag ggtcaccatc     60

tcctgcactg ggagcacctc caacatcggg gcaggttatg gcacacactg gtatcagcag    120

ctcccaggaa cggcccccaa actcctcatc tatggtaaca gcaatcggcc ctcaggggtc    180

cctgaccgat tctctggctc caagtctggc acctcagcct ccctggccat cagtgggctc    240

cggtccgagg atgaggctga ttattactgc cagtcctatg acaccaacct gagtgtttgg    300

gtgttcggcg gaggaaccaa gctgacggtc ctaggt                              336
```

<210> SEQ ID NO 151
<211> LENGTH: 336
<212> TYPE: DNA
<213> ORGANISM: Artificial Sequence
<220> FEATURE:
<223> OTHER INFORMATION: Synthetic Construct

<400> SEQUENCE: 151

```
cagtctgtgc tgactcagcc atcctcagcg tctgggaccc ccgggcagag ggtcaccatc     60

tcctgcactg ggagcacctc caacatcggg gcaggttatg acactcactg gtatcagcag    120

ctcccaggaa cggcccccaa acccctcatc tatggtaaca gcaatcggcc ctcaggggtc    180

cctgaccgat tctctggctc caagtctggc acctcagcct ccctggccat cagtgggctc    240

cggtccgagg atgaggctga ttattactgc cagtcctatg acaccaacct gagtgcttgg    300

gtgttcggcg gaggaaccaa gctgacggtc ctaggt                              336
```

<210> SEQ ID NO 152
<211> LENGTH: 357
<212> TYPE: DNA
<213> ORGANISM: Artificial Sequence
<220> FEATURE:
<223> OTHER INFORMATION: Synthetic Construct

<400> SEQUENCE: 152

```
gaggtgcagc tgttggagtc tgggggaggc ttggtacagc ctggggggtc cctgagactc     60

tcctgtgcag cctctggatt caccttcagt agcaactaca tgagctgggt ccgccaggcc    120

ccagggaagg ggctggagtg ggtttcatac attagtagta gtagtactta cacagactac    180

gctgactctg tgaagggccg attcaccatt tccagagaca attccaagaa cacgctgtat    240

ctgcaaatga acagcctgag agctgaggac actgccgtgt attactgtgc tagatacagt    300

tatggccgcg acaattttga ctactggggc caaggtaccc tggtcaccgt gagctca       357
```

<210> SEQ ID NO 153
<211> LENGTH: 336
<212> TYPE: DNA
<213> ORGANISM: Artificial Sequence
<220> FEATURE:
<223> OTHER INFORMATION: Synthetic Construct

<400> SEQUENCE: 153

```
cagtctgtgc tgactcagcc attctcagcg tctgggaccc ccgggcagag ggtcaccatc     60

tcctgcactg ggagcacctc caacatcggg gcaggttatg acacacactg gtatcagcag    120

ctcccaggaa cggcccccaa actcctcatc tatggtaaca gcaatcggcc ctcaggggtc    180

cctgaccgat tctctggctc caagtctggc acctcagcct ccctggccat cagtgggctc    240

cggtccgagg atgaggctga ttattactgc cagtcctatg acaccaacct gagtgtttgg    300

gtgttcggcg gaggaaccaa gctgacggtc ctaggt                              336
```

<210> SEQ ID NO 154
<211> LENGTH: 357
<212> TYPE: DNA
<213> ORGANISM: Artificial Sequence
<220> FEATURE:
<223> OTHER INFORMATION: Synthetic Construct

<400> SEQUENCE: 154
gaggtgcagc tgttggagtc tgggggaggc ttggtacagc ctggggggtc cctgagactc 60
tcctgtgcag cctctggatt caccttcagt agcaactaca tgagctgggt ccgccaggct 120
ccagggaagg ggctggagtg ggtttcatac attagtagta gtagcactta cacagactac 180
gcagactctg tgaagggccg attcaccatc tccagggaca attccaagaa cacgctgtat 240
ctgcaaatga acagcctgag agccgaggac actgccgtgt attactgtgc gagatacagt 300
tatggccgcg acacttttga ctactggggc caaggtaccc tggtcaccgt gagctca 357

<210> SEQ ID NO 155
<211> LENGTH: 336
<212> TYPE: DNA
<213> ORGANISM: Artificial Sequence
<220> FEATURE:
<223> OTHER INFORMATION: Synthetic Construct

<400> SEQUENCE: 155
cagtctgtgc tgactcagcc accctcagcg tctgggaccc ccgggcagag ggtcaccatc 60
tcctgcactg ggagcacctc caacatcggg gcaggttatg acacacactg gtatcagcag 120
ctcccaggaa cggcccccaa actcctcatc tatggtaaca gcaatcggcc ctcaggggtc 180
cctgaccgat tctctggctc caagtctggc acctcagcct ccctggccat cagtgggctc 240
cggtccgagg atgaggctga ttattactgc cagtcctatg acaccaacct gagtggttgg 300
gtgttcggcg gaggaaccaa gctgacggtc ctaggt 336

<210> SEQ ID NO 156
<211> LENGTH: 357
<212> TYPE: DNA
<213> ORGANISM: Artificial Sequence
<220> FEATURE:
<223> OTHER INFORMATION: Synthetic Construct

<400> SEQUENCE: 156
gaggtgcagc tgttggagtc tgggggaggc ttggtacagc ctggggggtc cctgagactc 60
tcctgtgcag cctctggatt caccttcggt agcaactaca tgagctgggt ccgccaggct 120
ccagggaagg ggctggagtg ggtttcatac attagtagta gtagtactta cacagactac 180
gcagactctg tgaagggccg attcaccatc tccagagaca attccaagaa cacgctgtat 240
ctgcaaatga acagcctgag agccgaggac actgccgtgt attactgtgc gagatacagt 300
tatggccgcg acaattttga ctactggggc caaggtaccc tggtcaccgt gagctca 357

<210> SEQ ID NO 157
<211> LENGTH: 336
<212> TYPE: DNA
<213> ORGANISM: Artificial Sequence
<220> FEATURE:
<223> OTHER INFORMATION: Synthetic Construct

<400> SEQUENCE: 157
cagtctgtgc tgactcagcc attctcagcg tctgggaccc ccgggcagag ggtcaccatc 60
tcctgcactg ggagcacctc caacatcggg gcaggttatg acacacactg gtatcagcat 120
ctcccaggaa cggcccccaa actcctcatc tatggtaaca gcaatcggcc ctcaggggtc 180
cctgaccgat tctctggctc caagtctggc acctcagcct ccctggccat cagtgggctc 240
cggtccgagg atgaggctga ttattactgc cagtcctatg acaccaacct gagtgtttgg 300
gtgttcggcg gaggaaccaa gctgacggtc ctaggt 336

<210> SEQ ID NO 158
<211> LENGTH: 357
<212> TYPE: DNA
<213> ORGANISM: Artificial Sequence
<220> FEATURE:
<223> OTHER INFORMATION: Synthetic Construct

<400> SEQUENCE: 158
gaggtgcagc tgttggagtc tgggggaggc ttggtacagc ctggggggtc cctgagactc 60
tcctgtgcag cctctggatt caccttcagt agcaactaca tgagctgggt ccgccaggct 120
ccagggaagg ggctggagtg ggtttcatac attagtagta gtagtactta cacagactac 180
gcagactctg tgaagggccg attcaccatc tccagagaca attccaagaa cacgctgtat 240
ctgcaaatga acagcctgag agccgaggac actgccgtgt attactgtgc gagatacagt 300
tatgaccgcg acaattttga ctactggggc caaggtaccc tggtcaccgt gagctca 357

<210> SEQ ID NO 159
<211> LENGTH: 336
<212> TYPE: DNA
<213> ORGANISM: Artificial Sequence
<220> FEATURE:
<223> OTHER INFORMATION: Synthetic Construct

<400> SEQUENCE: 159
cagtctgtgc tgactcagcc atcctcagcg tctgggaccc ccgggcagag ggtcaccatc 60
tcctgcactg ggagcacctc caacatcggg gcaggttatg acacacactg gtatcagcag 120
ctcccaggta cggcccccaa actcctcatc tatggtaaca gcaatcggcc ctcaggggtc 180
cctgaccgat tctctggctc caagtctggc acctcagcct ccctggccat cagtgggctc 240
cggtccgagg atgaggctga ttattactgc cagtcctatg acaccaacct gagtgcttgg 300
gtgttcggcg gaggaaccaa gctgacggtc ctaggt 336

<210> SEQ ID NO 160
<211> LENGTH: 357
<212> TYPE: DNA
<213> ORGANISM: Artificial Sequence
<220> FEATURE:
<223> OTHER INFORMATION: Synthetic Construct

<400> SEQUENCE: 160
gaggtgcagc tgttggagtc tgggggaggc ttggtacagc ctggggggtc cctgagactc 60
tcctgtgcgg cctctggatt caccttcagt agcaactaca tgagctgggt ccgccaggct 120
ccagggaagg ggccggagtg ggtttcatac attagtagta gtagtactta cgcagactac 180
gcagactctg tgaagggccg attcaccatc tccagagaca attccaagaa cacgctgtat 240
ctgcaaatga acagcctgag agccgaggac actgccgtgt attactgtgc gagatacagt 300
tatggccgcg acaattttga ctactggggc caaggtaccc tggtcaccgt gagctca 357

<210> SEQ ID NO 161
<211> LENGTH: 31
<212> TYPE: DNA
<213> ORGANISM: Artificial Sequence
<220> FEATURE:
<223> OTHER INFORMATION: Synthetic Primer

<400> SEQUENCE: 161
ggtggaattc ccaccatgta caggatgcaa c 31

<210> SEQ ID NO 162
<211> LENGTH: 35
<212> TYPE: DNA
<213> ORGANISM: Artificial Sequence
<220> FEATURE:
<223> OTHER INFORMATION: Synthetic Primer

<400> SEQUENCE: 162
tgcactcgag acggtgacca gtgtaccttg gcccc 35

<210> SEQ ID NO 163
<211> LENGTH: 651
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(651)

<400> SEQUENCE: 163

```
cag tct gtg ctg act cag cca ccc tca gcg tct ggg acc ccc ggg cag       48
Gln Ser Val Leu Thr Gln Pro Pro Ser Ala Ser Gly Thr Pro Gly Gln
1               5                   10                  15

agg gtc acc atc agc tgc act ggc agc acc tcc aac atc ggc gca ggt       96
Arg Val Thr Ile Ser Cys Thr Gly Ser Thr Ser Asn Ile Gly Ala Gly
            20                  25                  30

tat gac aca cac tgg tat cag cag ctc cca gga acg gcc ccc aag ctc      144
Tyr Asp Thr His Trp Tyr Gln Gln Leu Pro Gly Thr Ala Pro Lys Leu
        35                  40                  45

ctc atc tat ggt aac agc aat cgg ccc agc ggc gtc cct gac cga ttc      192
Leu Ile Tyr Gly Asn Ser Asn Arg Pro Ser Gly Val Pro Asp Arg Phe
    50                  55                  60

tct ggc tcc aag tct ggc acc tca gcc agc ctg gcc atc agt ggg ctc      240
Ser Gly Ser Lys Ser Gly Thr Ser Ala Ser Leu Ala Ile Ser Gly Leu
65                  70                  75                  80

cgg agc gag gat gag gct gat tat tac tgc cag tcc tat gac acc aac      288
Arg Ser Glu Asp Glu Ala Asp Tyr Tyr Cys Gln Ser Tyr Asp Thr Asn
                85                  90                  95

ctg agt gtt tgg gtg ttc ggc gga gga acc aag ctg acg gtc cta ggt      336
Leu Ser Val Trp Val Phe Gly Gly Gly Thr Lys Leu Thr Val Leu Gly
            100                 105                 110

cag ccc aag gct gcc ccc agc gtc act ctg ttc ccg ccc agc tct gag      384
Gln Pro Lys Ala Ala Pro Ser Val Thr Leu Phe Pro Pro Ser Ser Glu
        115                 120                 125

gag ctt caa gcc aac aag gcc aca ctg gtg tgt ctc ata agt gac ttc      432
Glu Leu Gln Ala Asn Lys Ala Thr Leu Val Cys Leu Ile Ser Asp Phe
    130                 135                 140

tac ccg gga gcc gtg aca gtg gcc tgg aag gca gat agc agc ccg gtc      480
Tyr Pro Gly Ala Val Thr Val Ala Trp Lys Ala Asp Ser Ser Pro Val
145                 150                 155                 160

aag gcg gga gtg gag acc acc aca ccc tcc aag caa agc aac aac aag      528
Lys Ala Gly Val Glu Thr Thr Thr Pro Ser Lys Gln Ser Asn Asn Lys
                165                 170                 175

tac gcg gcc agc agc tat ctg agc ctg acg cct gag cag tgg aag tcc      576
Tyr Ala Ala Ser Ser Tyr Leu Ser Leu Thr Pro Glu Gln Trp Lys Ser
            180                 185                 190

cac aga agc tac agc tgc cag gtc acg cat gaa ggg agc acc gtg gag      624
His Arg Ser Tyr Ser Cys Gln Val Thr His Glu Gly Ser Thr Val Glu
```

-continued

```
        195                 200                 205

aag aca gtg gcc ccg aca gaa tgt agc                                   651
Lys Thr Val Ala Pro Thr Glu Cys Ser
    210                 215


<210> SEQ ID NO 164
<211> LENGTH: 217
<212> TYPE: PRT
<213> ORGANISM: Artificial Sequence
<220> FEATURE:
<223> OTHER INFORMATION: Synthetic Construct

<400> SEQUENCE: 164

Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Asp Thr His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Asn
                85                  90                  95

Leu Ser Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 165
<211> LENGTH: 1347
<212> TYPE: DNA
<213> ORGANISM: Artificial Sequence
<220> FEATURE:
<223> OTHER INFORMATION: Synthetic Costruct
<220> FEATURE:
<221> NAME/KEY: CDS
<222> LOCATION: (1)..(1347)

<400> SEQUENCE: 165

gag gtg cag ctg ttg gag agc ggc gga ggc ttg gta cag cct ggc ggg        48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttc agt agc aac        96
Ser Leu Arg Leu Ser Cys Ala Ala Ser Gly Phe Thr Phe Ser Ser Asn
            20                  25                  30

tac atg agc tgg gtc cgc cag gct cca ggc aag ggg ctg gag tgg gtt       144
```

```
Tyr Met Ser Trp Val Arg Gln Ala Pro Gly Lys Gly Leu Glu Trp Val
        35                  40                  45

tca tac att agc tcc agt agc act tac aca gac tac gca gac tct gtg      192
Ser Tyr Ile Ser Ser Ser Ser Thr Tyr Thr Asp Tyr Ala Asp Ser Val
    50                  55                  60

aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac act gcc gtg tat tac tgt      288
Leu Gln Met Asn Ser Leu Arg Ala Glu Asp Thr Ala Val Tyr Tyr Cys
                85                  90                  95

gcg aga tac agc tat ggc cgc gac aac ttc gac tac tgg ggc caa ggt      336
Ala Arg Tyr Ser Tyr Gly Arg Asp Asn Phe Asp Tyr Trp Gly Gln Gly
            100                 105                 110

aca ctg gtc acc gtc tcg agt gct agc acc aag ggc cca tcg gtc ttc      384
Thr Leu Val Thr Val Ser Ser Ala Ser Thr Lys Gly Pro Ser Val Phe
        115                 120                 125

ccc ctg gca ccc tcc tcc aag agc acc tct ggg ggc aca gcg gcc ctg      432
Pro Leu Ala Pro Ser Ser Lys Ser Thr Ser Gly Gly Thr Ala Ala Leu
    130                 135                 140

ggc tgc ctg gtc aag gac tac ttc ccc gaa ccg gtg acg gtg tcg tgg      480
Gly Cys Leu Val Lys Asp Tyr Phe Pro Glu Pro Val Thr Val Ser Trp
145                 150                 155                 160

aac tca ggc gcc ctg acc agc ggc gtg cac acc ttc ccg gct gtc cta      528
Asn Ser Gly Ala Leu Thr Ser Gly Val His Thr Phe Pro Ala Val Leu
                165                 170                 175

cag tcc tca gga ctc tac tcc ctc agc agc gtg gtg acc gtg ccc tcc      576
Gln Ser Ser Gly Leu Tyr Ser Leu Ser Ser Val Val Thr Val Pro Ser
            180                 185                 190

agc agc ttg ggc acc cag acc tac atc tgc aac gtg aat cac aag ccc      624
Ser Ser Leu Gly Thr Gln Thr Tyr Ile Cys Asn Val Asn His Lys Pro
        195                 200                 205

agc aac acc aag gtg gac aag aaa gtt gag ccc aaa tct tgt gac aaa      672
Ser Asn Thr Lys Val Asp Lys Lys Val Glu Pro Lys Ser Cys Asp Lys
    210                 215                 220

act cac aca tgc cca ccg tgc cca gca cct gaa ctc ctg ggg gga ccg      720
Thr His Thr Cys Pro Pro Cys Pro Ala Pro Glu Leu Leu Gly Gly Pro
225                 230                 235                 240

tca gtc ttc ctc ttc ccc cca aaa ccc aag gac acc ctc atg atc tcc      768
Ser Val Phe Leu Phe Pro Pro Lys Pro Lys Asp Thr Leu Met Ile Ser
                245                 250                 255

cgg acc cct gag gtc aca tgc gtg gtg gtg gac gtg agc cac gaa gac      816
Arg Thr Pro Glu Val Thr Cys Val Val Val Asp Val Ser His Glu Asp
            260                 265                 270

cct gag gtc aag ttc aac tgg tac gtg gac ggc gtg gag gtg cat aat      864
Pro Glu Val Lys Phe Asn Trp Tyr Val Asp Gly Val Glu Val His Asn
        275                 280                 285

gcc aag aca aag ccg cgg gag gag cag tac aac agc acg tac cgt gtg      912
Ala Lys Thr Lys Pro Arg Glu Glu Gln Tyr Asn Ser Thr Tyr Arg Val
    290                 295                 300

gtc agc gtc ctc acc gtc ctg cac cag gac tgg ctg aat ggc aag gag      960
Val Ser Val Leu Thr Val Leu His Gln Asp Trp Leu Asn Gly Lys Glu
305                 310                 315                 320

tac aag tgc aag gtc tcc aac aaa gcc ctc cca gcc ccc atc gag aaa     1008
Tyr Lys Cys Lys Val Ser Asn Lys Ala Leu Pro Ala Pro Ile Glu Lys
                325                 330                 335

acc atc tcc aaa gcc aaa ggg cag ccc cga gaa cca cag gtg tac acc     1056
Thr Ile Ser Lys Ala Lys Gly Gln Pro Arg Glu Pro Gln Val Tyr Thr
            340                 345                 350

ctg ccc cca tcc cgg gag gag atg acc aag aac cag gtc agc ctg acc     1104
```

```
Leu Pro Pro Ser Arg Glu Glu Met Thr Lys Asn Gln Val Ser Leu Thr
        355                 360                 365

tgc ctg gtc aaa ggc ttc tat ccc agc gac atc gcc gtg gag tgg gag      1152
Cys Leu Val Lys Gly Phe Tyr Pro Ser Asp Ile Ala Val Glu Trp Glu
    370                 375                 380

agc aat ggg cag ccg gag aac aac tac aag acc acg cct ccc gtg ctg      1200
Ser Asn Gly Gln Pro Glu Asn Asn Tyr Lys Thr Thr Pro Pro Val Leu
385                 390                 395                 400

gac tcc gac ggc tcc ttc ttc ctc tac agc aag ctc acc gtg gac aag      1248
Asp Ser Asp Gly Ser Phe Phe Leu Tyr Ser Lys Leu Thr Val Asp Lys
                405                 410                 415

agc agg tgg cag cag ggg aac gtc ttc tca tgc tcc gtg atg cat gag      1296
Ser Arg Trp Gln Gln Gly Asn Val Phe Ser Cys Ser Val Met His Glu
            420                 425                 430

gct ctg cac aac cac tac acg cag aag agc ctc tcc ctg tct ccg ggt      1344
Ala Leu His Asn His Tyr Thr Gln Lys Ser Leu Ser Leu Ser Pro Gly
        435                 440                 445

aaa                                                                  1347
Lys


<210> SEQ ID NO 166
<211> LENGTH: 449
<212> TYPE: PRT
<213> ORGANISM: Artificial Sequence
<220> FEATURE:
<223> OTHER INFORMATION: Synthetic Construct

<400> SEQUENCE: 166

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Tyr Ile Ser Ser Ser Ser Thr Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Gly Arg Asp Asn Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

-continued

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

HUMAN MONOCLONAL ANTIBODY

CROSS-REFERENCES TO RELATED APPLICATIONS

This application is based on U.S. provisional patent applications No. 61/420,136 filed on Dec. 6, 2010, the contents of which are incorporated in full herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 234,640 bytes ASCII (Text) file named "709439SequenceListing.txt," created Dec. 5, 2011.

FIELD OF THE INVENTION

The present invention relates to a human monoclonal antibody molecule. Specifically, it relates to a human antibody molecule against human CD81 and a pharmaceutical composition containing the molecule as an active ingredient.

BACKGROUND OF THE INVENTION

Bowels are organs which digest and absorb nutrients and water essential for activities of life of organisms. Meanwhile, they are also organs which have an immunodefense performance for excluding foreign matters such as pathogens and keep life conservation by controlling contradictory qualities in a well-balanced manner. It is however known that when the balance of these functions becomes abnormal, this dynamic equilibrium is broken to induce various bowel diseases. Especially, inflammatory bowel diseases (abbreviated as IBD), of which patients have been increased in number in recent years, are associated with abnormalities in digestive organs such as abdominal pain, diarrhea, mucous and bloody stool and the like and, in view of pathogenic states thereof, grouped into ulcerative colitis and Crohn's disease.

Ulcerative colitis is a disease mainly showing diffuse bowel mucosal inflammation restricted to the large intestine, where repeated inflammation leads to the onset of colorectal cancer, surgery is often necessary, and postoperative problems of increased frequency of defecation, stool leakage and onset of pouchitis are caused. Crohn's disease is a disease showing lesion spreading from the small intestine to the large intestine, and intense, discontinuous all layer inflammation starting from the submucosal layer, where repeated inflammation leads to the intestinal complications (stenosis, fistula, abscess) that require operation (Inflamm. Bowel. Dis., 8, 244-250, 2002).

In recent years, it has been known that an anti-TNF-α antibody is effective as a therapeutic agent of Crohn's disease and ulcerative colitis (N. Engl. J. Med., 353, 2462-2476, 2005). Also, an anti-α4 integrin antibody Natalizumab has been reported to be effective as a therapeutic agent of Crohn's disease (J. Clin. Invest., 118, 825-826, 2008). Nevertheless, in the current therapies including the antibodies, 40-60% of IBD patients has not yet received a satisfactory medical treatment. Accordingly, the development of an effective therapeutic agent has been in high demand in a medical care (J. Clin. Gastroenterol., 41, 799-809, 2007).

CD81 is a cell surface molecule of 26 kDa, which is expressed in wide-ranging cells. It has an activity of decreasing a threshold of B cell activation by forming a complex with CD21, CD19 and Leu 13 in a B cell. In a T cell, it is associated with CD4 and CD8 to transduce stimulatory signal into cells. In view of these matters, CD81 is considered to have a significant role in an immune response to a heterologous antigen. Moreover, it is involved in various integrins physiologically and functionally to activate VLA-4 (α4β1 integrin) in a B cell or LFA-1 (αLβ2 integrin) in a thymocyte.

As a disease associated with CD81, hepatitis C is known (Science, 282, 938-941, 1998).

In recent years, it has been reported that anti-CD81 antibody is useful for the treatment of IBD (WO 2005/021792). IBD associated with T cell migration (J. Clin. Invest., 118, 825-826, 2008; Inflamm. Bowel Dis., 16(4), 583-92, 2010; J. Pharmacol. Exp. Ther., 327(2), 383-92, 2008). As other diseases associated with T cell migration, multiple sclerosis and psoriasis are known (J. Clin. Invest., 118, 825-826, 2008; J. Neuroimmunol., 60, 17-28, 1995; Expert Opinion on Biological Therapy, 3(2), 361-70, 2003).

To be specific, it has been reported that bowel mucosa layer T cells or peripheral blood T cells of a patient suffering from IBD such as Crohn's disease or ulcerative colitis highly express a chemokine receptor CXCR4 and exhibit a strong chemotactic response to a chemokine CXCL12 (Inflamm. Bowel Dis., 16(4), 583-92, 2010), and that colitis is cured by administering a CXCR4 inhibitor to an IBD model, dextran sulfate-induced mouse colitis model (J. Pharmacol. Exp. Ther., 327(2), 383-92, 2008), and that an anti-α-4 integrin antibody Natalizumab, which treats IBD by suppressing T cell migration, has been approved as a pharmaceutical product (*J. Clin. Invest.,* 118, 825-826, 2008).

It has also been reported that T cell migration is important for the pathology of an animal model of multiple sclerosis, experimental autoimmune encephalomyelitis (EAE) mouse (J. Neuroimmunol., 60, 17-28, 1995). Natalizumab is thought to exert its therapeutic efficacy by blocking the α4 integrin-mediated adhesion of circulating T cells to the blood-brain barrier in EAE mice (*J. Clin. Invest.,* 118, 825-826, 2008). Natalizumab is also effective for the treatment of multiple sclerosis.

Furthermore, it has been reported that T cells abundantly accumulate in psoriatic skin and that an anti-LFA-1 antibody Efalizumab (trade name: Raptiva), which suppresses T cell migration, is effective for the treatment of psoriasis (Expert Opinion on Biological Therapy, 3(2), 361-70, 2003).

There arise various problems based on the species difference when clinical application of an anti-CD81 antibody to human is desired. For example, administration of a mouse antibody to human may be limited by short serum half-life, failure to trigger certain kinds of human effector function and induction of undesirable human immune response to the mouse antibody ("human anti-mouse antibody" (HAMA) reaction) (Blood, 62, 988-995, 1983; Cancer Res., 45, 879-885, 1985). Moreover, even an anti-TNFα antibody (Remicade), which is a chimeric molecule obtained by binding the variable (V) region of a rodent antibody with the constant (C) region of a human antibody, may induce a human anti-chimeric antibody (HACA) and cause an infusion reaction or loss of drug efficacy (Current Gastroenterology Reports, 5(6), 501-5, 2003).

SUMMARY OF THE INVENTION

Under the circumstances, an anti-CD81 antibody that can be used as a pharmaceutical product is desired. However, such antibody is not known, and therefore, the problem to be solved by the present invention is provision of an anti-CD81 antibody usable as a pharmaceutical product for human.

In an attempt to solve the above-mentioned problem, the present inventors have prepared fully human anti-CD81 antibodies from a human complementarity-determining region (CDR) library by a phage library method, evaluated the region of human CD81 to which the antibodies bind, and found that antibodies bound to a certain region of CD81 show superior efficacy as well as high safety for human body, which resulted in the completion of the present invention. The present invention provides a human monoclonal antibody to human CD81. Furthermore, the present inventors obtained new findings that the anti-CD81 antibodies suppressed T cell migration, which revealed that the antibody of the present invention was useful for the prophylaxis, improvement or treatment of not only inflammatory bowel diseases such as Crohn's disease and ulcerative colitis but also diseases associated with T cell migration such as multiple sclerosis and psoriasis. Furthermore, the present inventors found that the antibody of the present invention is not only capable of merely binding to CD81-expressing cancer cells, but also has a cytotoxic effect, due to its complement-dependent cytotoxicity (CDC), on cancer cells to which it has bound, and is therefore also useful in preventing, ameliorating or treating cancers caused by CD81-expressing cancer cells, including hematological cancers (hematologic cancers, blood cancers, hematologic(al) malignancies).

Accordingly, the present invention is as follows.

[1] An anti-human CD81 antibody capable of binding to a peptide region consisting of the amino acid sequence of the amino acid numbers 80 to 175 in the amino acid sequence shown in SEQ ID NO:22.

[2] The antibody of [1], wherein the peptide region consists of the amino acid sequence of the amino acid numbers 113 to 175.

[3] The antibody of [1] or [2], wherein the binding affinity of the antibody to at least one human CD81 variant selected from the group consisting of the following (1) to (13) is less than 40% of that to the human CD81 having the amino acid sequence shown in SEQ ID NO:22.

(1) CD81 variant having the amino acid sequence shown in SEQ ID NO:22 wherein tyrosine at the amino acid number 127 is substituted with phenylalanine or tryptophan;

(2) CD81 variant having the amino acid sequence shown in SEQ ID NO:22 wherein alanine at the amino acid number 130 is substituted with threonine or valine;

(3) CD81 variant having the amino acid sequence shown in SEQ ID NO:22 wherein valine at the amino acid number 135 is substituted with alanine or leucine;

(4) CD81 variant having the amino acid sequence shown in SEQ ID NO:22 wherein aspartic acid at the amino acid number 137 is substituted with alanine or glutamic acid;

(5) CD81 variant having the amino acid sequence shown in SEQ ID NO:22 wherein alanine at the amino acid number 143 is substituted with threonine or valine;

(6) CD81 variant having the amino acid sequence shown in SEQ ID NO:22 wherein histidine at the amino acid number 151 is substituted with alanine or arginine;

(7) CD81 variant having the amino acid sequence shown in SEQ ID NO:22 wherein leucine at the amino acid number 154 is substituted with alanine or isoleucine;

(8) CD81 variant having the amino acid sequence shown in SEQ ID NO:22 wherein glycine at the amino acid number 158 is substituted with alanine or serine;

(9) CD81 variant having the amino acid sequence shown in SEQ ID NO:22 wherein alanine at the amino acid number 164 is substituted with threonine or valine;

(10) CD81 variant having the amino acid sequence shown in SEQ ID NO:22 wherein serine at the amino acid number 168 is substituted with alanine or threonine;

(11) CD81 variant having the amino acid sequence shown in SEQ ID NO:22 wherein valine at the amino acid number 169 is substituted with alanine or leucine;

(12) CD81 variant having the amino acid sequence shown in SEQ ID NO:22 wherein leucine at the amino acid number 170 is substituted with alanine or isoleucine; and

(13) CD81 variant having the amino acid sequence shown in SEQ ID NO:22 wherein asparagine at the amino acid number 172 is substituted with alanine or glutamine.

[4] The antibody of any one of [1] to [3], wherein the binding affinity of the antibody to each of the above-identified human CD81 variants (9) and (11) is less than 40% of that to the human CD81 having the amino acid sequence shown in SEQ ID NO:22.

[5] An antibody having a binding property equivalent to that of the antibody of any one of [1] to [4], or binding to the human CD81 having the amino acid sequence shown in SEQ ID NO:22 competitively with the antibody of any one of [1] to [4].

[6] An antibody binding to the human CD81 having the amino acid sequence shown in SEQ ID NO:22 competitively with the antibody of any one of [1] to [4], and having a suppressive effect of T cell migration.

[7] An anti-human CD81 antibody, which comprises all 6 CDRs described in any one of the following groups 1 to 24.

Group 1

(a-1) a CDR comprising the amino acid sequence shown in SEQ ID NO:1, (b-1) a CDR comprising the amino acid sequence shown in SEQ ID NO:2, (c-1) a CDR comprising the amino acid sequence shown in SEQ ID NO:3, (d-1) a CDR comprising the amino acid sequence shown in SEQ ID NO:4, (e-1) a CDR comprising the amino acid sequence shown in SEQ ID NO:5, and (f-1) a CDR comprising the amino acid sequence shown in SEQ ID NO:6

Group 2

(a-2) a CDR comprising the amino acid sequence shown in SEQ ID NO:1, (b-2) a CDR comprising the amino acid sequence shown in SEQ ID NO:2, (c-2) a CDR comprising the amino acid sequence shown in SEQ ID NO:37, (d-2) a CDR comprising the amino acid sequence shown in SEQ ID NO:4, (e-2) a CDR comprising the amino acid sequence shown in SEQ ID NO:5, and (f-2) a CDR comprising the amino acid sequence shown in SEQ ID NO: 6

Group 3

(a-3) a CDR comprising the amino acid sequence shown in SEQ ID NO:1, (b-3) a CDR comprising the amino acid sequence shown in SEQ ID NO:2, (c-3) a CDR comprising the amino acid sequence shown in SEQ ID NO:40, (d-3) a CDR comprising the amino acid sequence shown in SEQ ID NO:4, (e-3) a CDR comprising the amino acid sequence shown in SEQ ID NO:5, and (f-3) a CDR comprising the amino acid sequence shown in SEQ ID NO: 6

Group 4

(a-4) a CDR comprising the amino acid sequence shown in SEQ ID NO:1, (b-4) a CDR comprising the amino acid sequence shown in SEQ ID NO:2, (c-4) a CDR comprising the amino acid sequence shown in SEQ ID NO:43, (d-4) a CDR comprising the amino acid sequence shown in SEQ ID NO:4, (e-4) a CDR comprising the amino acid sequence shown in SEQ ID NO:5, and (f-4) a CDR comprising the amino acid sequence shown in SEQ ID NO:6

Group 5

(a-5) a CDR comprising the amino acid sequence shown in SEQ ID NO:1, (b-5) a CDR comprising the amino acid sequence shown in SEQ ID NO:2, (c-5) a CDR comprising the amino acid sequence shown in SEQ ID NO:46, (d-5) a CDR comprising the amino acid sequence shown in SEQ ID NO:4, (e-5) a CDR comprising the amino acid sequence shown in SEQ ID NO:5, and (f-5) a CDR comprising the amino acid sequence shown in SEQ ID NO:6

Group 6

(a-6) a CDR comprising the amino acid sequence shown in SEQ ID NO:1, (b-6) a CDR comprising the amino acid sequence shown in SEQ ID NO:2, (c-6) a CDR comprising the amino acid sequence shown in SEQ ID NO:49, (d-6) a CDR comprising the amino acid sequence shown in SEQ ID NO:4, (e-6) a CDR comprising the amino acid sequence shown in SEQ ID NO:5, and (f-6) a CDR comprising the amino acid sequence shown in SEQ ID NO:6

Group 7

(a-7) a CDR comprising the amino acid sequence shown in SEQ ID NO:1, (b-7) a CDR comprising the amino acid sequence shown in SEQ ID NO: 2, (c-7) a CDR comprising the amino acid sequence shown in SEQ ID NO:52, (d-7) a CDR comprising the amino acid sequence shown in SEQ ID NO: 4, (e-7) a CDR comprising the amino acid sequence shown in SEQ ID NO:5, and (f-7) a CDR comprising the amino acid sequence shown in SEQ ID NO:6

Group 8

(a-8) a CDR comprising the amino acid sequence shown in SEQ ID NO:1, (b-8) a CDR comprising the amino acid sequence shown in SEQ ID NO:2, (c-8) a CDR comprising the amino acid sequence shown in SEQ ID NO:43, (d-8) a CDR comprising the amino acid sequence shown in SEQ ID NO:4, (e-8) a CDR comprising the amino acid sequence shown in SEQ ID NO:5, and (f-8) a CDR comprising the amino acid sequence shown in SEQ ID NO:55

Group 9

(a-9) a CDR comprising the amino acid sequence shown in SEQ ID NO:60, (b-9) a CDR comprising the amino acid sequence shown in SEQ ID NO:2, (c-9) a CDR comprising the amino acid sequence shown in SEQ ID NO:3, (d-9) a CDR comprising the amino acid sequence shown in SEQ ID NO:4, (e-9) a CDR comprising the amino acid sequence shown in SEQ ID NO:5, and (f-9) a CDR comprising the amino acid sequence shown in SEQ ID NO:61

Group 10

(a-10) a CDR comprising the amino acid sequence shown in SEQ ID NO:1, (b-10) a CDR comprising the amino acid sequence shown in SEQ ID NO:2, (c-10) a CDR comprising the amino acid sequence shown in SEQ ID NO:66, (d-10) a CDR comprising the amino acid sequence shown in SEQ ID NO:4, (e-10) a CDR comprising the amino acid sequence shown in SEQ ID NO:5, and (f-10) a CDR comprising the amino acid sequence shown in SEQ ID NO:6

Group 11

(a-11) a CDR comprising the amino acid sequence shown in SEQ ID NO:1, (b-11) a CDR comprising the amino acid sequence shown in SEQ ID NO:2, (c-11) a CDR comprising the amino acid sequence shown in SEQ ID NO:3, (d-11) a CDR comprising the amino acid sequence shown in SEQ ID NO:4, (e-11) a CDR comprising the amino acid sequence shown in SEQ ID NO:69, and (f-11) a CDR comprising the amino acid sequence shown in SEQ ID NO:70

Group 12

(a-12) a CDR comprising the amino acid sequence shown in SEQ ID NO: 60, (b-12) a CDR comprising the amino acid sequence shown in SEQ ID NO:2, (c-12) a CDR comprising the amino acid sequence shown in SEQ ID NO:66, (d-12) a CDR comprising the amino acid sequence shown in SEQ ID NO:4, (e-12) a CDR comprising the amino acid sequence shown in SEQ ID NO:5, and (f-12) a CDR comprising the amino acid sequence shown in SEQ ID NO:6

Group 13

(a-13) a CDR comprising the amino acid sequence shown in SEQ ID NO:1, (b-13) a CDR comprising the amino acid sequence shown in SEQ ID NO:2, (c-13) a CDR comprising the amino acid sequence shown in SEQ ID NO:3, (d-13) a CDR comprising the amino acid sequence shown in SEQ ID NO:77, (e-13) a CDR comprising the amino acid sequence shown in SEQ ID NO:5, and (f-13) a CDR comprising the amino acid sequence shown in SEQ ID NO:6

Group 14
(a-14) a CDR comprising the amino acid sequence shown in SEQ ID NO:80,
(b-14) a CDR comprising the amino acid sequence shown in SEQ ID NO:2,
(c-14) a CDR comprising the amino acid sequence shown in SEQ ID NO:3,
(d-14) a CDR comprising the amino acid sequence shown in SEQ ID NO:4,
(e-14) a CDR comprising the amino acid sequence shown in SEQ ID NO:81, and
(f-14) a CDR comprising the amino acid sequence shown in SEQ ID NO:6

Group 15
(a-15) a CDR comprising the amino acid sequence shown in SEQ ID NO:1,
(b-15) a CDR comprising the amino acid sequence shown in SEQ ID NO:2,
(c-15) a CDR comprising the amino acid sequence shown in SEQ ID NO: 66,
(d-15) a CDR comprising the amino acid sequence shown in SEQ ID NO:4,
(e-15) a CDR comprising the amino acid sequence shown in SEQ ID NO:5, and
(f-15) a CDR comprising the amino acid sequence shown in SEQ ID NO:6

Group 16
(a-16) a CDR comprising the amino acid sequence shown in SEQ ID NO:1,
(b-16) a CDR comprising the amino acid sequence shown in SEQ ID NO:2,
(c-16) a CDR comprising the amino acid sequence shown in SEQ ID NO:90,
(d-16) a CDR comprising the amino acid sequence shown in SEQ ID NO:4,
(e-16) a CDR comprising the amino acid sequence shown in SEQ ID NO:5, and
(f-16) a CDR comprising the amino acid sequence shown in SEQ ID NO:6

Group 17
(a-17) a CDR comprising the amino acid sequence shown in SEQ ID NO:1,
(b-17) a CDR comprising the amino acid sequence shown in SEQ ID NO:2,
(c-17) a CDR comprising the amino acid sequence shown in SEQ ID NO:52,
(d-17) a CDR comprising the amino acid sequence shown in SEQ ID NO:4,
(e-17) a CDR comprising the amino acid sequence shown in SEQ ID NO:5, and
(f-17) a CDR comprising the amino acid sequence shown in SEQ ID NO:93

Group 18
(a-18) a CDR comprising the amino acid sequence shown in SEQ ID NO:98,
(b-18) a CDR comprising the amino acid sequence shown in SEQ ID NO:2,
(c-18) a CDR comprising the amino acid sequence shown in SEQ ID NO:3,
(d-18) a CDR comprising the amino acid sequence shown in SEQ ID NO:4,
(e-18) a CDR comprising the amino acid sequence shown in SEQ ID NO:5, and
(f-18) a CDR comprising the amino acid sequence shown in SEQ ID NO:99

Group 19
(a-19) a CDR comprising the amino acid sequence shown in SEQ ID NO: 60,
(b-19) a CDR comprising the amino acid sequence shown in SEQ ID NO:2,
(c-19) a CDR comprising the amino acid sequence shown in SEQ ID NO:3,
(d-19) a CDR comprising the amino acid sequence shown in SEQ ID NO:4,
(e-19) a CDR comprising the amino acid sequence shown in SEQ ID NO:5, and
(f-19) a CDR comprising the amino acid sequence shown in SEQ ID NO:99

Group 20
(a-20) a CDR comprising the amino acid sequence shown in SEQ ID NO:1,
(b-20) a CDR comprising the amino acid sequence shown in SEQ ID NO:2,
(c-20) a CDR comprising the amino acid sequence shown in SEQ ID NO:90,
(d-20) a CDR comprising the amino acid sequence shown in SEQ ID NO:4,
(e-20) a CDR comprising the amino acid sequence shown in SEQ ID NO:5, and
(f-20) a CDR comprising the amino acid sequence shown in SEQ ID NO:6

Group 21
(a-21) a CDR comprising the amino acid sequence shown in SEQ ID NO:1,
(b-21) a CDR comprising the amino acid sequence shown in SEQ ID NO:2,
(c-21) a CDR comprising the amino acid sequence shown in SEQ ID NO:3,
(d-21) a CDR comprising the amino acid sequence shown in SEQ ID NO:4,
(e-21) a CDR comprising the amino acid sequence shown in SEQ ID NO:5, and
(f-21) a CDR comprising the amino acid sequence shown in SEQ ID NO:55

Group 22
(a-22) a CDR comprising the amino acid sequence shown in SEQ ID NO:1,
(b-22) a CDR comprising the amino acid sequence shown in SEQ ID NO:2,
(c-22) a CDR comprising the amino acid sequence shown in SEQ ID NO:66,
(d-22) a CDR comprising the amino acid sequence shown in SEQ ID NO:110,
(e-22) a CDR comprising the amino acid sequence shown in SEQ ID NO:5, and
(f-22) a CDR comprising the amino acid sequence shown in SEQ ID NO:6

Group 23
(a-23) a CDR comprising the amino acid sequence shown in SEQ ID NO: 1,
(b-23) a CDR comprising the amino acid sequence shown in SEQ ID NO:2,
(c-23) a CDR comprising the amino acid sequence shown in SEQ ID NO:3,
(d-23) a CDR comprising the amino acid sequence shown in SEQ ID NO:4,
(e-23) a CDR comprising the amino acid sequence shown in SEQ ID NO:5, and
(f-23) a CDR comprising the amino acid sequence shown in SEQ ID NO:115

Group 24
(a-24) a CDR comprising the amino acid sequence shown in SEQ ID NO:1,
(b-24) a CDR comprising the amino acid sequence shown in SEQ ID NO:2,
(c-24) a CDR comprising the amino acid sequence shown in SEQ ID
(d-24) a CDR comprising the amino acid sequence shown in SEQ ID NO:4,
(e-24) a CDR comprising the amino acid sequence shown in SEQ ID NO:120, and
(f-24) a CDR comprising the amino acid sequence shown in SEQ ID NO:6.

[8] The antibody of [7], which comprises the combination of the light chain variable region and the heavy chain variable region described in any one of the following groups 25 to 48.

Group 25
(g-1) a light chain variable region comprising the above-identified CDRs (a-1) to (c-1); and
(h-1) a heavy chain variable region comprising the above-identified CDRs (d-1) to (f-1),
Group 26
(g-2) a light chain variable region comprising the above-identified CDRs (a-2) to (c-2); and
(h-2) a heavy chain variable region comprising the above-identified CDRs (d-2) to (f-2),
Group 27
(g-3) a light chain variable region comprising the above-identified CDRs (a-3) to (c-3); and
(h-3) a heavy chain variable region comprising the above-identified CDRs (d-3) to (f-3),
Group 28
(g-4) a light chain variable region comprising the above-identified CDRs (a-4) to (c-4); and
(h-4) a heavy chain variable region comprising the above-identified CDRs (d-4) to (f-4),
Group 29
(g-5) a light chain variable region comprising the above-identified CDRs (a-5) to (c-5); and
(h-5) a heavy chain variable region comprising the above-identified CDRs (d-5) to (f-5),
Group 30
(g-6) a light chain variable region comprising the above-identified CDRs (a-6) to (c-6); and
(h-6) a heavy chain variable region comprising the above-identified CDRs (d-6) to (f-6),
Group 31
(g-7) a light chain variable region comprising the above-identified CDRs (a-7) to (c-7); and
(h-7) a heavy chain variable region comprising the above-identified CDRs (d-7) to (f-7),
Group 32
(g-8) a light chain variable region comprising the above-identified CDRs (a-8) to (c-8); and
(h-8) a heavy chain variable region comprising the above-identified CDRs (d-8) to (f-8),
Group 33
(g-9) a light chain variable region comprising the above-identified CDRs (a-9) to (c-9); and
(h-9) a heavy chain variable region comprising the above-identified CDRs (d-9) to (f-9),
Group 34
(g-10) a light chain variable region comprising the above-identified CDRs (a-10) to (c-10); and
(h-10) a heavy chain variable region comprising the above-identified CDRs (d-10) to (f-10),
Group 35
(g-11) a light chain variable region comprising the above-identified CDRs (a-11) to (c-11); and
(h-11) a heavy chain variable region comprising the above-identified CDRs (d-11) to (f-11),
Group 36
(g-12) a light chain variable region comprising the above-identified CDRs (a-12) to (c-12); and
(h-12) a heavy chain variable region comprising the above-identified CDRs (d-12) to (f-12),
Group 37
(g-13) a light chain variable region comprising the above-identified CDRs (a-13) to (c-13); and
(h-13) a heavy chain variable region comprising the above-identified CDRs (d-13) to (f-13),
Group 38
(g-14) a light chain variable region comprising the above-identified CDRs (a-14) to (c-14); and
(h-14) a heavy chain variable region comprising the above-identified CDRs (d-14) to (f-14),
Group 39
(g-15) a light chain variable region comprising the above-identified CDRs (a-15) to (c-15); and
(h-15) a heavy chain variable region comprising the above-identified CDRs (d-15) to (f-15),
Group 40
(g-16) a light chain variable region comprising the above-identified CDRs (a-16) to (c-16); and
(h-16) a heavy chain variable region comprising the above-identified CDRs (d-16) to (f-16),
Group 41
(g-17) a light chain variable region comprising the above-identified CDRs (a-17) to (c-17); and
(h-17) a heavy chain variable region comprising the above-identified CDRs (d-17) to (f-17),
Group 42
(g-18) a light chain variable region comprising the above-identified CDRs (a-18) to (c-18); and
(h-18) a heavy chain variable region comprising the above-identified CDRs (d-18) to (f-18),
Group 43
(g-19) a light chain variable region comprising the above-identified CDRs (a-19) to (c-19); and
(h-19) a heavy chain variable region comprising the above-identified CDRs (d-19) to (f-19),
Group 44
(g-20) a light chain variable region comprising the above-identified CDRs (a-20) to (c-20); and
(h-20) a heavy chain variable region comprising the above-identified CDRs (d-20) to (f-20),
Group 45
(g-21) a light chain variable region comprising the above-identified CDRs (a-21) to (c-21); and
(h-21) a heavy chain variable region comprising the above-identified CDRs (d-21) to (f-21),
Group 46
(g-22) a light chain variable region comprising the above-identified CDRs (a-22) to (c-22); and
(h-22) a heavy chain variable region comprising the above-identified CDRs (d-22) to (f-22),
Group 47
(g-23) a light chain variable region comprising the above-identified CDRs (a-23) to (c-23); and
(h-23) a heavy chain variable region comprising the above-identified CDRs (d-23) to (f-23), Group 48

(g-24) a light chain variable region comprising the above-identified CDRs (a-24) to (c-24); and (h-24) a heavy chain variable region comprising the above-identified CDRs (d-24) to (f-24).

[9] The antibody of [8], which comprises the combination of the light chain variable region and the heavy chain variable region described in any one of the following groups 49 to 72.

Group 49

(i-1) a light chain variable region comprising the amino acid sequence shown in SEQ ID NO:8; and (j-1) a heavy chain variable region comprising amino acid sequence shown in SEQ ID NO:10, Group 50

(i-2) a light chain variable region comprising the amino acid sequence shown in SEQ ID NO:38; and (j-2) a heavy chain variable region comprising amino acid sequence shown in SEQ ID NO:10, Group 51

(i-3) a light chain variable region comprising the amino acid sequence shown in SEQ ID NO:41; and (j-3) a heavy chain variable region comprising amino acid sequence shown in SEQ ID NO:10, Group 52

(i-4) a light chain variable region comprising the amino acid sequence shown in SEQ ID NO:44; and (j-4) a heavy chain variable region comprising amino acid sequence shown in SEQ ID NO:10, Group 53

(i-5) a light chain variable region comprising the amino acid sequence shown in SEQ ID NO:47; and (j-5) a heavy chain variable region comprising amino acid sequence shown in SEQ ID NO:10, Group 54

(i-6) a light chain variable region comprising amino acid sequence shown in SEQ ID NO:50; and (j-6) a heavy chain variable region comprising amino acid sequence shown in SEQ ID NO:10, Group 55

(i-7) a light chain variable region comprising amino acid sequence shown in SEQ ID NO:53; and (j-7) a heavy chain variable region comprising amino acid sequence shown in SEQ ID NO:10, Group 56

(i-8) a light chain variable region comprising amino acid sequence shown in SEQ ID NO:56; and (j-8) a heavy chain variable region comprising amino acid sequence shown in SEQ ID NO:57, Group 57

(i-9) a light chain variable region comprising amino acid sequence shown in SEQ ID NO:62; and (j-9) a heavy chain variable region comprising amino acid sequence shown in SEQ ID NO:63, Group 58

(i-10) a light chain variable region comprising amino acid sequence shown in SEQ ID NO:67; and (j-10) a heavy chain variable region comprising amino acid sequence shown in SEQ ID NO:10, Group 59

(i-11) a light chain variable region comprising amino acid sequence shown in SEQ ID NO:71; and (j-11) a heavy chain variable region comprising amino acid sequence shown in SEQ ID NO:72, Group 60

(i-12) a light chain variable region comprising amino acid sequence shown in SEQ ID NO:75; and (j-12) a heavy chain variable region comprising amino acid sequence shown in SEQ ID NO:10, Group 61

(i-13) a light chain variable region comprising amino acid sequence shown in SEQ ID NO:8; and (j-13) a heavy chain variable region comprising amino acid sequence shown in SEQ ID NO:78, Group 62

(i-14) a light chain variable region comprising amino acid sequence shown in SEQ ID NO:82; and (j-14) a heavy chain variable region comprising amino acid sequence shown in SEQ ID NO:83, Group 63

(i-15) a light chain variable region comprising amino acid sequence shown in SEQ ID NO:86; and (j-15) a heavy chain variable region comprising amino acid sequence shown in SEQ ID NO:87, Group 64

(i-16) a light chain variable region comprising amino acid sequence shown in SEQ ID NO:91; and (j-16) a heavy chain variable region comprising amino acid sequence shown in SEQ ID NO:10, Group 65

(i-17) a light chain variable region comprising amino acid sequence shown in SEQ ID NO:94; and (j-17) a heavy chain variable region comprising amino acid sequence shown in SEQ ID NO:95, Group 66

(i-18) a light chain variable region comprising amino acid sequence shown in SEQ ID NO:100; and (j-18) a heavy chain variable region comprising amino acid sequence shown in SEQ ID NO:101, Group 67

(i-19) a light chain variable region comprising amino acid sequence shown in SEQ ID NO:104; and (j-19) a heavy chain variable region comprising amino acid sequence shown in SEQ ID NO:101, Group 68

(i-20) a light chain variable region comprising amino acid sequence shown in SEQ ID NO:106; and (j-20) a heavy chain variable region comprising amino acid sequence shown in SEQ ID NO:10, Group 69

(i-21) a light chain variable region comprising amino acid sequence shown in SEQ ID NO:108; and (j-21) a heavy chain variable region comprising amino acid sequence shown in SEQ ID NO:57, Group 70

(i-22) a light chain variable region comprising amino acid sequence shown in SEQ ID NO:111; and (j-22) a heavy chain variable region comprising amino acid sequence shown in SEQ ID NO:112, Group 71

(i-23) a light chain variable region comprising amino acid sequence shown in SEQ ID NO:116; and (j-23) a heavy chain variable region comprising amino acid sequence shown in SEQ ID NO:117, Group 72

(i-24) a light chain variable region comprising amino acid sequence shown in SEQ ID NO:121; and (j-24) a heavy chain variable region comprising amino acid sequence shown in SEQ ID NO:122.

[10] The antibody of [8] or [9], which comprises the combination of the light chain and the heavy chain described in any one of the following groups 73 to 96.

Group 73

(k-1) a light chain comprising the amino acid sequence shown in SEQ ID NO:26; and (l-1) a heavy chain comprising the amino acid sequence shown in SEQ ID NO:28, Group 74

(k-2) a light chain comprising the amino acid sequence shown in SEQ ID NO:39; and (l-2) a heavy chain comprising the amino acid sequence shown in SEQ ID NO:28, Group 75

(k-3) a light chain comprising the amino acid sequence shown in SEQ ID NO:42; and (l-3) a heavy chain comprising the amino acid sequence shown in SEQ ID NO:28, Group 76

(k-4) a light chain comprising the amino acid sequence shown in SEQ ID NO:45; and (l-4) a heavy chain comprising the amino acid sequence shown in SEQ ID NO:28, Group 77

(k-5) a light chain comprising the amino acid sequence shown in SEQ ID NO:48; and (l-5) a heavy chain comprising the amino acid sequence shown in SEQ ID NO:28, Group 78

(k-6) a light chain comprising the amino acid sequence shown in SEQ ID NO:51; and (l-6) a heavy chain comprising the amino acid sequence shown in SEQ ID NO:28, Group 79

(k-7) a light chain comprising the amino acid sequence shown in SEQ ID NO:54; and (l-7) a heavy chain comprising the amino acid sequence shown in SEQ ID NO:28, Group 80

(k-8) a light chain comprising the amino acid sequence shown in SEQ ID NO:58; and (l-8) a heavy chain comprising the amino acid sequence shown in SEQ ID NO:59, Group 81

(k-9) a light chain comprising the amino acid sequence shown in SEQ ID NO:64; and (l-9) a heavy chain comprising the amino acid sequence shown in SEQ ID NO:65, Group 82

(k-10) a light chain comprising the amino acid sequence shown in SEQ ID NO:68; and (l-10) a heavy chain comprising the amino acid sequence shown in SEQ ID NO:28, Group 83

(k-11) a light chain comprising the amino acid sequence shown in SEQ ID NO:73; and (l-11) a heavy chain comprising the amino acid sequence shown in SEQ ID NO:74, Group 84

(k-12) a light chain comprising the amino acid sequence shown in SEQ ID NO:76; and (l-12) a heavy chain comprising the amino acid sequence shown in SEQ ID NO:28, Group 85

(k-13) a light chain comprising the amino acid sequence shown in SEQ ID NO:26; and (l-13) a heavy chain comprising the amino acid sequence shown in SEQ ID NO:79, Group 86

(k-14) a light chain comprising the amino acid sequence shown in SEQ ID NO:84; and (l-14) a heavy chain comprising the amino acid sequence shown in SEQ ID NO:85, Group 87

(k-15) a light chain comprising the amino acid sequence shown in SEQ ID NO:88; and (l-15) a heavy chain comprising the amino acid sequence shown in SEQ ID NO:89, Group 88

(k-16) a light chain comprising the amino acid sequence shown in SEQ ID NO:92; and (l-16) a heavy chain comprising the amino acid sequence shown in SEQ ID NO:28, Group 89

(k-17) a light chain comprising the amino acid sequence shown in SEQ ID NO:96; and (l-17) a heavy chain comprising the amino acid sequence shown in SEQ ID NO:97, Group 90

(k-18) a light chain comprising the amino acid sequence shown in SEQ ID NO:102; and (l-18) a heavy chain comprising the amino acid sequence shown in SEQ ID NO:103, Group 91

(k-19) a light chain comprising the amino acid sequence shown in SEQ ID NO:105; and (l-19) a heavy chain comprising the amino acid sequence shown in SEQ ID NO:103, Group 92

(k-20) a light chain comprising the amino acid sequence shown in SEQ ID NO:107; and (l-20) a heavy chain comprising the amino acid sequence shown in SEQ ID NO:28, Group 93

(k-21) a light chain comprising the amino acid sequence shown in SEQ ID NO:109; and (l-21) a heavy chain comprising the amino acid sequence shown in SEQ ID NO:59, Group 94

(k-22) a light chain comprising the amino acid sequence shown in SEQ ID NO:113; and (l-22) a heavy chain comprising the amino acid sequence shown in SEQ ID NO:114, Group 95

(k-23) a light chain comprising the amino acid sequence shown in SEQ ID NO:118; and (l-23) a heavy chain comprising the amino acid sequence shown in SEQ ID NO:119, Group 96

(k-24) a light chain comprising the amino acid sequence shown in SEQ ID NO:123; and (l-24) a heavy chain comprising the amino acid sequence shown in SEQ ID NO:124.

[11] An antibody binding to the human CD81 having the amino acid sequence shown in SEQ ID NO:22 competitively with the antibody of any one of [7] to [10].

[12] The antibody of [11], which has a suppressive effect of T cell migration.

[13] An anti-human CD81 antibody, wherein the antibody comprises one or more of CDRs described in any one of the groups 1 to 24 in [7] and binds to the human CD81 having the amino acid sequence shown in SEQ ID NO:22 competitively with the antibody comprising all 6 CDRs described in said group.

[14] An anti-human CD81 antibody, wherein the antibody has a 90% sequence homology with any one of antibodies of [7] and binds to the human CD81 having the amino acid sequence shown in SEQ ID NO:22 competitively with said antibody.

[15] An anti-human CD81 antibody comprising:

(a-25) a CDR comprising the amino acid sequence shown in SEQ ID NO:11;

(b-25) a CDR comprising the amino acid sequence shown in SEQ ID NO:12;

(c-25) a CDR comprising the amino acid sequence shown in SEQ ID NO:13;

(d-25) a CDR comprising the amino acid sequence shown in SEQ ID NO:14;

(e-25) a CDR comprising the amino acid sequence shown in SEQ ID NO:15; and (f-25) a CDR comprising the amino acid sequence shown in SEQ ID NO:16.

[16] The antibody of [15], which comprises:

(g-25) a light chain variable region comprising the above-identified CDRs (a-25) to (c-25); and (h-25) a heavy chain variable region comprising the above-identified CDRs (d-25) to (f-25).

[17] The antibody of [16], which comprises:

(i-25) a light chain variable region comprising the amino acid sequence shown in SEQ ID NO:18; and (j-25) a heavy chain variable region comprising the amino acid sequence shown in SEQ ID NO:20.

[18] The antibody of [16] or [17], which comprises:

(k-25) a light chain comprising the amino acid sequence shown in SEQ ID NO:30; and (l-25) a heavy chain comprising the amino acid sequence shown in SEQ ID NO:32

[19] An antibody binding to the human CD81 having the amino acid sequence shown in SEQ ID NO:22 competitively with the antibody of any one of [15] to [18].

[20] The antibody of [19], which has a suppressive effect of T cell migration.

[21] An anti-human CD81 antibody, wherein the antibody comprises one or more of CDRs in [15] and binds to the human CD81 having the amino acid sequence shown in SEQ ID NO:22 competitively with the antibody described in [15].

[22] An anti-human CD81 antibody, wherein the antibody has a 90% sequence homology with the antibody described in [15] and binds to the human CD81 having the amino acid sequence shown in SEQ ID NO:22 competitively with said antibody.

[23] The antibody of any one of [1] to [6], [11] to [14] and [19] to [22] which is a humanized or human antibody.

[24] The antibody of any one of [7] to [10] and [15] to [18] which is a humanized or human antibody.

[25] The polynucleotide comprising a nucleotide sequence that encodes a heavy chain variable region and a light chain variable region of the antibody of any one of [1] to [24].

[26] A combination of the polynucleotide comprising a nucleotide sequence that encodes a heavy chain variable region of the antibody of any one of [1] to [6], [11] to [14] and [19] to [23], and the polynucleotide comprising a nucleotide sequence that encodes a light chain variable region of the antibody of any one of [1] to [6], [11] to [14] and [19] to [23].

[27] A combination of the polynucleotide comprising a nucleotide sequence that encodes a heavy chain variable region of the antibody of any one of [7] to [10], [15] to [18] and [24], and the polynucleotide comprising a nucleotide sequence that encodes the corresponding light chain variable region of the antibody of any one of [7] to [10], [15] to [18] and [24].

[28] The polynucleotide comprising a nucleotide sequence that encodes a heavy chain and a light chain of the antibody of any one of [1] to [24].

[29] A combination of the polynucleotide comprising a nucleotide sequence that encodes a heavy chain of the antibody of any one of [1] to [6], [11] to [14] and [19] to [23], and the polynucleotide comprising a nucleotide sequence that encodes a light chain of the antibody of any one of [1] to [6], [11] to [14] and [19] to [23].

[30] A combination of the polynucleotide comprising a nucleotide sequence that encodes a heavy chain of the antibody of any one of [7] to [10], [15] to [18] and [24], and the polynucleotide comprising a nucleotide sequence that encodes the corresponding light chain of the antibody of any one of [7] to [10], [15] to [18] and [24].

[31] An expression vector comprising the polynucleotide of [25] or [28].

[32] A recombinant cell transformed with the expression vector of [31].

[33] A recombinant cell transformed with the expression vector comprising the polynucleotide comprising a nucleotide sequence that encodes a heavy chain of the antibody of any one of [1] to [6], [11] to [14] and [19] to [23], and with the expression vector comprising the polynucleotide comprising a nucleotide sequence that encodes a light chain of the antibody of any one of [1] to [6], [11] to [14] and [19] to [23].

[34] A recombinant cell transformed with the expression vector comprising the polynucleotide comprising a nucleotide sequence that encodes the heavy chain of the antibody of any one of [7] to [10], [15] to [18] and [24], and with the expression vector comprising the polynucleotide comprising a nucleotide sequence that encodes the corresponding light chain of the antibody of any one of [7] to [10], [15] to [18] and [24].

[35] A method of producing an anti-human CD81 antibody, comprising culturing the recombinant cell of any one of [32] to [34], and recovering the antibody from the culture obtained.

[36] A pharmaceutical composition comprising the antibody of any one of [1] to [24].

[37] An agent for the prophylaxis, improvement or treatment of a disease selected from inflammatory bowel disease, multiple sclerosis, psoriasis and hematological cancer comprising the antibody of any one of [1] to [24].

[38] The antibody of any one of [1] to [3], wherein the binding affinity of the antibody to each of the above-identified human CD81 variants (3), (4), (8), (11) and (12) is less than 40% of that to the human CD81 having the amino acid sequence shown in SEQ ID NO:22.

[39] The antibody of any one of [1] to [3], wherein the binding affinity of the antibody to each of the above-identified human CD81 variants (3), (4), (6) and (8) to (13) is less than 40% of that to the human CD81 having the amino acid sequence shown in SEQ ID NO:22.

[40] The antibody of any one of [1] to [3], wherein the binding affinity of the antibody to each of the above-identified human CD81 variants (1) to (5), (7), (8), (11), and (12) is less than 40% of that to the human CD81 having the amino acid sequence shown in SEQ ID NO:22.

The present invention can provide a human monoclonal antibody against human CD81 with a superior drug efficacy and low immunogenicity to human. Since the present inventors obtained new findings that the anti-CD81 antibodies suppressed T cell migration, and moreover, exhibited cytotoxic effect on cancer cells, the antibody of the present invention is also useful for the prophylaxis, improvement or treatment of inflammatory diseases including inflammatory bowel diseases, and diseases associated with T cell migration including autoimmune diseases such as multiple sclerosis and psoriasis, as well as cancers caused by CD81-expressing cancer cells, including hematological cancers.

DETAILED DESCRIPTION OF THE INVENTION

In the present specification, the indication using abbreviations such as amino acid, (poly)peptide, (poly)nucleotide and the like follows the definitions of IUPAC-IUB [IUPAC-IUB Communication on Biological Nomenclature, Eur. J. Biochem., 138: 9 (1984)], "Guideline for preparing specification and the like containing nucleotide sequence or amino acid sequence" (ed. Japan Patent Office), and conventional marks used in the field.

Herein, the "gene" or "DNA" is used in the meaning that it includes not only a double-stranded DNA but also respective single-stranded DNAs, a sense strand and an antisense strand constituting the double-stranded DNA. It is not particularly limited by the length thereof. Accordingly, the gene (DNA) in the specification includes, unless otherwise instructed, a double-stranded DNA including a human genomic DNA, a single-stranded DNA (plus strand) including a cDNA, a single-stranded DNA having a sequence complementary to the plus strand (complementary strand) and fragments thereof.

Herein, the term "CD81 gene" means a human CD81 gene (DNA) shown by SEQ ID NO:21, or naturally occurring mutants or polymorphic variants thereof (except those encoding any of the mutant proteins of (1) to (13) described below, as a result of the mutation or polymorphism). Such mutants or polymorphic variants include, for example, those registered in the SNP database available form NCBI.

Herein, the term "CD81 protein" or simply "CD81" means a human CD81 protein shown by SEQ ID NO:22, or a protein encoded by the naturally occurring mutant or polymorphic variant DNAs mentioned above.

The "antibody" used herein encompasses a polyclonal antibody, a monoclonal antibody, a chimeric antibody, a single-stranded antibody, or a part thereof capable of binding with its antigen such as an Fab fragment or a fragment generated from an Fab expression library.

Herein, the term "epitope" is a region of an antigen to which an antibody binds. In certain embodiments, it includes any site on an antigen that is capable of specific binding to an immunoglobulin or T cell receptor or B cell receptor. Antigen determinants include chemically active surface groupings of molecules such as amino acids, sugar side chains, phosphoryl groups, or sulfonyl groups, and, in certain embodiments, may have specific three-dimensional structural characteristics, and/or specific charge characteristics. In certain embodiments, it can be mentioned that an antibody specifically binds to its target antigen when it preferentially recognizes the antigen in a complex mixture of proteins and/or macromolecules.

Structure of Antibody

The basic structure of an antibody molecule is shared by all classes, and consists of both a heavy chain having a molecular weight of 50000 to 70000 and a light chain having a molecular weight of 20000 to 30000 (Immunology 4th ed., I. Roitt, J. Brostoff, D. Male eds., Mosby-Year Book, 1996). A heavy chain usually consists of a polypeptide chain comprising about 440 amino acids; heavy chains have characteristic structures in each different classes, and are called the $\gamma$, $\mu$, $\alpha$, $\delta$, and $\epsilon$ chains corresponding to IgG, IgM, IgA, IgD, and IgE. Furthermore, IgG occurs as IgG1, IgG2, IgG3, and IgG4, and corresponding chains are called $\gamma 1$, $\gamma 2$, $\gamma 3$, and $\gamma 4$, respectively. A light chain usually consists of a polypeptide chain comprising about 220 amino acids; two types, type L and type K, are known, and are called the $\lambda$, and $\kappa$ chains, respectively. Regarding the peptide configuration of the basic structure of an antibody molecule, two homologous heavy chains and two homologous light chains are bound via disulfide bonds (S—S bonds) and non-covalent bonds, and the molecular weight is 150000 to 190000. The two kinds of light chains are capable of paring with any heavy chain. Each antibody molecule always consists of two identical light chains and two identical heavy chains.

There are four intra-molecular S—S bonds in a heavy chain (five bonds for $\mu$ and $\epsilon$ chains) and two in a light chain; one loop is formed per 100 to 110 amino acid residues, and this steric structure is alike among the loops, and is called a structural unit or domain. For both heavy chains and light chains, the amino acid sequence of the domain located at the N terminus thereof is inconstant, even in preparations from the same class (subclass) of the same animal species, and this domain is called a variable region (V region) (the heavy chain variable region domain is called as $V_H$ and the light chain variable region domain is called as $V_L$). The amino acid sequence on the C-terminal side therefrom is nearly constant in each class or subclass, and is called a constant region (C region) (the domains are expressed as $C_H1$, $C_H2$, $C_H3$ and $C_L$, respectively).

The antigen determination site of an antibody consists of $V_H$ and $V_L$, and the binding specificity depends on the amino acid sequence of this site. On the other hand, biological activities such as binding to complements or various cells reflect the differences in C region structure among the various classes of Ig. The variability of the variable regions of light chain and heavy chain has been found to be nearly limited to three small hypervariable regions existing in both chains, and these regions are called complementarity determining region (CDR). Several numbering systems for identifying CDRs are in common use. The Kabat definition is based on sequence variability, and the Chothia definition is based on the location of the structural loop regions. The AbM definition is a compromise between the Kabat and Chothia approaches. The CDRs of the light chain and heavy chain variable regions are bounded according to the Kabat, Chothia, or AbM algorithm (Martin et al. (1989) Proc. Natl. Acad. Sci. USA 86: 9268-9272; Martin et al. (1991) Methods Enzymol. 203: 121-153; Pedersen et al. (1992) Immunomethods 1: 126; and Rees et al. (1996) In Sternberg M. J. E. (ed.), Protein Structure Prediction, Oxford University Press, Oxford, pp. 141-172).

In the case of 002-A07 antibody, the CDRs in the heavy chain variable region are bounded by the residues at amino acid Nos. 29-42 (CDR1-H), 49-67 (CDR2-H) and 97-108 (CDR3-H) of the amino acid sequence shown by SEQ ID NO:10, and the CDRs in the light chain variable region are bounded by the residues at amino acid Nos. 22-36 (CDR1-L), 52-58 (CDR2-L) and 90-101 (CDR3-L) of the amino acid sequence shown by SEQ ID NO:8. In the case of 005-C01 antibody, the CDRs in the heavy chain variable region are bounded by the residues at amino acid Nos. 29-42 (CDR1-H), 49-67 (CDR2-H) and 97-102 (CDR3-H) of the amino acid sequence shown by SEQ ID NO:20, and the CDRs in the light chain variable region are bounded by the residues at amino acid Nos. 22-35 (CDR1-L), 51-57 (CDR2-L) and 89-99 (CDR3-L) of the amino acid sequence shown by SEQ ID NO:18.

The portion other than CDRs of the variable region is called a framework region (FR), and is relatively constant. The framework region employs a β sheet conformation, and CDRs can form a loop connecting the β sheet structure. CDRs in each chain are maintained in the three dimensional structure thereof by the framework regions and form an antigen binding site together with CDRs from the other chain.

Binding Assay of Antibody

Antibody binding can be confirmed by any known assay method, such as direct and indirect sandwich assays, flow cytometry and immunoprecipitation assays (Zola, Monoclonal Antibodies: A Manual of Techniques, CRC Press, Inc., 1987, pp. 147-158). In the present invention, the binding of an anti-human CD81 monoclonal antibody with a human CD81 polypeptide or a cell presenting same on its surface can be measured, for example, by the following method.

As a typical method, exemplified is a method comprising adsorbing a human CD81 polypeptide (antigen) onto a solid phase, blocking the solid phase with a protein that is not involved in the subsequent antigen-antibody reaction or enzyme reaction (e.g., skim milk, albumin etc.), contacting and incubating a human anti-human CD81 monoclonal antibody (test antibody) with the solid phase, removing an unreacted antibody by B/F separation, and adding a labeled secondary antibody specifically reacting with the test antibody (e.g., anti-human IgG, etc.) to the solid phase to determine the amount of the label on the solid phase. As the solid phase, for example, insoluble polysaccharides such as agarose, dextran and cellulose, synthetic resins such as plastic, polystylene, polyacrylamide and silicone (e.g., tube, microplate, etc.), or glass (beads, tube, etc.) can be used. The membrane fraction of a cell expressing a human CD81 polypeptide may be used as an antigen to be adsorbed onto the solid phase, as shown in Experimental Example 7(2) described below. As a means for immobilization, an antigen may be recombinantly expressed as a fusion protein with a peptide (e.g., His-tag, GST, MBP, etc.) capable of binding with a solid phase (Ni-, glutathione-, maltose-carrier, etc.) and bound to the solid phase with affinity thereto, as shown in Experimental Example 7(2). As the labeling agent, radioisotopes, enzymes, fluorescent substances, luminescent substances and the like can be used. As examples of the radioisotopes, [$^{125}$I], [$^{131}$], [$^{3}$H], [$^{14}$C] and the like can be mentioned. As examples of the enzymes, stable enzymes with high specific activity are preferred; for example, β-galactosidase, β-glucosidase, alkaline phosphatase, peroxidase, malate dehydrogenase and the like can be mentioned. As examples of the fluorescent substances, fluorescamine, fluorescein isothiocyanate and the like can be mentioned. As examples of the luminescent substances, luminol, luminol derivatives, luciferin, luciferin and the like can be mentioned.

In the sandwich method, an immobilized anti-human CD81 antibody, which binds to human CD81 at a site different from the site to which the antibody of the present invention binds, is reacted with a human CD81 polypeptide (antigen), and further reacted with an anti-human CD81 monoclonal antibody (test antibody). After removing an unreacted antibody by B/F separation, a labeled secondary antibody specifically reacting with the test antibody (e.g., anti-human IgG, etc.) is added to determine the amount of the label on the solid phase. The labeling agent and the solid phase may be the same as mentioned above.

To examine binding of anti-human CD81 monoclonal antibodies to live cells expressing a human. CD81 polypeptide, flow cytometry can be used. Briefly, a cell expressing human CD81 (grown under standard growth conditions) can be mixed with an anti-human CD81 antibody (test antibody) in, for example, PBS containing 0.1% BSA, and incubated at 37° C. for 1 hour. After washing, the cells are reacted with a secondary antibody (e.g., anti-human IgG antibody) labeled with a fluorescent such as fluorescein or phycoerythrin (PE) under the same conditions as the reaction with test antibody. The samples can be analyzed by a flow cytometer using light and side scatter properties to gate on single cells. For example, when the percentage of the cells possessing a fluorescent intensity greater than that when non-specific antibody (e.g., human IgG) is used is 90% or more, preferably 95% or more, more preferably 97% or more, the test antibody can be confirmed to specifically bind to the antigen. An alternative assay using fluorescence microscopy may be used in addition to or instead of the flow cytometry assay. Cells can be stained exactly as described above and examined by fluorescence microscopy. This method allows visualization of individual cells.

Competitive Assay

Competitive assays such as competitive ELISA can be used to determine the binding constant (Ka) of an anti-human CD81 antibody or identify another antibody of the present invention, which binds to a human CD81 competitively with the antibody of the present invention already obtained (known antibody). The competitive assays are carried out by adding a free antigen or known antibody to the reaction system of the solid phase and the test antibody in the binding assay using antigen-immobilized solid phase mentioned above. For example, a given concentration of test antibody solution and mixtures in which various concentrations of antigen are added to the test antibody solution are contacted and incubated with an antigen-immobilized solid phase, respectively, and the amounts of label on the respective solid phases are measured. The binding constant can be calculated as the gradient of graph showing the results of Scatchard analysis based on the measured values for respective antigen concentrations. On the other hand, an antibody binding to a human CD81 competitively with the antibody of the present invention can be identified by reacting a labeled known antibody (the inventive antibody) and various concentrations of test antibody with the antigen-immobilized solid phase, and selecting the test antibody that reduced the amount of label on the solid phase in a dose-dependent manner.

Antibody of the Present Invention

The antibody of the present invention is an anti-human CD81 antibody capable of binding to a peptide region consisting of the amino acid sequence of the amino acid numbers 80 to 175, preferably 113 to 175, in the amino acid sequence shown in SEQ ID NO:22, or an antibody binding to the human CD81 consisting of the amino acid sequence shown in SEQ ID NO:22 competitively with said anti-human CD81 antibody. The amino acid sequence shown in SEQ ID NO:22 is a reported amino acid sequence of human CD81 protein (*EMBO J.,* 20: 12-18, 2001), and registered in NCBI database as Refseq ID: NP_004347. Hereinafter, the protein consisting of the amino acid sequence is also referred to as "naturally occurring human CD81", "wild type CD81" or "wild type human CD81".

The present invention is based on the findings that anti-human CD81 antibodies that recognize the peptide region mentioned above as an epitope exert their therapeutic effect such as suppression of T cell migration with no or few side effects.

The antibody of the present invention can be any monoclonal antibody, as long as it binds to the particular peptide region of the wild type human CD81 mentioned above, or binds to the wild type human CD81 competitively with an antibody binding to the peptide region.

Epitope Analysis

Epitope analysis can be carried out according to various known methods (Epitope Mapping Protocols/Second Edition, Mike Schutkowski, Ulrich Reineke, Ann N Y Acad. Sci. 2010 January; 1183: 267-87). More detailed epitope analysis for an antibody can be performed by binding inhibition assay, homolog scanning and/or alanine scanning (for example, see JP 2009-159948 A, *Science,* 244: 1081-1085 (1989)).

Alanine scanning is a method to determine whether each amino acid residue of human CD81 is necessary for binding of its antibody thereto by preparing mutants wherein each of the amino acid residues of wild type human CD81 is substituted with alanine, and examining differences in binding activity of the antibody between against CD81 mutants and against wild type human CD81.

Homolog scanning is a method to determine which amino acid residues can be inserted, substituted or deleted without adverse effect on activity by substituting at least one amino acid residue of wild type human CD81 polypeptide with other homologous amino acid(s). In this method, the amino acid sequence of human CD81 polypeptide is compared to those of known homologous protein molecules and the number of amino acid changes generated within the region having a high homology is minimized (*Protein Science,* 14, 2405-2413 (2005)).

The homolog scanning and alanine scanning mutagenesis carried out in the present invention (see Experimental examples 8 and 9 etc.) has revealed that the substitutions of the particular amino acid residues in the peptide region mentioned above with other amino acids remarkably reduce the binding affinity of the anti-human CD81 antibodies to the human CD81 mutants. These findings show that the substituted amino acid residues mainly contribute to the binding of the antibodies to wild type human CD81.

Accordingly, in a preferable embodiment, the antibody of the present invention is characterized in that its binding affinity to at least one CD81 variant selected from the following (1) to (13) is less than 40% when its binding affinity to the above-mentioned wild type human 0081 is 100%:

(1) 0081 variant in which the 127th tyrosine (Y) of wild type human CD81 is substituted with phenylalanine or tryptophan;

(2) 0081 variant in which the 130th alanine (A) of wild type human CD81 is substituted with threonine or valine;

(3) CD81 variant in which the 135th valine (V) of wild type human CD81 is substituted with alanine or leucine;

(4) CD81 variant in which the 137th aspartic acid (D) of wild type human CD81 is substituted with alanine or glutamic acid;

(5) CD81 variant in which the 143rd alanine (A) of wild type human CD81 is substituted with threonine or valine;

(6) CD81 variant in which the 151st histidine (H) of wild type human CD81 is substituted with alanine or arginine;

(7) CD81 variant in which the 154th leucine (L) of wild type human CD81 is substituted with alanine or isoleucine;

(8) CD81 variant in which the 158th glycine (G) of wild type human CD81 is substituted with alanine or serine;

(9) CD81 variant in which the 164th alanine (A) of wild type human CD81 is substituted with threonine or valine;

(10) CD81 variant in which the 168th serine (S) of wild type human CD81 is substituted with alanine or threonine;

(11) CD81 variant in which the 169th valine (V) of wild type human CD81 is substituted with alanine or leucine;

(12) CD81 variant in which the 170th leucine (L) of wild type human CD81 is substituted with alanine or isoleucine; and

(13) CD81 variant in which the 172nd asparagine (N) of wild type human CD81 is substituted with alanine or glutamine;

wherein the positions of the amino acid residues to be substituted are identified as the amino acid numbers of the amino acid sequence shown in SEQ ID NO:22.

Here, the above-mentioned CD81 variants can be produced by the description of the following Experimental Example or a known method, for example, introducing a suitable nucleotide change causing an amino acid substitution into a DNA encoding the wild type human CD81 polypeptide, or chemically synthesizing a desired variant polypeptide. The mutation of human CD81 polypeptide described here can be formed by, for example, the technique or guideline relating to the preservative or non-preservative mutation shown in U.S. Pat. No. 5,364,934 (for example, see Experimental examples 8 and 9 of the present invention).

The binding affinity of an antibody to the wild type or a mutant human CD81 can be determined by various binding assays described above. The binding constant (Ka) of the antibody of the present invention against wild type human CD81 is at least $1\times10^{7}$ $M^{-1}$, preferably $10^{8}$ $M^{-1}$, more preferably $10^{8}$ $M^{-1}$, even more preferably $10^{10}$ $M^{-1}$. The binding constant of the antibody can be determined by the competitive assay described above or other well-known methods such as surface plasmon resonance (SPR).

More preferably, the antibody of the present invention is such that the binding affinity to each of the human CD81 variants (9) and (11) above is less than 40% of that to wild type human CD81. The antibody of the present invention is also such that the binding affinity to each of the human 0081 variants (3), (4), (9) and (11) above is less than 40% of that to wild type human 0081, that the binding affinity to each of the human CD81 variants (3), (4), (9), (10) and (11) above is less than 40%, that the binding affinity to each of the human CD81 variants (3), (4), (8), (9), (10) and (11) above is less than 40%, or the binding affinity to each of the human CD81 variants (3), (4), (6), (8), (9), (10), (11) and (12) above is less than 40%. The series of antibodies possessing the binding characteristic are described in detail in (i) below. In the case of an antibody comprising all six CDRs belonging to the group 1, which represents a specific mode of embodiment of the present invention described in (i) below, the binding affinity to each of the human CD81 variants (3), (4), (6) and (8) to (13) above is less than 40%.

In another preferred embodiment, the antibody of the present invention is such that the binding affinity to each of the human CD81 variants (1) to (5), (7), (8), (11) and (12) above is less than 40% of that to wild type human CD81. The series of antibodies possessing the binding characteristic are described in detail in (ii) below. Human CD81 variants shared by this antibody and the aforementioned antibody in the specific mode of embodiment described in (i) below, whose binding affinity is less than 40% of that to wild type human CD81, are the human CD81 variants (3), (4), (8), (11) and (12) above, respectively.

The present invention also provides an antibody binding to wild type human CD81 competitively with any antibody of the present invention described above. The antibody can bind to wild type human CD81 antibody in a region containing amino acid(s) outside the amino acid region of amino acid Nos. 80-175 in the amino acid sequence shown in SEQ ID NO:22, as long as it has a suppressive effect on T cell migration and/or a cytotoxic effect on CD81-expressing cancer cells. While it is desirable that the suppressive effect on T cell migration and the cytotoxic activity on CD81-expressing cancer cells be equivalent (e.g., 0.5-2 fold) to those of an antibody binding to wild type human CD81 in the amino acid region of amino acid Nos. 80-175 or Nos. 113-175 in the amino acid sequence shown in SEQ ID NO:22, the extent of the activity may be different, as long as the antibody exerts a prophylactic, ameliorating or therapeutic effect on inflammatory bowel diseases, multiple sclerosis psoriasis, or hematological cancers of humans. The "competitive binding" of antibodies to their antigen can be examined by the competitive assay described above.

(i) One Specific Embodiment

One preferable embodiment is an antibody having a binding affinity of less than 40% to each of the human CD81 variants described in (9) and (11) when its binding affinity to wild type human CD81 is 100%.

A preferable example of the antibodies having the binding properties mentioned above is:

Group 1
(a-1) a CDR comprising the amino acid sequence shown in SEQ ID NO:1,
(b-1) a CDR comprising the amino acid sequence shown in SEQ ID NO:2,
(c-1) a CDR comprising the amino acid sequence shown in SEQ ID NO:3,
(d-1) a CDR comprising the amino acid sequence shown in SEQ ID NO:4,
(e-1) a CDR comprising the amino acid sequence shown in SEQ ID NO:5, and
(f-1) a CDR comprising the amino acid sequence shown in SEQ ID NO:6

Group 2
(a-2) a CDR comprising the amino acid sequence shown in SEQ ID NO:1,
(b-2) a CDR comprising the amino acid sequence shown in SEQ ID NO:2,
(c-2) a CDR comprising the amino acid sequence shown in SEQ ID NO:37,
(d-2) a CDR comprising the amino acid sequence shown in SEQ ID NO:4,
(e-2) a CDR comprising the amino acid sequence shown in SEQ ID NO:5, and
(f-2) a CDR comprising the amino acid sequence shown in SEQ ID NO:6

Group 3
(a-3) a CDR comprising the amino acid sequence shown in SEQ ID NO: 1,
(b-3) a CDR comprising the amino acid sequence shown in SEQ ID NO:2,
(c-3) a CDR comprising the amino acid sequence shown in SEQ ID NO:40,
(d-3) a CDR comprising the amino acid sequence shown in SEQ ID NO:4,
(e-3) a CDR comprising the amino acid sequence shown in SEQ ID NO:5, and
(f-3) a CDR comprising the amino acid sequence shown in SEQ ID NO:6

Group 4
(a-4) a CDR comprising the amino acid sequence shown in SEQ ID NO:1,
(b-4) a CDR comprising the amino acid sequence shown in SEQ ID NO:2,
(c-4) a CDR comprising the amino acid sequence shown in SEQ ID NO:43,
(d-4) a CDR comprising the amino acid sequence shown in SEQ ID NO:4,
(e-4) a CDR comprising the amino acid sequence shown in SEQ ID NO:5, and
(f-4) a CDR comprising the amino acid sequence shown in SEQ ID NO:6

Group 5
(a-5) a CDR comprising the amino acid sequence shown in SEQ ID NO:1,
(b-5) a CDR comprising the amino acid sequence shown in SEQ ID NO:2,
(c-5) a CDR comprising the amino acid sequence shown in SEQ ID NO:46,
(d-5) a CDR comprising the amino acid sequence shown in SEQ ID NO:4,
(e-5) a CDR comprising the amino acid sequence shown in SEQ ID NO:5, and
(f-5) a CDR comprising the amino acid sequence shown in SEQ ID NO:6

Group 6
(a-6) a CDR comprising the amino acid sequence shown in SEQ ID NO:1,
(b-6) a CDR comprising the amino acid sequence shown in SEQ ID NO:2,
(c-6) a CDR comprising the amino acid sequence shown in SEQ ID NO:49,
(d-6) a CDR comprising the amino acid sequence shown in SEQ ID NO:4,
(e-6) a CDR comprising the amino acid sequence shown in SEQ ID NO:5, and
(f-6) a CDR comprising the amino acid sequence shown in SEQ ID NO Group 7
(a-7) a CDR comprising the amino acid sequence shown in SEQ ID NO:1,
(b-7) a CDR comprising the amino acid sequence shown in SEQ ID NO:2,
(c-7) a CDR comprising the amino acid sequence shown in SEQ ID NO:52,
(d-7) a CDR comprising the amino acid sequence shown in SEQ ID NO:4,
(e-7) a CDR comprising the amino acid sequence shown in SEQ ID NO:5, and
(f-7) a CDR comprising the amino acid sequence shown in SEQ ID NO:6

Group 8
(a-8) a CDR comprising the amino acid sequence shown in SEQ ID NO:1,
(b-8) a CDR comprising the amino acid sequence shown in SEQ ID NO:2,
(c-8) a CDR comprising the amino acid sequence shown in SEQ ID NO:43,
(d-8) a CDR comprising the amino acid sequence shown in SEQ ID NO:4,
(e-8) a CDR comprising the amino acid sequence shown in SEQ ID NO:5, and
(f-8) a CDR comprising the amino acid sequence shown in SEQ ID NO:55

Group 9
(a-9) a CDR comprising the amino acid sequence shown in SEQ ID NO:60,
(b-9) a CDR comprising the amino acid sequence shown in SEQ ID NO:2,
(c-9) a CDR comprising the amino acid sequence shown in SEQ ID NO:3, (d-9) a CDR comprising the amino acid sequence shown in SEQ ID NO:4, (e-9) a CDR comprising the amino acid sequence shown in SEQ ID NO:5, and (f-9) a CDR comprising the amino acid sequence shown in SEQ ID NO:61

Group 10

(a-10) a CDR comprising the amino acid sequence shown in SEQ ID NO:1, (b-10) a CDR comprising the amino acid sequence shown in SEQ ID NO:2, (c-10) a CDR comprising the amino acid sequence shown in SEQ ID NO:66, (d-10) a CDR comprising the amino acid sequence shown in SEQ ID NO:4, (e-10) a CDR comprising the amino acid sequence shown in SEQ ID NO:5, and (f-10) a CDR comprising the amino acid sequence shown in SEQ ID NO:6

Group 11

(a-11) a CDR comprising the amino acid sequence shown in SEQ ID NO:1, (b-11) a CDR comprising the amino acid sequence shown in SEQ ID NO:2, (c-11) a CDR comprising the amino acid sequence shown in SEQ ID NO:3, (d-11) a CDR comprising the amino acid sequence shown in SEQ ID NO:4, (e-11) a CDR comprising the amino acid sequence shown in SEQ ID NO:69, and (f-11) a CDR comprising the amino acid sequence shown in SEQ ID NO:70

Group 12

(a-12) a CDR comprising the amino acid sequence shown in SEQ ID NO:60, (b-12) a CDR comprising the amino acid sequence shown in SEQ ID NO:2, (c-12) a CDR comprising the amino acid sequence shown in SEQ ID NO:66, (d-12) a CDR comprising the amino acid sequence shown in SEQ ID NO:4, (e-12) a CDR comprising the amino acid sequence shown in SEQ ID NO:5, and (f-12) a CDR comprising the amino acid sequence shown in SEQ ID NO:6

Group 13

(a-13) a CDR comprising the amino acid sequence shown in SEQ ID NO:1, (b-13) a CDR comprising the amino acid sequence shown in SEQ ID NO:2, (c-13) a CDR comprising the amino acid sequence shown in SEQ ID NO:3, (d-13) a CDR comprising the amino acid sequence shown in SEQ ID NO:77, (e-13) a CDR comprising the amino acid sequence shown in SEQ ID NO:5, and (f-13) a CDR comprising the amino acid sequence shown in SEQ ID NO:6

Group 14

(a-14) a CDR comprising the amino acid sequence shown in SEQ ID NO:80, (b-14) a CDR comprising the amino acid sequence shown in SEQ ID NO:2, (c-14) a CDR comprising the amino acid sequence shown in SEQ ID NO:3, (d-14) a CDR comprising the amino acid sequence shown in SEQ ID NO:4, (e-14) a CDR comprising the amino acid sequence shown in SEQ ID NO:81, and (f-14) a CDR comprising the amino acid sequence shown in SEQ ID NO:6

Group 15

(a-15) a CDR comprising the amino acid sequence shown in SEQ ID NO:1, (b-15) a CDR comprising the amino acid sequence shown in SEQ ID NO:2, (c-15) a CDR comprising the amino acid sequence shown in SEQ ID NO: 66, (d-15) a CDR comprising the amino acid sequence shown in SEQ ID NO:4, (e-15) a CDR comprising the amino acid sequence shown in SEQ ID NO:5, and (f-15) a CDR comprising the amino acid sequence shown in SEQ ID NO: 6

Group 16

(a-16) a CDR comprising the amino acid sequence shown in SEQ ID NO:1, (b-16) a CDR comprising the amino acid sequence shown in SEQ ID NO:2, (c-16) a CDR comprising the amino acid sequence shown in SEQ ID NO:90, (d-16) a CDR comprising the amino acid sequence shown in SEQ ID NO:4, (e-16) a CDR comprising the amino acid sequence shown in SEQ ID NO:5, and (f-16) a CDR comprising the amino acid sequence shown in SEQ ID NO:6

Group 17

(a-17) a CDR comprising the amino acid sequence shown in SEQ ID NO:1, (b-17) a CDR comprising the amino acid sequence shown in SEQ ID NO:2, (c-17) a CDR comprising the amino acid sequence shown in SEQ ID NO: 52, (d-17) a CDR comprising the amino acid sequence shown in SEQ ID NO:4, (e-17) a CDR comprising the amino acid sequence shown in SEQ ID NO:5, and (f-17) a CDR comprising the amino acid sequence shown in SEQ ID NO:93

Group 18

(a-18) a CDR comprising the amino acid sequence shown in SEQ ID NO:98, (b-18) a CDR comprising the amino acid sequence shown in SEQ ID NO:2, (c-18) a CDR comprising the amino acid sequence shown in SEQ ID NO:3, (d-18) a CDR comprising the amino acid sequence shown in SEQ ID NO:4, (e-18) a CDR comprising the amino acid sequence shown in SEQ ID NO:5, and (f-18) a CDR comprising the amino acid sequence shown in SEQ ID NO:99

Group 19

(a-19) a CDR comprising the amino acid sequence shown in SEQ ID NO:60, (b-19) a CDR comprising the amino acid sequence shown in SEQ ID NO:2, (c-19) a CDR comprising the amino acid sequence shown in SEQ ID NO: 3, (d-19) a CDR comprising the amino acid sequence shown in SEQ ID NO:4, (e-19) a CDR comprising the amino acid sequence shown in SEQ ID NO:5, and (f-19) a CDR comprising the amino acid sequence shown in SEQ ID NO:99

Group 20

(a-20) a CDR comprising the amino acid sequence shown in SEQ ID NO:1, (b-20) a CDR comprising the amino acid sequence shown in SEQ ID NO:2, (c-20) a CDR comprising the amino acid sequence shown in SEQ ID NO:90, (d-20) a CDR comprising the amino acid sequence shown in SEQ ID NO:4, (e-20) a CDR comprising the amino acid sequence shown in SEQ ID NO:5, and (f-20) a CDR comprising the amino acid sequence shown in SEQ ID NO:6

Group 21

(a-21) a CDR comprising the amino acid sequence shown in SEQ ID NO:1, (b-21) a CDR comprising the amino acid sequence shown in SEQ ID NO:2, (c-21) a CDR comprising the amino acid sequence shown in SEQ ID NO:3, (d-21) a CDR comprising the amino acid sequence shown in SEQ ID NO:4, (e-21) a CDR comprising the amino acid sequence shown in SEQ ID NO:5, and (f-21) a CDR comprising the amino acid sequence shown in SEQ ID NO:55

Group 22

(a-22) a CDR comprising the amino acid sequence shown in SEQ ID NO:1, (b-22) a CDR comprising the amino acid sequence shown in SEQ ID NO:2, (c-22) a CDR comprising the amino acid sequence shown in SEQ ID NO:66, (d-22) a CDR comprising the amino acid sequence shown in SEQ ID NO:110, (e-22) a CDR comprising the amino acid sequence shown in SEQ ID NO:5, and (f-22) a CDR comprising the amino acid sequence shown in SEQ ID NO:6

Group 23

(a-23) a CDR comprising the amino acid sequence shown in SEQ ID NO:1, (b-23) a CDR comprising the amino acid sequence shown in SEQ ID NO:2, (c-23) a CDR comprising the amino acid sequence shown in SEQ ID NO:3, (d-23) a CDR comprising the amino acid sequence shown in SEQ ID NO:4, (e-23) a CDR comprising the amino acid sequence shown in SEQ ID NO:5, and (f-23) a CDR comprising the amino acid sequence shown in SEQ ID NO:115

Group 24

(a-24) a CDR comprising the amino acid sequence shown in SEQ ID NO:1, (b-24) a CDR comprising the amino acid sequence shown in SEQ ID NO:2, (c-24) a CDR comprising the amino acid sequence shown in SEQ ID NO:90, (d-24) a CDR comprising the amino acid sequence shown in SEQ ID NO:4, (e-24) a CDR comprising the amino acid sequence shown in SEQ ID NO:120, and (f-24) a CDR comprising the amino acid sequence shown in SEQ ID NO:6; or (2) an antibody comprising CDRs of (a-X) to (f-X) (X is 1 to 24; the same applies below) above, wherein one or more, preferably one to several (e.g., 1, 2, 3, 4 or 5) amino acid residues are substituted and/or deleted and/or added and/or inserted in one or more (e.g., 1, 2, 3, 4, 5 or 6) amino acid sequences selected from the amino acid sequences shown in (a-X) to (f-X), and wherein the antibody has a binding property equivalent to that of any one of the above-mentioned antibodies, or binds to wild type human CD81 competitively with any one of the above-mentioned antibodies. Namely, the "equivalent binding property" means at least binding to a peptide region consisting of the 80th to 175th or 113th to 175th amino acid residues of wild type human CD81 polypeptide, preferably further binding to at least one human CD81 variant selected from (1) to (13) mentioned above (more preferably the variants (9) and (11)) in a binding affinity of less than 40% when its binding affinity to wild type human CD81 is 100%.

The antibody (2) above can be obtained by a publicly known method, for example, by performing PCR with a vector that encodes the base sequence of the variable region of the antibody (1) above as the template to comprehensively introduce mutations to generate a library of phage display mutant antibodies, screening the library with the binding activity for human CD81 or the competitive binding against the antibody (1) above as an index, and performing panning.

The binding property and competitive binding of an antibody can be determined by various binding assays and competitive assays described above. As a result of the assays, when the "equivalent binding property" or "competitive binding" of the tested antibody is confirmed, then its therapeutic effect can be tested by the cell migration experiment described in detail below.

A more preferable example of the antibodies having the binding properties mentioned above is an antibody comprising:

(1) a light chain variable region comprising the above-identified CDRs (a-X) to (c-X) and a heavy chain variable region comprising the above-identified CDRs (d-X) to (f-X); or (2) the light chain and heavy chain variable region of (1) above, wherein one or more, preferably one to several (e.g., 1, 2, 3, 4 or 5) amino acid residues are substituted and/or deleted and/or added and/or inserted in one or more (e.g., 1, 2, 3, 4, 5 or 6) amino acid sequences selected from the amino acid sequences shown in (a-X) to (f-X), and wherein the antibody has a binding property equivalent to that of any one of the above-mentioned antibodies, or binds to wild type human CD81 competitively with any one of the above-mentioned antibodies. Here, the "equivalent binding property" means the same as above.

More preferably, in the antibody mentioned above, the CDRs (a-X), (b-X) and (c-X) are located in this order from the N-terminus of the light chain. Namely, the CDRs (a-X), (b-X) and (c-X) corresponds to CDR1, CDR2 and CDR3 of the light chain, respectively. Similarly, the CDRs (d-X), (e-X) and (f-X) are located in this order from the N-terminus of the heavy chain. Namely, the CDRs (d-X), (e-X) and (f-X) correspond to CDR1, CDR2 and CDR3 of the heavy chain, respectively.

An even more preferable example of the antibodies having the binding properties mentioned above is an antibody comprising:

(1) a light chain variable region comprising the amino acid sequence shown in (i-X) and a heavy chain variable region comprising the amino acid sequence shown in (j-X); or (2) the light chain and heavy chain variable region of (1) above, wherein one or more, preferably 1 to 20, more preferably 1 to 10, even more preferably one to several (e.g., 1, 2, 3, 4 or 5) amino acid residues are substituted and/or deleted and/or added and/or inserted in either or both of the amino acid sequences shown in (i-X) and (j-X), and wherein the antibody has a binding property equivalent to that of any one of the above-mentioned antibodies, or binds to wild type human CD81 competitively with any one of the above-mentioned antibodies. Here, the "equivalent binding property" means the same as above.

Another preferable example of the antibodies having the binding properties mentioned above is an antibody that binds to the same or essentially the same epitope of wild type human CD81 as that to which the antibody comprising a light chain variable region comprising the amino acid sequence shown in (i-X) and a heavy chain variable region comprising the amino acid sequence shown in (j-X) binds. A more preferable example is an antibody that binds to the same or essentially the same epitope of wild type human CD81 as that to which the antibody comprising a light chain comprising the amino acid sequence shown in (k-X) and a heavy chain comprising the amino acid sequence shown in (l-X) binds.

Here, "essentially the same epitope" means an epitope that is different from, but sterically overlaps, the epitope recognized by an antibody having the above-mentioned particular light chain (variable region) and heavy chain (variable region) sequences. An antibody recognizing "essentially the same epitope" competes with an antibody having the above-mentioned particular light chain (variable region) and heavy chain (variable region) sequences for binding to wild type human CD81.

The most widely used and rapid methods for determining whether two antibodies bind to identical or sterically overlapping epitopes are competition assays, which can be configured in all number of different formats, using either labeled antigen or labeled antibody. Usually, the antigen is immobilized on a substrate, and the ability of unlabeled antibodies to block the binding of labeled antibodies is measured using radioactive isotopes or enzyme labels.

The antibody of the present invention may also be an antibody comprising at least one CDR selected from among six CDRs belonging to any one of the groups 1 to 24 above, that binds to wild type human CD81 competitively with an antibody comprising all the six CDRs.

Furthermore, the antibody of the present invention may be an antibody that possesses a homology of 80% or more, preferably 90% or more, more preferably 95% or more, to the amino acid sequences of the light chain and heavy chain of an antibody comprising all six CDRs belonging to any one of the groups 1 to 24 above, and binds to wild type human CD81 competitively with the antibody. Amino acid sequence homology as mentioned herein can be calculated using the blastp program of NCBI BLAST (National Center for Biotechnology Information Basic Local Alignment Search Tool) under the following conditions (expectancy-10; gap allowed; matrix-BLOSUM62; filtering-OFF).

(ii) Another Specific Embodiment

Another preferable embodiment is an antibody having a binding affinity of less than 40% to each of the human CD81 variants described in (1) to (5), (7), (8), (11) and (12) when its binding affinity to wild type human CD81 is 100%.

A preferable example of the antibodies having the binding properties mentioned above (1) an antibody comprising:

(a-25) a CDR comprising the amino acid sequence shown in SEQ ID NO:11;

(b-25) a CDR comprising the amino acid sequence shown in SEQ ID NO:12;

(c-25) a CDR comprising the amino acid sequence shown in SEQ ID NO:13;

(d-25) a CDR comprising the amino acid sequence shown in SEQ ID NO:14;

(e-25) a CDR comprising the amino acid sequence shown in SEQ ID NO:15; and (f-25) a CDR comprising the amino acid sequence shown in SEQ ID NO:16, or (2) an antibody comprising CDRs of (a-25) to (f-25) above, wherein one or more, preferably one to several (e.g., 1, 2, 3, 4 or 5) amino acid residues are substituted and/or deleted and/or added and/or inserted in one or more (e.g., 1, 2, 3, 4, 5 or 6) amino acid sequences selected from the amino acid sequences shown in SEQ ID NOs:11 to 16, and wherein the antibody has a binding property equivalent to that of any one of the above-mentioned antibodies, or binds to wild type human CD81 competitively with any one of the above-mentioned antibodies. Here, the "equivalent binding property" means the same as above.

The binding property and competitive binding of an antibody can be determined by various binding assays and competitive assays described above. As a result of the assays, when the "equivalent binding property" or "competitive binding" of the tested antibody is confirmed, then its therapeutic effect can be tested by the cell migration experiment described in detail below.

A more preferable example of the antibodies having the binding properties mentioned above is an antibody comprising:

(1) a light chain variable region comprising the above-identified CDRs (a-25) to (c-25) and a heavy chain variable region comprising the above-identified CDRs (d-25) to (f-25); or (2) the light chain and heavy chain variable region of (1) above, wherein one or more, preferably one to several (e.g., 1, 2, 3, 4 or 5) amino acid residues are substituted and/or deleted and/or added and/or inserted in one or more (e.g., 1, 2, 3, 4, 5 or 6) amino acid sequences selected from the amino acid sequences shown in SEQ ID NOs:11 to 16, and wherein the antibody has a binding property equivalent to that of any one of the above-mentioned antibodies, or binds to wild type human CD81 competitively with any one of the above-mentioned antibodies. Here, the "equivalent binding property" means the same as above.

More preferably, in the antibody mentioned above, the CDRs (a-25), (b-25) and (c-25) are located in this order from the N-terminus of the light chain. Namely, the CDRs (a-25), (b-25) and (c-25) corresponds to CDR1, CDR2 and CDR3 of the light chain, respectively. Similarly, the CDRs (d-25), (e-25) and (f-25) are located in this order from the N-terminus of the heavy chain. Namely, the CDRs (d-25), (e-25) and (f-25) correspond to CDR1, CDR2 and CDR3 of the heavy chain, respectively.

An even more preferable example of the antibodies having the binding properties mentioned above is an antibody comprising:

(1) a light chain variable region comprising the amino acid sequence shown in SEQ ID NO:18 and a heavy chain variable region comprising the amino acid sequence shown in SEQ ID NO:20; or (2) the light chain and heavy chain variable region of (1) above, wherein one or more, preferably 1 to 20, more preferably 1 to 10, even more preferably one to several (e.g., 1, 2, 3, 4 or 5) amino acid residues are substituted and/or deleted and/or added and/or inserted in either or both of the amino acid sequences shown in SEQ ID NOs:18 and 20, and wherein the antibody has a binding property equivalent to that of any one of the above-mentioned antibodies, or binds to wild type human CD81 competitively with any one of the above-mentioned antibodies. Here, the "equivalent binding property" means the same as above.

Another preferable example of the antibodies having the binding properties mentioned above is an antibody that binds to the same or essentially the same epitope of wild type human CD81 as that to which the antibody comprising a light chain variable region comprising the amino acid sequence shown in SEQ ID NO:18 and a heavy chain variable region comprising the amino acid sequence shown in SEQ ID NO:20 binds. A more preferable example is an antibody that binds to the same or essentially the same epitope of wild type human CD81 as that to which the antibody comprising a light chain comprising the amino acid sequence shown in SEQ ID NO:30 and a heavy chain comprising the amino acid sequence shown in SEQ ID NO:32 binds. Here, "essentially the same epitope" mean the same as above.

The antibody of the present invention may also be an antibody that comprises at least one CDR selected from among the six CDRs (a-25) to (f-25) above, and binds to wild type human CD81 competitively with an antibody comprising all the six CDRs.

Furthermore, the antibody of the present invention may be an antibody that possesses a homology of 80% or more, preferably 90% or more, more preferably 95% or more, to the amino acid sequences of the light chain and heavy chain of an antibody comprising all the six CDRs (a-25) to (f-25) above, and binds to wild type human CD81 competitively with the antibody. Here, amino acid homology can be calculated in the same manner as the above.

(I) Production of Antibody

The antibody of the present invention can be any monoclonal antibody, as long as it binds to the particular peptide region of the wild type human CD81 mentioned above. Although the isotype of the antibody is not subject to limitation, it is preferably IgG, IgM or IgA, particularly preferably IgG. Also, the molecule type of the antibody is not subject to limitation, in addition to the entire antibody molecule, the antibody may, for example, be a fragment such as Fab, Fab', or $F(ab')_2$, a genetically engineered conjugate molecule such as scFv, scFv-Fc, minibody, or diabody, or a derivative thereof modified with a certain molecule, for example, a molecule having a stabilizing action such as polyethylene glycol (PEG), and the like.

Since the antibody of the present invention is used as a pharmaceutical product having humans as the subject of administration thereof, the antibody used in the present invention is an antibody whose risk of showing antigenicity when administered to a human has been reduced; to be specific, the antibody is a (fully) human antibody, a humanized antibody, a non-human (e.g., mouse, rat, rabbit)-human chimeric antibody and the like, particularly preferably a human antibody. A humanized antibody and a chimeric antibody can be prepared by genetic engineering technology according to the method described below. Although a (fully) human antibody can also be produced from human-human (or human-mouse) hybridoma, it is desirable to produce it using a phage display method or a human antibody-producing animal as described below (e.g., mouse), in order to stably supply the antibody in large amounts at low costs.

(II) Production Method of the Antibody of the Present Invention

The antibody of the present invention can be produced by the method described in the following Examples or a known method.

(i) Preparation of Antigen

The antigen used to prepare the antibody of the present invention may be the wild type human 0081 protein or partial peptide thereof, a (synthetic) peptide having one or more kinds of the same antigen determinant as that thereof and the like (hereinafter these are sometimes simply referred to as the antigen of the present invention).

The wild type human CD81 protein or a partial peptide thereof is produced by, for example, (a) preparing the same from a human tissue or cells, by a method known to the public or its modified method (b) chemically synthesizing the same by a publicly known method of peptide synthesis using a peptide synthesizer and the like, (c) culturing a transformant comprising a DNA that encodes wild type human CD81 or a partial peptide thereof, or (d) biochemically synthesizing the same with a nucleic acid that encodes wild type human CD81 or a partial peptide thereof as the template using a cell-free transcription/translation system.

(iia) Preparation of Human Antibody Using Phage Display Human Antibody Library

A human antibody can be produced by phage display (Hoogenboom and Winter, *J. Mod. Biol.*, 227:381 (1991); Marks et al, *J. Mol. Biol.*, 222:581 (1991); Cole et al, *Monoclonal Antibodies and Cancer Therapy*, Alan R. Liss, p. 77 (1985) and Boermer et al, *J. Immunol.*, 147(1):86-95 (1991)).

The method of preparing a phage display human antibody library include, but are not limited to, for example, the methods described below.

Although a phage used is not subject to limitation, filamentous phage (Ff bacteriophage) is normally preferably used. As the method of presenting a foreign protein on the phage surface, a method comprising expressing and presenting the foreign protein as a fusion protein with any of the coat proteins g3p, and g6p to g9p on the coat protein can be mentioned; and a method comprising fusing the foreign protein to the N-terminal side of g3p or g8p is often used. As the phage display vector, besides 1) one in which the foreign gene is introduced in the form of fusion gene with the coat protein gene of the phage genome, to allow all the coat proteins presented on the phage surface to be presented as a fusion protein with the foreign protein, 2) one in which the gene encoding the fusion protein is inserted separately from the wild-type coat protein gene to allow the fusion protein and the wild-type coat protein to be expressed simultaneously, and 3) an *E. coli* having a phagemid vector harboring the gene that encodes the fusion protein is infected with a helper phage having the wild-type coat protein gene to produce phage particles that express the fusion protein and the wild-type coat protein simultaneously, and the like can be mentioned. However, a phage display vector of the type 2) or 3) is used for the preparation of an antibody library, because in the case of 1), the capability of infection is lost when a large foreign protein is fused.

As a specific vector, those described by Holt et al. (*Curr. Opin. Biotechnol.*, 11: 445-449, 2000) can be mentioned as examples. For example, pCES1 (see *J. Biol. Chem.*, 274: 18218-18230, 1999) is an Fab-expressing phagemid vector wherein a DNA encoding the κL chain constant region allocated to downstream of the g3p signal peptide, and a DNA encoding CH3, His-tag, c-myc tag, and the amber stop codon (TAG) followed by the g3p coding sequence, allocated to downstream of the g3p signal peptide, are arranged under the control of one lactose promoter. When this is introduced to an *E. coli* having an amber mutation, Fab is presented onto the g3p coat protein, but when it is expressed in the HB2151 strain and the like, which do not have an amber mutation, a soluble Fab antibody is produced. As the scFv-expressing phagemid vector, for example, pHEN1 (*J. Mol. Biol.,* 222: 581-597, 1991) and the like are used.

Meanwhile as examples of the helper phage, M13-KO7, VCSM13 and the like can be mentioned.

And as another phage display vector, a vector that is designed as a DNA sequence comprising the cysteine-encoding codon is linked to each of the 3' end of the antibody gene and the 5' end of the coat protein gene to express the two genes simultaneously and separately (not in the form of a fusion protein), and to present the antibody onto the coat protein on the phage surface via S—S bonds between the introduced cysteine residues (CysDisplay™ technology of Morphosys Company) and the like, can be mentioned.

As the kind of human antibody library, a naive/non-immunized library, a synthetic library, an immunized library and the like can be mentioned.

The naive/non-immunized library is a library obtained by acquiring the $V_H$ and $V_L$ genes retained by a normal human by RT-PCR, and randomly cloning them into the above-described phage display vector. Normally, mRNA derived from lymphocytes of peripheral blood, bone marrow, tonsil and the like of a normal human, and the like are used as the template. A library prepared by selectively amplifying IgM-derived mRNA in which a class switch due to antigen sensitization is not undergoing, to avoid V gene biases such as clinical history, is particularly called a naive library. Representatively, the library of Cambridge Antibody Technology (see *J. Mol. Biol.,* 222: 581-597, 1991; *Nat. Biotechnol.,* 14: 309-314, 1996), the library of Medical Research Council (see *Annu. Rev. Immunol.,* 12: 433-455, 1994), the library of Dyax Corp. (see *J. Biol. Chem.,* 1999 (supra); *Proc. Natl. Acad. Sci. USA,* 14: 7969-7974, 2000) and the like can be mentioned.

A synthetic library is obtained by selecting a functional particular antibody gene in human B cells, and substituting a portion of antigen-binding region in a V gene segment, for example, CDR3 and the like, with DNAs encoding a random amino acid sequence of appropriate length, to construct a library. It is recognized to be excellent in antibody expression efficiency and stability because the library can be constructed with the combination of the V and $V_L$ genes, which produce functional scFv and Fab, since the beginning. Representatively, the HuCAL library of Morphosys AG (see *J. Mol. Biol.,* 296: 57-86, 2000), the library of Bioinvent (see *Nat. Biotechnol.,* 18: 852, 2000), the library of Crucell (see *Proc. Natl. Acad. Sci. USA,* 92: 3938, 1995; *J. Immunol. Methods,* 272: 219-233, 2003) and the like can be mentioned.

An immunized library is a library obtained by preparing an mRNA from lymphocytes collected from a human such as a patient with cancer, autoimmune disease, infectious disease and the like or a recipient of vaccination, having an elevated blood antibody titer against the target antigen, or from human lymphocytes and the like which are artificially immunized with the target antigen by the above-described in vitro immunization method, in the same manner as with the above-described naive/non-immunized library, and amplifying the $V_H$ and $V_L$ genes by RT-PCR, to construct a library. It is possible to obtain the desired antibody even from such libraries of relatively small size because the desired antibody gene is contained in the library already at the beginning.

The process for selecting an antibody against the target antigen by the phage display method is referred to as panning. To be specific, for example, a phage presenting an antigen-ic) specific antibody is concentrated by repeating a series of operations of bringing an antigen-immobilized carrier and a phage library into contact with each other, washing out the unbound phage, thereafter eluting the bound phage from the carrier, and infecting the phage to *E. coli* to proliferate it, about 3 to 5 times. As the carrier for immobilizing the antigen, various carriers used in ordinary antigen-antibody reactions or affinity chromatography, for example, insoluble polysaccharides such as agarose, dextran, and cellulose, synthetic resins such as polystyrene, polyacrylamide, and silicon, or microplates, tubes, membranes, columns, beads and the like comprising glass, metal and the like, and surface plasmon resonance (SPR) sensor chips, and the like can be mentioned. For the antigen immobilization, physical adsorption may be used, and a method using a chemical bond used to insolubilize and immobilize a protein or enzyme and the like is also acceptable. For example, a biotin-(strept)avidin system and the like are preferably used. For washing the unbound phage, a blocking solution such as BSA solution (once or twice), a PBS comprising a surfactant such as Tween (3 to 5 times) and the like can be used. There is also a report mentioning that the use of citrate buffer (pH 5) and the like is preferable for the washing. For elution of the specific phage, an acid (e.g., 0.1 M hydrogen chloride and the like) is normally used; cleavage with a specific protease (e.g., a gene sequence that encodes the trypsin cleavage site can be introduced into the linkage site between the antibody gene and the coat protein gene. In this case, *E. coli* infection and proliferation are possible even if all the coat protein is expressed in the form of a fusion protein because the wild-type coat protein is presented on the surface of the eluted phage), competitive elution with a soluble antigen, or elution by reduction of S—S bond (e.g., in the aforementioned CysDisplay™ the antigen-specific phage can be collected by dissociating the antibody and the coat protein by using a suitable reducing agent after performing panning) is also possible. When elution has been performed with an acid, the eluate is neutralized with Tris and the like, and the eluted phage is then infected to *E. coli,* which is cultured; after which the phage is collected by a conventional method.

After the phage presenting the antigen-specific antibody is concentrated by panning, the phage is infected to *E. coli* and the cells are sown onto a plate to perform cell cloning. The phage is again collected from the each clone, and the antigen binding activity is confirmed by the above-described antibody titer assay (e.g., ELISA, RTA and the like) or a measurement utilizing FACS or SPR.

Isolation and purification of the antibody from the selected phage clone that presents the antigen-specific antibody can be performed by, for example, when using a vector incorporating an amber stop codon at the linker site of the antibody gene and the coat protein gene as the phage display vector, infecting the phage to an *E. coli* that does not have amber mutation (e.g., HB2151 strain) to produce and secrete soluble antibody molecules in periplasm or the medium, lysing the cell wall with lysozyme and the like, collecting the extracellular fraction, and purifying using the same purification technique as described above. Provided that the His-tag or c-myc tag has been introduced in advance, the antibody can easily be purified by using Immobilized Metal Affinity Chromatography (IMAC) method, an anti-c-myc antibody column and the like. When cleavage with a specific protease is utilized in panning, the antibody molecule is separated from the phage surface by an action with the protease, so that the desired antibody can be purified by performing the same purification operation as above mentioned.

The affinity and avidity of the human antibody (e.g., scFv, Fab) thus obtained to the epitope region of wild type human CD81 is confirmed by the binding assays mentioned above using a polypeptide comprising the peptide region.

(iib) Preparation of Human Antibody Using Human Antibody-Producing Animal

Provided that a functional human Ig gene is introduced into a non-human warm-blooded animal having the endogenous immunoglobulin (Ig) gene knocked out (KO) therein, and that this animal is immunized with an antigen, a human antibody is produced in place of the antibody derived from the animal. Therefore, provided that an animal such as mice, for which a technique for producing a hybridoma has been established, is used, it is possible to acquire a fully human monoclonal antibody by the same method as the conventional method used to prepare a mouse monoclonal antibody. Namely, human monoclonal antibodies can be generated by using a human antibody-producing mouse (see *Immunol. Today,* 17: 391-397, 1996) obtained by crossing a mouse transfected with minigenes of the human Ig H chain and L chain using an ordinary transgenic (Tg) technique with a mouse wherein the endogenous mouse Ig gene has been inactivated using an ordinary KO technique (WO 93/12227, WO 92/03918, WO 94/02602, WO 94/25585, WO 96/34096 and WO 96/33735).

The hybridoma obtained by fusion of the anti-human CD81 antibody-producing cell obtained from the human antibody-producing mouse with a myeloma cell are cultured, and the anti-human CD81 antibody can be recovered from the culture supernatant and purified by conventional methods. The affinity and avidity of the human antibody thus obtained to the epitope region of wild type human CD81 is confirmed by the binding assays mentioned above using a polypeptide comprising the peptide region.

(iic) Preparation of Chimeric Antibody

As used herein, "chimeric antibody" means an antibody wherein the sequences of the variable regions of the H chain and L chain ($V_H$ and $V_L$) thereof are derived from a non-human animal species, and wherein the sequences of the constant regions ($C_H$ and $C_L$) are derived from human. The sequences of the variable regions are preferably derived from, for example, an animal species permitting easy preparation of a hybridoma, such as mouse, rat, rabbit and the like.

As examples of the method of preparing a chimeric antibody, the method described in U.S. Pat. No. 6,331,415 or a partially modified method thereof and the like can be mentioned.

Host cells are transformed with the chimeric H chain and chimeric L chain expression vector(s) obtained. As the host cells, animal cells, for example, Chinese hamster ovary (CHO) cells, monkey-derived COS-7 cells, Vero cells, rat-derived GHS cells and the like, in addition to the above-described mouse myeloma cells, can be mentioned. For the transformation, any method applicable to animal cells can be used, with preference given to electroporation method and the like. It is possible to isolate a chimeric monoclonal antibody by culturing the host cells in a medium suitable thereto for a given period, and thereafter collecting the culture supernatant and purifying it in the same manner as described above. Alternatively, it is also possible to obtain a chimeric monoclonal antibody easily and in large amounts from milk or eggs of transgenic animals which are produced by a conventional method using germ line cells of an animal such as bovine, goat, or fowl as the host cells, for which a transgenic technique has been established and a know-how of mass propagation as a domestic animal (domestic fowl) has been compiled. Furthermore, it is also possible to obtain a chimeric monoclonal antibody in large amounts from the seeds, leaves and the like of a transgenic plant, produced by using microinjection and electroporation into protoplast, the particle gun method and Ti-vector method for intact cells and the like, with cells of a plant such as corn, rice, wheat, soybean, or tobacco as the host cells, for which a transgenic technique has been established, and which is cultured in large amounts as a major crop.

(iii) Humanized Antibody

As used herein, "a humanized antibody" means an antibody wherein the sequences of all regions present in the variable region, other than the complementarity determining region (CDR), [i.e., framework region (FR) in constant region and variable region] are derived from a human, and wherein only the sequence of CDR is derived from another mammalian species. The other mammalian species is preferably an animal species, for example, mouse, rat, rabbit and the like, with which production of hybridomas can be easily performed.

As examples of the method of preparing a humanized antibody, the methods described in U.S. Pat. Nos. 5,225,539, 5,585,089, 5,693,761 and 5,693,762, EP 239400, WO 92/19759 or partially modified methods therefrom and the like can be mentioned. To be specific, DNAs that encode $V_H$ and $V_L$ derived from a non-human mammalian species (e.g., mouse) are isolated in the same manner as with the above-described chimeric antibody, after which sequencing is performed by a conventional method using an automated DNA sequencer (e.g., manufactured by Applied Biosystems Company and the like), and the nucleotide sequences obtained or deduced amino acid sequences therefrom are analyzed using a known antibody sequence database [for example, Kabat database (see Kabat et al., "Sequences of Proteins of Immunological Interest", edited by NIH, US Department of Health and Human Services, Public Health Service, 5th edition, 1991) and the like] to determine the CDR and FR of the two chains. A nucleotide sequence wherein the CDR encoding region of a nucleotide sequence that encodes the L chain and H chain of a human antibody having an FR sequence similar to the determined FR sequence is substituted with the determined nucleotide sequence that encodes the CDR of another animal species, is designed, and the nucleotide sequence is divided into fragments of about 20 to 40 bases, and a sequence complementary to the nucleotide sequence is divided into fragments of about 20 to 40 bases so that they alternatively overlap with the aforementioned fragments. It is possible to construct DNAs that encode $V_H$ and $V_L$ having human-derived FR and a CDR derived from another mammalian species by synthesizing individual fragments using a DNA synthesizer, and hybridizing and ligating them in accordance with conventional methods. In order to transfer a CDR derived from another mammalian species into human-derived $V_H$ and $V_L$ more quickly and more efficiently, it is preferable to use PCR-based site directed mutagenesis. As examples of such a method, the sequential CDR grafting method described in JP-A-5-227970 and the like can be mentioned.

It should be noted that in preparing a humanized antibody by a method as described above, the antigen binding activity may sometimes decrease, compared with the original non-human antibody, if the amino acid sequence of CDR alone is transplanted to the template human antibody FR. In such cases, it is effective to transplant some FR amino acids around the CDR in combination. The non-human antibody FR amino acid to be transplanted may be an amino acid residue that is important to the maintenance of the steric structure of each CDR; such an amino acid residue can be deduced by a steric structure estimation using a computer.

It is possible to obtain cells or transgenic animal/plant that produces a humanized antibody by ligating the thus-obtained DNAs encoding $V_H$ and $V_L$ to DNAs encoding human-derived $C_H$ and $C_L$, respectively, and introducing the ligated product into suitable host cells.

An alternative method of preparing a humanized antibody without using CDR grafting wherein mouse CDRs are grafted into variable regions of a human antibody is, for example, a method comprising determining which is an amino acid residue that can be substituted in a non-human variable region, on the basis of a conserved structure-function correlation between antibodies. This method can be carried out as described in, for example, EP 0571613 B1, U.S. Pat. Nos. 5,766,886, 5,770,196, 5,821,123 5,869,619 and the like. Provided that the amino acid sequence information on each of the $V_H$ and $V_L$ of the original non-human antibody, preparation of a humanized antibody using the method can easily be performed by utilizing, for example, the contract antibody preparation service provided by Xoma.

A humanized antibody, like a chimeric antibody, can be modified to scFv, scFv-Fc, minibody, dsFv, Fv and the like by using genetic engineering techniques; and they can be produced in a microorganism such as *E. coli* or yeast by using a suitable promoter.

The affinity and avidity of the humanized antibody thus obtained to the epitope region of wild type human CD81 is confirmed by the binding assays mentioned above using a polypeptide comprising the peptide region.

(III) Optimization of Antibody

The anti-human CD81 antibodies of the invention mentioned above may be readily prepared to include various changes, substitutions, insertions, and deletions. For example, to maximize the expression level of an antibody, the nucleotide sequences of the antibody gene may be optimized so as to match the codon usage frequency of the cell used for antibody expression. Additional modifications to enhance antibody stability include modification of IgG4 to replace the serine at residue 228 in the hinge region with proline as described below. As other modifications, substitutions as required to optimize efficiency in conjugating the antibody with a drug can be mentioned. For example, an antibody may be modified at its carboxyl terminus to include amino acids for drug attachment, for example, one or more cysteine residues may be added. The constant regions may be modified to introduce sites for binding of carbohydrates or other moieties.

Mutants of anti-CD81 antibodies of the invention may be produced using standard recombinant techniques, including site-directed mutagenesis, or recombination cloning.

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable regions are mutated to generate all possible amino substitutions at each site. The antibody variants thus generated are displayed as fused proteins with a coat protein g3p of filamentous phage M13 on phages. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Once such variants are generated, the panel of variants is subjected to screening as described herein and antibodies with superior properties in one or more relevant assays may be selected for further development. Nucleic acid molecules encoding amino acid sequence variants of the anti-human CD81 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-human CD81 antibody.

Preferred affinity matured antibodies have an affinity which is five times, more preferably 10 times, even more preferably 20 or 30 times greater than the starting antibody from which the matured antibody is prepared.

IgG4 Mutation

When an IgG4 antibody is administered to human or some animals, a phenomenon that the serum concentration of IgG4 antibody is reduced due to swapping with an endogenous IgG4 has been observed. It has been known that this IgG4 exchange is inhibited by the point mutation of Ser at residue 228 with Pro (*Mol. Immunol.* 30, 105, 1993, *Protein Sci.* 6, 407, 1997, *Mol. Immunol.* 38, 1, 2001, *Nat. Biotechnol.* 27, 767, 2009).

(IV) Confirmation of Therapeutic Effect of Antibody

The antibody of the present invention has a suppressive effect on T lymphocyte migration. This action is detected using a widely known evaluation system for lymphocyte function. For example, the effect on T lymphocyte migration is evaluated by bringing human peripheral blood mononuclear cells (PBMCs) cultured in the presence of cytokines (e.g., PHA, IL-2, TNF-α, IL-22, IL-7 and VIP) into contact with a test antibody, stimulating the migration of PBMCs (e.g., by adding a chemokine, stromal cell-derived factor 1 (SDF-1; also known as CXCL12), and determining inhibition of the migration (see, for example, Blood 2009 August 13; 114(7): 1366-1373). To be specific, a cell migration experiment described below can be used.

As the lymphocytes, established cell lines such as Jurkat cells (Clone E6-1, ATCC Number TIB-152), and cells derived from human peripheral blood can be used. Human peripheral blood-derived cells are commercially available (KAC Co., Ltd. and the like). Alternatively, human peripheral blood-derived cells can also be prepared by isolating a mononuclear cell fraction containing monocytes and lymphocytes from a peripheral blood of a healthy human using Ficoll/Paque density gradient centrifugation according to The Journal of Immunology, 147, 2251 (1991).

Cell Migration Experiment (Chemotaxis Assay)

The ability of an antibody or a functional fragment thereof to inhibit its antigen's function relating to cell migration can be evaluated using a cell migration experiment (chemotaxis assay). In general, a cell migration experiment is performed by separating appropriate cells such as leukocytes (e.g., lymphocytes, eosinophils, basophils) and a chemotactic factor by a barrier (e.g., endothelium, filter), and monitoring the migration of the cells toward or across the barrier. For example, the suppressive effect on cell migration. of a test antibody can be examined by adding a culture medium containing a chemotactic factor such as SDF-1 to a well of 96-well migration plate (the first chamber), putting a transwell having the bottom surface consisting of a cell-permeable macroporous membrane (the second chamber) onto the well, adding the test antibody and the cells, measuring the migration of the cells from the second chamber to the first chamber and comparing the extent of migration with that in the absence of antibody or in the presence of a non-specific antibody (*Immunol. Invest.* 17: 625-677 (1988)).

(V) Production of Recombinant Antibody

Any production system can be used for the production of the antibody used in the present invention. The production systems for producing antibodies include in vitro and in vivo production systems. In vitro production systems include production systems using eukaryotic cells and those using prokaryotic cells.

Antibody genes constructed as described above may be expressed and obtained in a known method. In the case of mammalian cells, expression may be accomplished using a DNA in which a commonly used useful promoter, the antibody gene to be expressed, and the poly A signal at 3' downstream thereof have been functionally linked or a vector containing said DNA. Examples of the promoter/enhancer include human cytomegalovirus immediate early promoter/enhancer.

Additionally, as the promoter/enhancer which can be used for expression of antibody for use in the present invention, there are viral promoters/enhancers such as retrovirus, polyoma virus, adenovirus, and simian virus 40 (SV40), and promoters/enhancers derived from mammalian cells such as human elongation factor 1α. (hEF1α).

For example, expression may be readily accomplished by the method of Mulligan et al. (Nature (1979) 277, 108) when SV40 promoter/enhancer is used, or by the method of Mizushima et al. (Nucleic Acids Res. (1990) 18, 5322) when hEF1α. promoter/enhancer is used.

In the case of *E. coli*, expression may be conducted by functionally linking a commonly used useful promoter, a signal sequence for antibody secretion, and the antibody gene to be expressed, followed by expression thereof. As the promoter, for example, there can be mentioned lacZ promoter and araB promoter. The method of Ward et al. (Nature (1989) 341, 544-546; FASEB J. (1992) 6, 2422-2427) may be used when lacZ promoter is used, and the method of Better et al. (Science (1988) 240, 1041-1043) may be used when araB promoter is used.

As the signal sequence for antibody secretion, when produced in the periplasm of *E. coli*, the pelB signal sequence (Lei, S. P. et al., J. Bacteriol. (1987) 169, 4379) can be used. After separating the antibody produced in the periplasm, the structure of the antibody is appropriately refolded before use (see, for example, WO 96/30394).

As the origin of replication, there can be used those derived from SV40, polyoma virus, adenovirus, bovine papilloma virus (BPV) and the like. Furthermore, for the amplification of the gene copy number in the host cell system, expression vectors can include as selectable markers the aminoglycoside transferase (APH) gene, the thymidine kinase (TK) gene, *E. coli* xanthine guaninephosphoribosyl transferase (Ecogpt) gene, the dihydrofolate reductase (dhfr) gene and the like.

When the eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as Xenopusoocytes, or (3) insect cells such as sf9, sf21, and Tn5. Known plant cells include, for example, those derived from *Nicotiana tabacum*, which is subjected to callus culture. Known fungal cells include yeasts such as the genus *Saccharomyces*, more specifically *Saccharomyces cerevisiae*, or filamentous fungi such as the genus *Aspergillus*, more specifically *Aspergillus niger.*

When the prokaryotic cells are used, there are the production systems which employ bacterial cells. Known bacterial cells include *Escherichia coli* (*E. coli*), and *Bacillus subtilis.*

By introducing via transformation the gene of the desired antibody into these cells and culturing the transformed cells in vitro, the antibody can be obtained. Culturing is conducted in the known methods. For example, as the culture medium DMEM, MEM, RPMI1640, and IMDM can be used, and serum supplements such as fetal calf serum (FCS) may be used in combination. In addition, antibodies may be produced in vivo by implanting cells into which the antibody gene has been introduced into the abdominal cavity of an animal and the like.

As in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). Also, as insects, silkworms can be used.

When plants are used, tabacco, for example, can be used.

Antibody genes are introduced into these animals or plants, and the antibodies are produced in such animals or plants, and recovered. For example, an antibody gene is inserted into the middle of the gene encoding protein which is inherently produced in the milk such as goat β-casein to prepare fusion genes. DNA fragments containing the fusion gene into which the antibody gene has been inserted are injected into a goat embryo, and the embryo is introduced into a female goat. The desired antibody is obtained from the milk produced by the transgenic goat born to the goat who received the embryo or off springs thereof. In order to increase the amount of milk containing the desired antibody produced by the transgenic goat, hormones may be given to the transgenic goat as appropriate. (Ebert, K. M. et al., Bio/Technology (1994) 12, 699-702).

When silkworms are used, baculovirus into which the desired antibody gene has been inserted is infected to the silkworm, and the desired antibody can be obtained from the body fluid of the silkworm (Maeda, S. et al., Nature (1985) 315, 592-594). Moreover, when tabacco is used, the desired antibody gene is inserted into an expression vector for plants, for example pMON 530, and then the vector is introduced into a bacterium such as *Agrobacterium tumefaciens*. The bacterium is then infected to tabacco such as *Nicotiana tabacum* to obtain the desired antibody from the leaves of the tabacco (Julian, K.-C. Ma et al., Eur. J. Immunol. (1994) 24, 131-138).

When antibody is produced in in vitro or in vivo production systems, as described above, DNA encoding the heavy chain (H chain) or the light chain (L chain) of antibody may be separately integrated into an expression vector and the hosts are transformed simultaneously, or DNA encoding the H chain and the L chain may be integrated into a single expression vector and the host is transformed therewith (see International Patent Application WO 94-11523).

Antibodies for use in the present invention may be antibody fragments or modified versions thereof as long as they are preferably used. For example, as fragments of antibody, there may be mentioned Fab, F(ab')2, Fv or single-chain Fv (scFv) in which Fv's of H chain and L chain were ligated via a suitable linker. Specifically antibodies are treated with an enzyme, for example, papain or pepsin, to produce antibody fragments, or genes encoding these antibody fragments are constructed, and then introduced into an expression vector, which is expressed in a suitable host cell (see, for example, Co, M. S. et al., J. Immunol. (1994) 152, 2968-2976; Better, M. and Horwitz, A. H., Methods in Enzymology (1989) 178, 476-496, Academic Press, Inc.; Plueckthun, A. and Skerra, A., Methods in Enzymology (1989) 178, 476-496, Academic Press, Inc.; Lamoyi, E., Methods in Enzymology (1986) 121, 652-663; Rousseaux, J. et al., Methods in Enzymology (1986) 121, 663-669; Bird, R. E. et al., TIBTECH (1991) 9, 132-137).

scFv can be obtained by ligating the V region of H chain and the V region of L chain of antibody. In the scFv, the V region of H chain and the V region of L chain are preferably ligated via a linker, preferably a peptide linker (Huston, J. S. et al., Proc. Natl. Acad. Sci. U.S.A. (1988) 85, 5879-5883). The V region of H chain and the V region of L chain in the scFv may be derived from any of the above-mentioned antibodies. As the peptide linker for ligating the V regions, any single-chain peptide comprising, for example, 12-19 amino acid residues may be used.

DNA encoding scFv can be obtained using DNA encoding the H chain or the H chain V region of the above antibody and DNA encoding the L chain or the L chain V region of the above antibody as the template by amplifying the portion of the DNA encoding the desired amino acid sequence among the above sequences by the PCR technique with the primer pair specifying the both ends thereof, and by further amplifying the combination of DNA encoding the peptide linker portion and the primer pair which defines that both ends of said DNA be ligated to the H chain and the L chain, respectively.

Once DNA encoding scFv are constructed, an expression vector containing them and a host transformed with said expression vector can be obtained by the conventional methods, and scFv can be obtained using the resultant host by the conventional methods.

These antibody fragments can be produced by obtaining the gene thereof in a similar manner to that mentioned above and by allowing it to be expressed in a host. "Antibody" as used in the claim of the present application encompasses these antibody fragments.

As modified antibodies, antibodies associated with various molecules such as polyethylene glycol (PEG) can be used. "Antibody" as used in the claim of the present application encompasses these modified antibodies. These modified antibodies can be obtained by chemically modifying the antibodies thus obtained. These methods have already been established in the art.

Antibodies produced and expressed as described above can be separated from the inside or outside of the host cell and then may be purified to homogeneity. Separation and purification of the antibody for use in the present invention may be accomplished by affinity chromatography. As the column used for such affinity chromatography, there can be mentioned Protein A column and Protein G column. Examples of the carriers used in the Protein A column are Hyper D, POROS, Sepharose F. F. and the like. Alternatively, methods for separation and purification conventionally used for proteins can be used without any limitation. Separation and purification of the antibody for use in the present invention may be accomplished by combining, as appropriate, chromatography other than the above-mentioned affinity chromatography, filtration, ultrafiltration, salting-out, dialysis and the like. Chromatography includes, for example, ion exchange chromatography, hydrophobic chromatography, gel-filtration and the like. These chromatographies can be applied into HPLC (High Performance Liquid Chromatography). Alternatively, reverse-phase HPLC can be used.

The concentration of antibody obtained above can be determined by the measurement of absorbance or by the enzyme-linked immunosorbent assay (ELISA) and the like. Thus, when absorbance measurement is employed, the antibody for use in the present invention or a sample containing the antibody is appropriately diluted with PBS(−) and then the absorbance is measured at 280 nm, followed by calculation using the absorption coefficient of 1.35 OD at 1 mg/ml. When the ELISA method is used, measurement is conducted as follows. Thus, 100 μl of goat anti-human IgG (manufactured by TAGO) diluted to 1 μg/ml in 0.1 M bicarbonate buffer, pH 9.6, is added to a 96-well plate (manufactured by Nunc), and is incubated overnight at 4° C. to immobilize the antibody.

After blocking, 100 μl each of appropriately diluted antibody for use in the present invention or a sample containing the antibody, or 100 μl of human IgG (manufactured by CAPPEL) as the standard is added, and incubated at room temperature for 1 hour. After washing, 100 μl of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550, (manufactured by Bio-Rad) to calculate the concentration of the desired antibody.

(VI) Pharmaceutical Composition Containing the Antibody of the Present Invention The invention also provides an agent for the prophylaxis and/or treatment of inflammatory bowel diseases (IBD), multiple sclerosis, psoriasis, or hematological cancers. The term "treatment" includes not only complete cure but also amelioration of a symptom. It is known that CD81 is overexpressed in an IBD patient and an anti-CD81 antibody is useful for preventing, ameliorating or treating IBD. Herein, "inflammatory bowel diseases (IBD)" means diseases including ulcerative colitis and Crohn's disease.

Since the present inventors obtained new findings that the anti-CD81 antibodies suppressed T cell migration, the antibody of the present invention is also useful for preventing, improving or treating a disease associated with T cell migration such as multiple sclerosis and psoriasis.

Since the antibody of the present invention does not enhance the production of cytokines such as interleukin-2 from T cells, the pharmaceutical composition containing the antibody does not cause adverse side effects due to cytokine overproduction. The effect on the cytokine production in lymphocytes can be determined by a known method, for example, the quantification of cytokines in culture supernatants of lymphocytes cultured under various conditions using ELISA or intracellular cytokine staining of the lymphocytes after treatment, as described in Nature Immunology, VOLUME 8 NUMBER 9 September 2007, 942.

The present inventors clarified a cytotoxic effect of the antibody of the present invention on cancer cells derived from patients with hematological cancer, and found that the antibody of the present invention is useful as a prophylactic, ameliorating or therapeutic agent for hematological cancers. According to the WHO Classification, hematological cancers are classified into leukemias, malignant lymphoma, multiple myeloma, and myelodysplastic syndrome. Leukemias are further classified into acute myelogenous leukemia, acute lymphatic leukemia, chronic myelogenous leukemia, and chronic lymphatic leukemia. Malignant lymphomas are classified into Hodgkin's lymphoma and non-Hodgkin's lymphoma.

Acute myelogenous leukemia is the most prevalent type of adult leukemia. Although acute lymphatic leukemia is relatively prevalent in children, it occurs at a certain incidence in adults as well. Chronic myelogenous leukemia is a disease for which therapeutic outcomes have improved dramatically in recent years. Chronic lymphatic leukemia is a type of leukemia relatively prevalent in Europe and the US, but not less prevalent in Japanese. Of malignant lymphomas, non-Hodgkin's lymphomas include adult T cell lymphoma, lymphoblastic lymphoma, diffuse large-cell lymphoma, Burkitt's lymphoma, follicular lymphoma, MALT lymphoma, peripheral T cell lymphoma, mantle cell lymphoma and the like. MALT lymphoma and follicular lymphoma are tumors of low malignancy that advances so slowly that no major advance occurs during many years. In contrast, Burkitt's lymphoma, lymphoblastic lymphoma and adult T cell lymphoma are tumors of extremely high malignancy that aggravate week by week. Other types positioned therebetween are peripheral T cell lymphoma, diffuse large-cell lymphoma, and mantle cell lymphoma. These tumors advance month by month. Multiple myeloma is a type of tumor in the stage of plasma cells resulting from maturation of B lymphocytes to produce immunoglobulins. Myelodysplastic syndrome generically refers to a class of diseases characterized by morphological and functional abnormalities of bone marrow stem cells.

Available treatments for hematological cancers include chemotherapies, radiotherapies, molecule-targeting treatments, and high-dose chemotherapies in combination with hematopoietic stem cell transplantation. While pediatric acute lymphatic leukemia is treatable with a long survival rate of 80%, adult acute lymphatic leukemia has a low long survival rate of 15-35%, although complete remission is achieved in 60-80% of the patients. The therapeutic outcomes for chronic lymphatic leukemia have been improving since the advent of Gleevec (imatinib mesylate). Improved therapeutic outcomes have been noted in Hodgkin's lymphoma and non-Hodgkin's lymphoma of low or moderate malignancy. Meanwhile, in adult T cell lymphoma, various therapies fail to produce improved therapeutic outcomes, the median survival time being about 1 year (IGAKU NO AYUMI, Vol. 212, No. 5, pp. 461-466, 2005). Lymphoblastic lymphoma is a set of diseases classified as non-Hodgkin's lymphoma of high malignancy. For Burkitt's lymphoma, the prognosis has been improved by short-time high-dose chemotherapy; the 2-year survival rate is currently about 70% or more, demonstrating improved therapeutic outcomes (Magrath, I. et al., J. Clin. Oncol., 14:925-943, 1996; Mead, G. M. et al., Ann. Oncol., 13:1264-1274, 2002); however, the 3-year survival rate remains low at 49%, so that a further improvement in the therapeutic outcomes is needed (Thomas D. A. et al., J. Clin. Oncol., 17:2461-2470, 1999). In diffuse large-cell lymphoma, a combination therapy with an anti-CD20 antibody (rituximab) and CHOP therapy (cyclophosphamide, doxorubicin, vincristine, prednisolone) is becoming a standard treatment with improved therapeutic outcomes for young low-risk patients in the progression stage. However, for young high-risk patients in the progression stage, no therapy surpassing CHOP therapy is available. Regarding the treatment of multiple myeloma, anticancer agents are somewhat effective, but this disease is highly malignant so that the treatment is not as effective as for leukemia and lymphoma. For myelodysplastic syndrome, the 5- to 10-year survival rate is about 30-40%. Hematological cancers of high malignancy for which further improvements in the therapeutic efficacy are expected include acute myelogenous leukemia, acute lymphatic leukemia, lymphoblastic lymphoma, diffuse large-cell lymphoma, Burkitt's lymphoma, mantle cell lymphoma, peripheral T cell lymphoma, adult T cell lymphoma, multiple myeloma, myelodysplastic syndrome and the like.

As stated above, no therapeutic methods or drugs are available with satisfactory therapeutic efficacy for hematological cancers of moderate to high malignancy; there is a demand for a novel therapeutic method and drug. It was found that anti-CD81 antibodies, whose potential as therapeutic drugs for hematological cancers has been unclear so far, have cytotoxic effects on some types of hematological cancers for which the therapeutic efficacy is lacked, i.e., Jurkat cells (a cancer cell line derived from a patient with acute lymphatic leukemia) and Ramos cells (a cancer cell line derived from a patient with Burkitt's lymphoma), based on their complement-dependent cytotoxicity. The finding that the anti-CD81 antibody exhibits a cytotoxic effect on cancer cells was not known so far.

Accordingly, the present invention also provides a prophylactic, ameliorating or therapeutic agent for hematological cancers with the antibody of the present invention as an active ingredient, preferably a prophylactic, ameliorating or therapeutic agent for hematological cancers of high malignancy.

The present invention is applicable not only to hematological cancers, but also to any type of cancer cell that expresses CD81. Therefore, drugs with the antibody of the present invention as an active ingredient are effective as a prophylactic, ameliorating or therapeutic agent for cancers caused by CD81-expressing cancer cells.

The agent containing the anti-CD81 antibody as an active ingredient is itself administered as an agent formulated by a known manufacturing pharmaceutical method. For example, it can be used in the form of an injection solution of a sterile solution or suspension with water or other pharmaceutically acceptable liquids. Further, it is considered to be formulated by being properly mixed with pharmacologically acceptable carriers or media, such as sterile water, a physiological saline solution, an emulsifying agent, a suspending agent, a surfactant, a stabilizer, a vehicle and a preservative in the unit dosage form required for formulation, which is generally approved. The amount of the active ingredient in these pharmaceutical preparations is adjusted such that an appropriate volume in the prescribed range is obtained.

The sterile composition for injection can be formed according to ordinary formulation using a vehicle such as distilled water for injection. Examples of the aqueous solution for injection include a physiological saline solution and isotonic solutions containing glucose and other auxiliaries such as D-sorbitol, D-mannose, D-mannitol and sodium chloride. An appropriate solubilizer, for example, an alcohol such as ethanol polyalcohol such as propylene glycol or polyethylene glycol, a nonionic surfactant such as polysorbate 80™ or HCO-50 may be used in combination.

Examples of oil include sesame oil and soybean oil, and benzyl benzoate or benzyl alcohol may be used in combination as a solubilizer. A buffering agent such as a phosphate buffer or a sodium acetate buffer, a soothing agent such as procaine hydrochloride, a stabilizer such as benzyl alcohol, phenol and an antioxidant may be incorporated. The thus-formed injection solution is usually filled in an appropriate ampule.

Regarding the agent containing the anti-CD81 antibody as an active ingredient, both of the oral administration and the parenteral administration are possible. The parenteral administration is preferable. Specific examples thereof include an injection solution dosage form, a transnasal dosage form, a transpulmonary dosage form, a percutaneous dosage form and the like. Regarding examples of the injection solution dosage form, systemic or local administration can be conducted by intravenous injection, intramuscular injection, intraperitoneal injection, subcutaneous injection or the like.

The dose can properly be selected depending on the age and condition of patients. For example, the dose can be selected in the range of from 0.0001 mg to 1,000 mg per kilogram of the body weight for one administration. Alternatively, the dose can be selected in the range of from 0.001 to 100,000 mg/body for a patient. However, the therapeutic agent of the invention is not limited by these doses.

The present invention is explained in more detail in the following by referring to Examples, which are not to be construed as limitative.

EXAMPLES

Example 1

Preparation of Human CD81 Antibody (1) Selection of Human Anti-Human CD81 Antibody Fragment A complete human antibody library n-CoDeR (*Nature Biotechnol.* 18: 852-856, 2000; WO98/32845) was screened for specific binding with human CD81, using human CD81 protein and human CD9 protein having a homology with CD81, or human CD81-expressing and -non-expressing cells to obtain human antibody fragments (scFv) specifically binding with human CD81. First, phages bound to biotinylated CD81 protein in the presence of competitive CD9 protein were recovered using streptoavidin-labeled magnetic beads. Unbound phages were washed out and the bound phages were eluted by trypsin treatment. Panning was carried out three times, and the selected phage library was expressed as an antibody fragment in *E. coli*. Antibody fragments that bind to CD81-expressing cells but do not bind to CD81-non-expressing cells were screened out using FMAT (Fluorometric Microvolume Assay Technology). FMAT is performed by adding antibody fragments to the cells immobilized on the wells of 384-well culture plate, and detecting its binding using a fluorescent-labeled anti-scFv antibody. As a result of the screening, two human CD81-specific human antibody fragments were selected. The nucleotide sequences (scFv-002-A07: SEQ ID NO:33, scFv-005-C01: SEQ ID NO:35) and the deduced amino acid sequences (scFv-002-A07: SEQ ID NO:34, scFv-005-C01: SEQ ID NO:36) of these fragments were determined by sequencing.

(2) Production of Anti-Human CD81 Antibody

Using the sequence information of the fragments obtained (1) above, anti-human CD81 antibody genes (heavy chain variable region ($V_H$): SEQ ID NO:9 (002-A07); SEQ ID NO:19 (005-C01) and light chain variable region ($V_L$): SEQ ID NO:7 (002-A07); SEQ ID NO:17 (005-C01)) were prepared by a known method (*Nat Biotechnol.*, 18, 852-856, 2000), amplified by PCR using a set of primers having BsmI and NheI recognition sites. The amplified fragments were digested with BsmI and NheI and subcloned into pCEP4 (Invitrogen)-derived vectors. In the heavy chain expression vector, a genomic region of mutant human γ4 chain wherein the 228th Ser is substituted with Pro (S228P) is inserted, and in the light chain expression vector, a genomic region of human λ chain is inserted. Thus constructed heavy and light chain expression vectors were co-transfected into HEK293-EBNA cells (ATCC-CRL-10852) using FuGene6 (Roche) according to the manufacture's protocol and the cells were cultured. After 6 days culture, the IgG4 antibodies were purified from the culture supernatants. Briefly, the culture solution was centrifuged and the supernatant was subjected to protein A chromatography. The purified material was dialyzed to 10 mM NaP buffer (0.15 M NaCl, pH 6.5). The 002-A07 IgG4 antibody thus obtained has the heavy chain consisting of the amino acid sequence shown in SEQ ID NO:28 and the light chain consisting of the amino acid sequence shown in SEQ ID NO:26. The 005-C01 IgG4 antibody thus obtained has the heavy chain consisting of the amino acid sequence shown in SEQ ID NO:32 and the light chain consisting of the amino acid sequence shown in SEQ ID NO:30.

Experimental Example 1

Binding Activity of Anti-CD81 Antibody on CD81-Expressing Cells (1) Cell Preparation Based on known information (*JOURNAL OF VIROLOGY.*, 79, 4316-4328, 2005), Jurkat E6.1 cells and human PBMC (Peripheral Blood Mononuclear cells) were used as human CD81-expressing cells to confirm binding of the antibodies of the present invention obtained in Example 1 to the human CD81-expressing cells. Jurkat E6.1 cells were purchased from European Collection of Cell Cultures (ECACC) (Cat No. 88042803). Human PBMC were purchased from KAC Co., Ltd. (KAC). These cells were collected by centrifugation (4,000 rpm, 3 min, 4° C.) and suspended in FACS staining buffer (phosphate buffer, 0.09% sodium azide, 1% bovine serum albumin (BSA: Hyclone Laboratories)). The number of viable cells was counted using trypan blue and $10^6$ cells/100 μl were added in an eppendorf tube.

(2) Cell Staining

To the cells prepared in (1) above was added the anti-human CD81 antibody (002-A07 or 005-C01) prepared in Example 1 or a human IgG4 (Acris) as a control (0.1 μg), and the cells were incubated for 20 min at 4° C. After washing the cells with FACS staining buffer, PE (phycoerythrin)-labeled anti-human IgG4 antibody (Beckman coulter; 0.05 μg) was added to the cells and incubated for 15 min at 4° C. After washing with FACS staining buffer twice, the cells were centrifuged (4,000 rpm, 3 min, 4° C.), the supernatant was removed and the precipitated cells were fixed with BD Cytefix/Cyteperm buffer (BD Biosciences). After washing, buffer was changed to PBS (NACALAI TESQUE, INC.). The binding ratio (%) of the anti-human CD81 antibody to the cells was analyzed by flow cytometry using FACS Calibur (BD Biosciences) and calculated as the percentage of cells having a PE-derived fluorescent intensity greater than that observed when the control IgG4 is used. The results are shown in Table 1. 002-A07 and 005-C01 strongly bound to Jurkat E6.1 cell and human PBMC.

TABLE 1

Binding of anti-human CD81 antibodies to Jurkat and PBMC.

| | PBMC | Jurkat |
|---|---|---|
| | Binding ratio to cells (%) | |
| control IgG4 | 1 | 1 |
| 002-A07 | 99 | 100 |
| 005-C01 | 98 | 100 |

The data presented are representative of three individual experiments.

Experimental Example 2

Suppressive Effect of Anti-Human CD81 Antibody on Chemotaxis of Jurakat Cells (1) Subculture of Jurkat Cells Jurkat E6.1 cells (purchased from ECACC: Cat No. 88042803) were maintained in RPMI1640 medium (GIBCO) supplemented with 10% fetal calf serum (FCS: Hyclone Laboratories) in humidified incubators in 5% $CO_2$ at 37° C. Cell density was kept between $2\times10^5$ and $1\times10^6$ cells/ml by diluting with the medium.

(2) Antibody Treatment

Jurkat E6.1 cells were suspended at $4\times10^6$ cells/ml in chemotaxis medium (RPMI1640 (GIBCO) containing 0.5% BSA (SIGMA), 50 mM HEPES (GIBCO)). The anti-human CD81 antibody (002-A07 or 005-C01) or control human IgG4 (Acris Antibodies GmbH) was added to the cells at the final concentrations described in Table 2. The cells were incubated for 2 hours in humidified incubators in 5% $CO_2$ at 37° C.

(3) chemotaxis Assay

Chemotaxis was examined using a 96-well chemotaxis chamber (Corning Inc, 5 μm pore size). The lower wells were filled with 235 μl of chemotaxis medium in the presence of 10 ng/ml SDF-1 (PEPROTECH). 75 μl of preincubated Jurkat cells with or without anti-human CD81 antibody were loaded onto the upper wells and incubated for 2 hours in humidified incubators in 5% $CO_2$ at 37° C. After incubation, 50 μl of lower well cell suspension was transferred to 96 well black plate (Corning Inc) and added 50 μl of ATP lite (Perkin Elmer). The number of the migrated cells was calculated by measuring luminescence intensity using Envision 2102 multilabelreader (Perkin Elmer).

(4) Analysis of Chemotaxis Assay

Percent Chemotaxis was calculated as the percentage of the number of the migrated Jurkat cells when the anti-human CD81 antibody was added, to the number of the migrated Jurkat cells when control IgG4 was added. As a result, both anti-human CD81 antibodies inhibited chemotaxis of Jurkat cells (Table 2). Since the suppressing effect of 002-A07 and 005-C01 on T cell migration of Jurkat cells was observed, it was confirmed that the anti-CD81 antibodies (002-A07 and 005-C01) can be a therapeutic agent of IBD.

TABLE 2

Suppressive effect of 002-A07 and 005-C01 on chemotaxis of Jurkat cells

| | Jurkat cell chemotaxis (%) antibody conc. (μg/ml) | | | | |
|---|---|---|---|---|---|
| | 1 | 0.5 | 0.2 | 0.04 | 0.005 |
| control IgG4 | 100 | 100 | 100 | 100 | 100 |
| 002-A07 | 18 | 9 | 20 | 51 | 95 |
| 005-A01 | 20 | 42 | 44 | 82 | 102 |

The data presented are average value of three individual experiments.

Experimental Example 3

Suppressive Effect of Anti-Human CD81 Antibody on Chemotaxis of Human PBMC (Peripheral Blood Mononuclear Cells)

Suppressive effect of anti-human CD81 antibodies on chemotaxis of human PBMC was examined according to the method described in Biologicals, 2007 October; 35(4):227-33, Epub 2007 Aug. 28.

(1) Cell Preparation

Human PBMC was purchased from KAC. According to the attached information from KAC, 60% of the human PBMC used was T cells (CD3-positive cells). The human PBMC were maintained in RPMI1640 medium (GIBCO) supplemented with 10% fetal calf serum (FCS: Hyclone Laboratories) in humidified incubators in 5% $CO_2$ at 37° C. The cells ($1\times10^6$ cells/ml) were incubated with 5 μg/ml PHA (phytohemagglutinin, Wako) and 50 ng/ml human recombinant IL-2 (R&D system) for 4 days in humidified incubators in 5% $CO_2$ at 37° C.

(2) Antibody Treatment

Human PBMC were suspended at $4\times10^6$ cells/ml in chemotaxis medium (RPMI1640 (GIBCO) containing 0.5% BSA (SIGMA), 50 mM HEPES (GIBCO)). The anti-human CD81 antibody (002-A07 or 005-C01) or control human IgG4 (Acris Antibodies GmbH) was added to the cells at the concentrations described in Table 3. The cells were incubated for 2 hours in humidified incubators in 5% $CO_2$ at 37° C.

(3) Chemotaxis Assay

Chemotaxis was examined using a 96-well chemotaxis chamber (corning coster, 5 μm pore size). The lower wells were filled with 235 μl of chemotaxis medium in the presence of 50 ng/ml SDF-1. 75 μl of preincubated human PBMC with or without anti-human CD81 antibody were loaded onto the upper wells and incubated for 2 hours in humidified incubators in 5% $CO_2$ at 37° C. After incubation, 50 μl of lower well cell suspension was transferred to 96 well black plate (Corning Inc) and added 50 μl of ATP lite (Perkin Elmer). The number of migrated cells was calculated by measuring luminescence intensity using Envision 2102 multilabelreader (Perkin Elmer).

(4) Analysis of Chemotaxis Assay

Percent Chemotaxis was calculated as the percentage of the number of the migrated human PBMC when the anti-human CD81 antibody was added, to the number of the migrated human PBMC when control IgG4 was added. As a result, both anti-human CD81 antibodies inhibited chemotaxis of human PBMC (Table 3). Since the suppressing effect of 002-A07 and 005-C01 on T cell migration of human PBMC containing primary human T cells was observed, it was confirmed that the anti-CD81 antibodies (002-A07 and 005-C01) can be a therapeutic agent of IBD.

TABLE 3

Suppressive effect of 002-A07 and 005-C01 on chemotaxis of human PBMC

| | human PBMC chemotaxis (%) antibody conc. (μg/ml) | | | |
|---|---|---|---|---|
| | 1 | 0.5 | 0.2 | 0.04 |
| control IgG4 | 100 | 100 | 100 | 100 |
| 002-A07 | 0 | 3 | 17 | 59 |
| 005-C01 | 27 | 58 | 63 | 87 |

Experimental Example 4

Effects of Anti-Human CD81 Antibody on Cytokine Production in and Cell Proliferation of Human PBMC The cytokine production in human PBMC was determined according to Life Sci. 2001 Nov. 21; 70(1):81-96.

(1) Cell Culture and Stimulation

Human PBMC was purchased from KAC. According to the attached information from KAC, 60% of the human PBMC used was T cells (CD3-positive cells). The human PBMC were maintained in RPMI1640 medium (GIBCO) supplemented with 10% fetal calf serum (FCS: Hyclone Laboratories) in humidified incubators in 5% $CO_2$ at 37° C. To 96-well plate (IWAKI) was added the anti-human CD81 antibody (002-A07 or 005-C01) or control IgG4 (Acris Antibodies GmbH) at the concentrations described in Table 4, and the human PBMC ($1\times10^5$ cells/ml) were added to each well (100 µl/well). To the cells were added 1000 ng/well anti CD3 antibody (Clone: OKT3, Bio Legend) and 1000 ng/well anti-CD28 antibody (BD Biosciences) (50 µl/well each) and incubated for 48 hours in humidified incubators in 5% $CO_2$ at 37° C. After incubation, the IL-2 level of supernatants was measured by ELISA assay.

(2) IL-2 ELISA Assay

IL-2 concentration produced from human PBMC to which antibody was added was measured by human IL-2 ELISA kit (R&D system). ELISA assay was conducted according to the manufacture's protocol. Percent IL-2 production was calculated as the percentage of the IL-2 level produced from human PBMC when the anti-human CD81 antibody was added, to the IL-2 level produced from human PBMC when control IgG4 was added. The results are shown in Table 4.

(3) Alamar Blue Assay

Cell proliferation was measured by Alamar blue (BIOSOURCE). This assay was conducted according to the manufacture's protocol. Percent cell proliferation was calculated as the percentage of the cell proliferation of human PBMC when the anti-human CD81 antibody was added, to the cell proliferation of human PBMC when control IgG4 was added. The results are shown in Table 5.

TABLE 4

Effect of 002-A07 and 005-C01 on IL-2 production in human PBMC

| | human PBMC IL-2 production (%) antibody conc. (µg/ml) | | | |
|---|---|---|---|---|
| | 5 | 1 | 0.2 | 0.04 |
| control IgG4 | 100 | 100 | 100 | 100 |
| 002-A07 | 123 | 108 | 110 | 98 |
| 005-C01 | 110 | 100 | 101 | 104 |

TABLE 5

Effect of 002-A07 and 005-C01 on cell proliferation of human PBMC

| | human PBMC cell proliferation (%) antibody conc. (µg/ml) | | | |
|---|---|---|---|---|
| | 5 | 1 | 0.2 | 0.04 |
| control IgG4 | 100 | 100 | 100 | 100 |
| 002-A07 | 107 | 104 | 105 | 105 |
| 005-C01 | 114 | 102 | 103 | 104 |

These results demonstrate that both anti-human CD81 antibodies do not stimulate cytokine production in or cell proliferation of human PBMC. Thus, 002-A07 and 005-C01 do not affect cytokine production or cell proliferation that is an index for T cell activation. Accordingly, it was confirmed that the antibodies have no concern for side effect such as cytokine storm due to cytokine overproduction or immunosuppression due to the suppression of T cell function.

Experimental Example 5

Suppressive Effect of Anti-Human CD81 Antibody on Chemotaxis of PBMC from IBD Patients (1) Cell Preparation IBD patient PBMC (purchased from Tissue solution and the like) are maintained in RPMI1640 medium (GIBCO) supplemented with 10% fetal calf serum (FCS: Hyclone Laboratories) in humidified incubators in 5% $CO_2$ at 37° C. The cells are incubated with or without phytohemagglutinin (PHA), human recombinant IL-2, human TNFα, vasoactive intestinal peptide (VIP), IL-22 and IL-7 for 4 days in humidified incubators in 5% $CO_2$ at 37° C.

(2) Antibody Treatment

The IBD patient's PBMC are suspended in chemotaxis medium (RPMI1640 (GIBCO) containing 0.5% BSA (SIGMA), 50 mM HEPES (GIBCO)). The anti-human CD81 antibody (002-A07 or 005-C01) or control human IgG4 (Acris Antibodies GmbH) is added to the cells at various concentrations. The cells were incubated for 2 hours in humidified incubators in 5% $CO_2$ at 37° C.

(3) Chemotaxis Assay

Chemotaxis is examined using a 96-well chemotaxis chamber (corning coster, 5 µm pore size). The lower wells are filled with 235 µl of chemotaxis medium in the presence of SDF-1. 75 µl of preincubated IBD patient PBMC with or without anti-human CD81 antibody are loaded onto the upper wells and incubated for 2 hours in humidified incubators in 5% $CO_2$ at 37° C. After incubation, 50 µl of lower well cell suspension is transferred to 96 well black plate (Corning Inc) and added 50 µl of ATP lite (Perkin Elmer). The number of the migrated cells is calculated by measuring luminescence intensity using Envision 2102 multilabelreader (Perkin Elmer).

(4) Analysis of Chemotaxis Assay

Percent chemotaxis is calculated as the percentage of the number of the migrated IBD patient PBMC when the anti-human CD81 antibody is added, to the number of the migrated IBD patient PBMC when control IgG4 is added.

Experimental Example 6

Effect of Anti-Human CD81 Antibody on Cytokine Production in IBD Patient PBMC (1) Cell Culture and Stimulation IBD patient's PBMC (purchased from Tissue solution and the like) are maintained in RPMI1640 medium (GIBCO) supplemented with 10% fetal calf serum (FCS: Hyclone Laboratories) in humidified incubators in 5% $CO_2$ at 37° C. To 96-well plate (IWAKI) is added the anti-human CD81 antibody (002-A07 or 005-C01) or control IgG4 (Acris Antibodies GmbH) at various concentrations, and the IBD patient PBMC are added to each well. To the cells are added 1000 ng/well anti CD3 antibody (Clone: OKT3, Bio Legend) and 1000 ng/well anti-CD28 antibody (BD Biosciences) (50 µl/well each) and incubated for 48 hours in humidified incubators in 5% $CO_2$ at 37° C. After incubation, the IL-2 level of supernatants is measured by ELISA assay.

(2) IL-2 ELISA Assay

IL-2 concentration produced from IBD patient's PBMC to which antibody is added is measured by human IL-2 ELISA kit (R&D system). ELISA assay is conducted according to the manufacture's protocol. Percent IL-2 production is calculated as the percentage of the IL-2 level produced from human PBMC when the anti-human CD81 antibody is added, to the IL-2 level produced from human PBMC when control IgG4 is added.

Experimental Example 7

Epitope Mapping of Anti-Human CD81 Antibody Using Human and Chicken CD81 Chimeras To identify the epitopes to which each of the anti-human CD81 antibodies (002-A07 and 005-C01) bind, ELISA assays were performed using human-chicken CD81 chimera constructs listed in Table 6. Each construct was transiently expressed in CHO cells and its cell membrane fraction was solubilized with detergents and immobilized onto a plate. The results are summarized in Table 7.

(1) Expression of Chimera CD81 Proteins

Using human CD81 gene (SEQ ID NO:21) and chicken CD81 gene (SEQ ID NO:23), 10 types of chimera CD81 genes depicted in Table 6 were constructed. Each chimera gene was subcloned into pcDNA-DEST40 vector so as to express as a fusion protein having V5 and 6×His tags at the C-terminal. Each chimera construct was transiently expressed in CHO cells with Trans-IT LT-1 (TAKARA BIO, Code MIR2304) according to the manufacture's protocol, and 48 hours after, the membrane fraction was prepared by following procedure. To the CD81 chimera-expressing CHO cells was added HBS buffer (20 mM Hepes (Invitrogen), 150 mM NaCl (NACALAI TESQUE, INC.)) containing 1% (w/v) n-Octylglucoside (NACALAI TESQUE, INC.), and the cells were incubated for 5 min at 4° C. Then, the cell suspension was centrifuged for 20 min at 10000 g and the supernatant was collected. The protein content in the supernatant was determined with BCA Protein Assay Kit (Thermo Scientific Pierce, code: 23225).

TABLE 6

| human-chicken CD81 chimeras | | |
|---|---|---|
| | human CD81 region | chicken CD81 region |
| hCD81 (SEQ ID NO: 22) | 1-236 | — |
| cCD81 (SEQ ID NO: 24) | — | 1-237 |
| h80c | 1-80 | 81-237 |
| h138c | 1-138 | 139-237 |
| h156c | 1-156 | 158-237 |
| h175c | 1-175 | 177-237 |
| h190c | 1-190 | 192-237 |
| c80h | 81-236 | 1-80 |
| c138h | 139-236 | 1-138 |
| c156h | 157-236 | 1-157 |
| c175h | 176-236 | 1-176 |
| c190h | 191-236 | 1-191 |

Each number shows the position of amino acid residues.

TABLE 7

| Epitope mapping using human-chicken CD81 chimeras | | | | | | | | | | | | | |
|---|---|---|---|---|---|---|---|---|---|---|---|---|---|
| | | CD81 antigen construct | | | | | | | | | | | |
| | | hCD81 | cCD81 | c80h | c138h | c156h | c175h | c190h | h80c | h138c | h156c | h175c | h190c |
| Antibody | 002-A07 | ○ | X | ○ | X | X | X | X | X | X | X | ○ | ○ |
| | 005-C01 | ○ | X | ○ | X | X | X | X | X | X | X | ○ | ○ |

○: Absorbance at 450 nm is 100-10% of that in the case CD81 is hCD81
X: Absorbance at 450 nm is less than 10% of that in the case CD81 is hCD81

(2) ELISA Assay

As control antibodies, human IgG4 antibody (Acris Antibodies GmbH) and mouse IgG antibody were used. Human-chicken chimera protein was captured via His tag introduced into the C-terminal by adding the membrane fraction (5 μg/100 μL/well) prepared (1) above to Ni NTA His Sorb plate (QIAGEN) in the presence of 1% (w/v) n-Octylglucoside and incubating for 3 hours at 4° C. After washing with TEST (TBS, 0.05% (v/v) Tween 20) three times, an anti-human CD81 antibody or a control antibody (50 μL/well) was added and incubated for 1 hour at room temperature (RT). After washing, 2000 fold-diluted HRP-labeled anti-human IgG4 antibody (Mouse anti-human $IgG_4$ HRP clone: HP6023 Beckman Coulter) or 1000 fold-diluted HRP-labeled anti-mouse IgG antibody (Invitrogen) (50 μL/well) were added. The plate was incubated for 1 hour at RT and washed with TBST three times. And then, peroxidase activity was determined by TMB One solution (Promega; Code 53025). The reaction was stopped with 2 M $H_2SO_4$ (50 μL) and absorbance at 450 nm was measured.

(3) Interpretation of Results

Human CD81 have two extracellular domains. 002-A07 and 005-C01 bound to hCD81, c80h, h175c and h190c, but did not bind to cCD81, c138h, c156h, c175h, c190h, h80c, h138c and h156c. These results indicate that the epitopes recognized by 002-A07 and 005-C01 antibodies binding to human CD81 are present between the 80th amino acid residue and 175th amino acid residue of human CD81 polypeptide.

Experimental Example 8

Epitope Mapping of Anti-Human CD81 Antibody Using Alanine-Scanning

As shown in Experimental Example 7, the epitope region of human CD81 for 002-A07 and 005-C01 antibodies was determined. In this Example, in order to assess the contribution of individual amino acid residues in the epitope region to binding with the anti-human CD81 antibodies and identify detailed epitope residues, alanine-scanning mutagenesis (Cunningham & Wells, Science 244: 1081-1085 (1989)) was carried out in the sequence of the epitope region determined in Experimental Example 7. Human CD81 mutants were prepared by site-directed mutagenesis (this work was outsourced to TAKARA BIO) and subcloned into pcDNA-DEST40 vector. Subsequently, these mutants were expressed in CHO cells and the binding of 002-A07 and 005-C01 antibodies with individual mutants was assayed in the same manner as in Experimental Example 7. Relative binding affinity was calculated as the percentage of binding affinity of 002-A07 or 005-C01 antibody with each mutant to binding affinity of 002-A07 or 005-C01 antibody with wild type human CD81, and the mutants were classified into 3 groups based on the relative binding affinity. The expression levels of the individual mutants were corrected by the expression levels of V5 tag which was inserted into the C-terminal of the mutants. The results are summarized in Table 8.

As shown in Experimental Example 7, the anti-human CD81 antibodies 002-A07 and 005-C01 recognize the same epitope region that is located between the 80th and 175th amino acid residues of human CD81. The results of alanine scanning indicate that human CD81 has 13 amino acid residues (V135, D137, A143, H151, G158, T163, A164, L165, S168, V169, L170, N172 and L174) critical for binding with 002-A07 and 17 amino acid residues (Y127, A130, L131, V135, V136, D137, N142, A143, L154, 6158, T163, L165, S168, V169, L170, K171 and L174) critical for binding with 005-C01 within the epitope region, respectively.

TABLE 8

Epitope mapping of anti-human CD81 antibodies by alanine scanning

| Amino acid residue No. | Wild type (codon) | Substitutions (codon) | 002-A07 | 005-C01 |
|---|---|---|---|---|
| 127 | Y (TAT) | F (TTC) | ○ | Δ |
| 130 | A (GCC) | T (ACC) | ○ | Δ |
| 131 | L (CTA) | A (GCC) | ○ | X |
| 135 | V (GTC) | A (GCC) | X | X |
| 136 | V (GTC) | A (GCC) | ○ | Δ |
| 137 | D (GAT) | A (GCC) | X | X |
| 142 | N (AAC) | A (GCC) | ○ | Δ |
| 143 | A (GCC) | T (ACC) | Δ | X |
| 151 | H (CAC) | A (GCC) | Δ | ○ |
| 154 | L (CTT) | A (GCC) | ○ | X |
| 158 | G (GGC) | S (AGC) | X | X |
| 163 | T (ACT) | A (GCC) | Δ | Δ |
| 164 | A (GCT) | T (ACC) | X | ○ |
| 165 | L (TTG) | A (GCC) | X | X |
| 168 | S (TCA) | A (GCC) | Δ | X |
| 169 | V (GTG) | A (GCC) | X | X |
| 170 | L (CTC) | A (GCC) | Δ | X |
| 171 | K (AAG) | A (GCC) | ○ | Δ |
| 172 | N (AAC) | A (GCC) | Δ | ○ |
| 174 | L (TTG) | A (GCC) | Δ | X |

Each symbol shows;
○: relative binding affinity is equal or slightly weak compared to wild type human CD81 (relative binding affinity is ranged 40-100%).
Δ: relative binding affinity is significantly weak compared to wild type human CD81 (relative binding affinity is ranged 20-40%).
X: relative binding affinity is quite weak compared to wild type human CD81 (relative binding affinity is ranged under 20%).
(Since the 81st to 112nd amino acid residues are transmembrane or intracellular domains, alanine mutants were not prepared.)

Experimental Example 9

Epitope Mapping of the Anti-Human CD81 Antibody Using Homolog-Scanning

Since alanine-scanning may cause unwanted conformational change and physicochemical disruptions (Cunningham and Wells, Science 244: 1081-1085 (1989)), we conducted homolog-scanning which is other type of systematic scanning to further increase the resolution of energetic profiling of functional epitopes. The homolog-scanning mutagenesis is designed to minimize the possibility of structural disruption upon side chain substitution by introducing a substitutional group so as to maintain the structure and function of protein (Protein Science (2005), 14:2405-2413).

As shown in Experimental Example 8, human CD81 has 13 and 17 amino acid residues critical for binding with 002-A07 and 005-C01, respectively, within the epitope region. Homolog mutants were prepared in these residues according to the rule described by Protein Science (2005), 14:2405-2413). These homolog mutants were expressed in CHO cells and the binding of the anti-human CD81 antibodies with the individual mutants was assayed in the same manner as Experimental Example 8.

The results are summarized in Table 9. The homolog-scanning revealed that human CD81 has 9 amino acid residues critical for binding with 002-A07 and 9 amino acid residues critical for binding with 005-C01, respectively, within the epitope region. The 151st, 164th, 168th and 172nd residues are specifically critical for binding with 002-A07. On the other hand, the 127th, 130th, 143rd and 154th residues are specifically critical for binding with 005-C01.

TABLE 9

Epitope mapping of anti-human CD81 antibodies by homolog-scanning

| Amino acid residue No. | Wild type (codon) | Substitutions (codon) | Homo | Ala |
|---|---|---|---|---|
| 002-A07 | | | | |
| 135 | V (GTC) | L (CTG) | X | X |
| 137 | D (GAT) | E (GAG) | X | X |
| 143 | A (GCC) | V (GTG) | ○ | Δ |
| 151 | H (CAC) | R (CGC) | Δ | Δ |
| 158 | G (GGC) | A (GCC) | X | X |
| 163 | T (ACT) | S (TCT) | ○ | Δ |
| 164 | A (GCT) | V (GTG) | X | X |
| 165 | L (TTG) | I (ATC) | ○ | X |
| 168 | S (TCA) | T (ACA) | X | Δ |
| 169 | V (GTG) | L (CTG) | X | X |
| 170 | L (CTC) | I (ATC) | Δ | Δ |
| 172 | N (AAC) | Q (CAG) | Δ | Δ |
| 174 | L (TTG) | I (ATC) | ○ | Δ |
| 005-C01 | | | | |
| 127 | Y (TAT) | W (TGG) | X | Δ |
| 130 | A (GCC) | V (GTG) | X | Δ |
| 131 | L (CTA) | I (ATC) | ○ | X |
| 135 | V (GTC) | L (CTG) | X | X |
| 136 | V (GTC) | L (CTG) | ○ | Δ |
| 137 | D (GAT) | E (GAG) | X | X |
| 142 | N (AAC) | Q (CAG) | ○ | Δ |
| 143 | A (GCC) | V (GTG) | Δ | X |
| 154 | L (CTT) | I (ATC) | Δ | X |
| 158 | G (GGC) | A (GCC) | X | X |
| 163 | T (ACT) | S (TCT) | ○ | Δ |
| 165 | L (TTG) | I (ATC) | ○ | X |
| 168 | S (TCA) | T (ACA) | ○ | X |
| 169 | V (GTG) | L (CTG) | X | X |
| 170 | L (CTC) | I (ATC) | Δ | X |
| 171 | K (AAG) | R (AGG) | ○ | Δ |
| 174 | L (TTG) | I (ATC) | ○ | X |

Each symbol shows;
○: relative binding affinity is equal or slightly weak compared to wild type human CD81 (relative binding affinity is ranged 40-100%).
Δ: relative binding affinity is significantly weak compared to wild type human CD81 (relative binding affinity is ranged 20-40%).
X: relative binding affinity is quite weak compared to wild type human CD81 (relative binding affinity is ranged under 20%).
Homo: homolog mutants; Ala: alanine mutants

Example 2

Generating 002-A07 Mutant Antibodies

Construction of Glycosylation Site Mutants

The VL region from n-CoDeR (Registered Trade Mark) clone 002-A07 was modified to eliminate the potential N-glycosylation site (amino acid sequence: NLS) located in CDR3. Six VL variants were designed and purchased from Geneart AG (Regensburg Germany): N113S, N113G, N113Q, S115A, S115G and S115N. These were inserted into an expression vector containing the λ constant region as described in Example 1. The six variant light chains were transfected, together with the 002-A07 γ4 S228P heavy chain, into HEK293-EBNA cells. Antibodies were expressed and purified as described in Example 1.

Isolation of Clones from Affinity Maturation

Library Construction

A mutagenized library was created for n-CoDeR (Registered Trade Mark) clone 002-A07. Plasmid DNA was used as template in an error-prone PCR protocol (Saviranta at al. 1998) where the mutations are introduced randomly over the entire antibody variable regions. The resulting fragments were ligated into a phagemid vector and electroporated into *E. coli* HB101F' (constructed by conjugation of the F' plasmid into strain HB101 (Invitrogen)) for the construction of a Fab library. The library was stored as bacterial glycerol stocks at −80° C. (Saviranta P, Pajunen M, Jauria P, Karp M, Pettersson K, MäntsäläP and Lövgren T (1998). "Engineering the steroid-specificity of an anti-17β-estradiol Fab by random mutagenesis and competitive phage panning". Prot Eng 11(2) 143-152.)

Phage Display Panning and Screening of Individual Soluble Fab

Phages with Fab display were expressed from the *E. coli* library using helper phage R408 (Stratagene) and purified from the culture supernatant using PEG precipitation.

CD81-specific clones with improved affinity were isolated by phage display technology. Two parallel panning strategies (A and B), each consisting of two consecutive pannings, were used to isolate clones with improved affinity. In strategy A purified recombinant human CD81 protein coated on polystyrene beads was used as target. In strategy B Jurkat cells with endogenous expression of human CD81 were used as target. Unbound phages were removed by washing. Target binding Fab-phages were eluted using trypsin and amplified in *E. coli* HB101F'.

Phagemid DNA was isolated from the amplified pool of clones after panning 2. Gene III was excised by restriction enzyme digestion followed by re-ligation resulting in a Fab expressing plasmid pool. Plasmids were transformed into *E. coli TOP*10 (Invitrogen) and transformants expressing individual soluble Fab selected on antibiotic-containing agar plates. Individual bacterial colonies were transferred from agar plates to microtiter plates for expression of soluble Fab with C-terminal His-tag.

Primary screening was performed using an ELISA set-up with sequential addition of the following reagents: 1) coating of monoclonal anti-His antibody; 2) His-tagged Fab from affinity maturation; 3) FLAG-tagged recombinant human CD81 protein; 4) AP-conjugated anti-FLAG antibody; 5) Luminescence substrate. Clones with the highest activity in the primary screening were cherry picked to new microtiter plates and re-expressed. A secondary screening was performed with the same ELISA set-up as described for the primary screening. Clones with improved binding compared to the parent clone 002-A07 in Fab format were analyzed by DNA sequencing. Unique Fab clones were purified from *E. coli* periplasm using Ni-NTA chromatography. Affinity ranking of purified Fab clones was performed using flow cytometry with Jurkat cells and Biacore with immobilized recombinant human CD81 protein.

Production of IgG4-S228P

Clones with improved affinity compared to the parent clone were converted to IgG4-5228P format, expressed and purified as described in Example 1.

The sequences of the 002-A07 mutant antibodies obtained, determined by DNA sequencing, are shown in the sequence listing according to the correspondence in the table 10 below.

TABLE 10

| SEQ ID NOs representing peptide or DNA sequences of antibodies | | | | | | | | | | | | | |
|---|---|---|---|---|---|---|---|---|---|---|---|---|---|
| group | 1 | | 2 | 3 | 4 | 5 | 6 | 7 | 8 | 9 | 10 | 11 | 12 |
| group | 25 | | 26 | 27 | 28 | 29 | 30 | 31 | 32 | 33 | 34 | 35 | 36 |
| Antibody | 002-A07 | 005-C01 | 002-A07 N113G | 002-A07 N113Q | 002-A07 N113S | 002-A07 S115A | 002-A07 S115G | 002-A07 S115N | 001-B06 | 002-B05 | 002-B07 | 002-C02 | 002-C09 |
| L1CDR peptide | 1 | 11 | 1 | 1 | 1 | 1 | 1 | 1 | 1 | 60 | 1 | 1 | 60 |
| L2CDR peptide | 2 | 12 | 2 | 2 | 2 | 2 | 2 | 2 | 2 | 2 | 2 | 2 | 2 |
| L3CDR peptide | 3 | 13 | 37 | 40 | 43 | 46 | 49 | 52 | 43 | 3 | 66 | 3 | 66 |
| H1CDR peptide | 4 | 14 | 4 | 4 | 4 | 4 | 4 | 4 | 4 | 4 | 4 | 4 | 4 |
| H2CDR peptide | 5 | 15 | 5 | 5 | 5 | 5 | 5 | 5 | 5 | 5 | 5 | 69 | 5 |
| H3CDR peptide | 6 | 16 | 6 | 6 | 6 | 6 | 6 | 6 | 55 | 61 | 6 | 70 | 6 |
| group | 49 | | 50 | 51 | 52 | 53 | 54 | 55 | 56 | 57 | 58 | 59 | 60 |
| L-chain variable region | 7 | 17 | 125 | 126 | 127 | 128 | 129 | 130 | 131 | 133 | 135 | 137 | 139 |
| L-chain variable region peptide | 8 | 18 | 38 | 41 | 44 | 47 | 50 | 53 | 56 | 62 | 67 | 71 | 75 |
| H-chain variable region | 9 | 19 | 9 | 9 | 9 | 9 | 9 | 9 | 132 | 134 | 136 | 138 | 136 |
| H-chain variable region peptide | 10 | 20 | 10 | 10 | 10 | 10 | 10 | 10 | 57 | 63 | 10 | 72 | 10 |

TABLE 10-continued

SEQ ID NOs representing peptide or DNA sequences of antibodies

| group | 73 | | 74 | 75 | 76 | 77 | 78 | 79 | 80 | 81 | 82 | 83 | 84 |
|---|---|---|---|---|---|---|---|---|---|---|---|---|---|
| L-chain DNA | 25 | 29 | | | | | | | | | | | |
| L-chain peptide | 26 | 30 | 39 | 42 | 45 | 48 | 51 | 54 | 58 | 64 | 68 | 73 | 76 |
| H-chain DNA | 27 | 31 | | | | | | | | | | | |
| H-chain peptide | 28 | 32 | 28 | 28 | 28 | 28 | 28 | 28 | 59 | 65 | 28 | 74 | 28 |
| scFv DNA | 33 | 35 | | | | | | | | | | | |
| scFv peptide | 34 | 36 | | | | | | | | | | | |

| group | 13 | 14 | 15 | 16 | 17 | 18 | 19 | 20 | 21 | 22 | 23 | 24 |
|---|---|---|---|---|---|---|---|---|---|---|---|---|
| group | 37 | 38 | 39 | 40 | 41 | 42 | 43 | 44 | 45 | 46 | 47 | 48 |
| Antibody | 002-D03 | 002-D08 | 002-D10 | 002-F01 | 002-F05 | 002-F07 | 002-H02 | 002-H03 | 003-A10 | 003-A11 | 003-D07 | 003-F08 |
| L1CDR peptide | 1 | 80 | 1 | 1 | 1 | 98 | 60 | 1 | 1 | 1 | 1 | 1 |
| L2CDR peptide | 2 | 2 | 2 | 2 | 2 | 2 | 2 | 2 | 2 | 2 | 2 | 2 |
| L3CDR peptide | 3 | 3 | 66 | 90 | 52 | 3 | 3 | 90 | 3 | 66 | 3 | 90 |
| H1CDR peptide | 77 | 4 | 4 | 4 | 4 | 4 | 4 | 4 | 4 | 110 | 4 | 4 |
| H2CDR peptide | 5 | 81 | 5 | 5 | 5 | 5 | 5 | 5 | 5 | 5 | 5 | 120 |
| H3CDR peptide | 6 | 6 | 6 | 6 | 93 | 99 | 99 | 6 | 55 | 6 | 115 | 6 |

| group | 61 | 62 | 63 | 64 | 65 | 66 | 67 | 68 | 69 | 70 | 71 | 72 |
|---|---|---|---|---|---|---|---|---|---|---|---|---|
| L-chain variable region | 7 | 141 | 143 | 145 | 146 | 148 | 150 | 151 | 153 | 155 | 157 | 159 |
| L-chain variable region peptide | 8 | 82 | 86 | 91 | 94 | 100 | 104 | 106 | 108 | 111 | 116 | 121 |
| H-chain variable region | 140 | 142 | 144 | 136 | 147 | 149 | 149 | 152 | 154 | 156 | 158 | 160 |
| H-chain variable region peptide | 78 | 83 | 87 | 10 | 95 | 101 | 101 | 10 | 57 | 112 | 117 | 122 |

| group | 85 | 86 | 87 | 88 | 89 | 90 | 91 | 92 | 93 | 94 | 95 | 96 |
|---|---|---|---|---|---|---|---|---|---|---|---|---|
| L-chain DNA | | | | | | | | | | | | |
| L-chain peptide | 26 | 84 | 88 | 92 | 96 | 102 | 105 | 107 | 109 | 113 | 118 | 123 |
| H-chain DNA | | | | | | | | | | | | |
| H-chain peptide | 79 | 85 | 89 | 28 | 97 | 103 | 103 | 28 | 59 | 114 | 119 | 124 |
| scFv DNA | | | | | | | | | | | | |
| scFv peptide | | | | | | | | | | | | |

Experimental Example 10

Suppressive Effects of 002-A07 Mutant Antibodies on Chemotaxis of Jurkat Cells This experiment was performed in the same manner as Experimental Example 2. As a result, all 002-A07 mutant antibodies exhibited suppressive effects on chemotaxis of Jurkat cells (a human T cell line) (Table 11).

TABLE 11

Suppressive effects of 002-A07 mutant antibodies on chemotaxis of Jurkat cells

| antibody | 10 μg/mL | 1 μg/mL | 0.1 μg/mL | 0.01 μg/mL | 0.001 μg/mL |
|---|---|---|---|---|---|
| control IgG4 | 100 | 100 | 100 | 100 | 100 |
| 002-A07 | 3 | −2 | 21 | 93 | 90 |
| 001-B06 | 3 | 3 | 35 | 91 | 102 |

TABLE 11-continued

Suppressive effects of 002-A07 mutant antibodies on chemotaxis of Jurkat cells

| antibody | 10 μg/mL | 1 μg/mL | 0.1 μg/mL | 0.01 μg/mL | 0.001 μg/mL |
|---|---|---|---|---|---|
| 002-B05 | −10 | −1 | 10 | 78 | 84 |
| 002-B07 | −9 | 4 | 8 | 87 | 92 |
| 002-C02 | −4 | −5 | 31 | 104 | 106 |
| 002-C09 | 11 | −1 | 15 | 82 | 101 |
| 002-D03 | 16 | 14 | 25 | 91 | 105 |
| 002-D08 | 14 | 19 | 67 | 105 | 101 |
| 002-D10 | 10 | 6 | 34 | 87 | 97 |
| 002-F01 | 9 | 4 | 35 | 87 | 89 |
| 002-F05 | 7 | 5 | 27 | 79 | 102 |
| 002-F07 | 15 | 13 | 38 | 88 | 101 |
| 002-H02 | −2 | −10 | −1 | 85 | 87 |
| 002-H03 | −3 | 0 | 13 | 89 | 106 |
| 003-A10 | 3 | 3 | 15 | 93 | 104 |
| 003-A11 | 2 | 1 | 16 | 86 | 91 |
| 003-D07 | −9 | −5 | 42 | 79 | 87 |
| 003-F08 | −4 | −3 | 21 | 79 | 80 |
| 002-A07 N113G | 7 | 13 | 38 | 101 | 99 |
| 002-A07 N113Q | 12 | 13 | 37 | 99 | 104 |
| 002-A07 N113S | 12 | 13 | 40 | 101 | 99 |
| 002-A07 S115A | −9 | −4 | 32 | 78 | 82 |
| 002-A07 S115G | −3 | −9 | 13 | 74 | 84 |
| 002-A07 S115N | −9 | −11 | −4 | 69 | 79 |

Experimental Example 11

Effects of 002-A07 Mutant Antibodies on Cytokine Production by And Cell Proliferation of Human PBMC This experiment was performed in the same manner as Experimental Example 4. 5A6, a commercially available mouse anti-human CD81 antibody (Santa Cruz Co.) that enhances IL-2 production while suppressing T cell migration, was used for control. As a result, none of the 002-A07 mutant antibodies enhanced IL-2 production by human PBMCs (Table 12), nor did they have any noticeable effect on the cell proliferation (Table 13).

TABLE 12

Effects of 002-A07 mutant antibodies on IL-2 production by human PBMC

| antibody | 10 μg/mL | 1 μg/mL |
|---|---|---|
| mouse IgG | 100 | 100 |
| 5A6 | 320 | 179 |
| human IgG4 | 100 | 100 |
| 002-A07 | 109 | 111 |
| 001-B06 | 174 | 130 |
| 002-B05 | 59 | 109 |
| 002-B07 | 67 | 100 |
| 002-C02 | 57 | 90 |
| 002-C09 | 77 | 95 |
| 002-D03 | 49 | 127 |
| 002-D08 | 101 | 140 |
| 002-D10 | 96 | 169 |
| 002-F01 | 101 | 188 |
| 002-F05 | 92 | 187 |
| 002-F07 | 78 | 224 |
| 002-H02 | 61 | 156 |
| 002-H03 | 82 | 124 |
| 003-A10 | 109 | 114 |
| 003-A11 | 84 | 128 |
| 003-D07 | 78 | 89 |

TABLE 12-continued

Effects of 002-A07 mutant antibodies on IL-2 production by human PBMC

| antibody | 10 μg/mL | 1 μg/mL |
|---|---|---|
| 003-F08 | 98 | 108 |
| 002-A07 N113G | 117 | 114 |
| 002-A07 N113Q | 101 | 92 |
| 002-A07 N113S | 80 | 92 |
| 002-A07 S115A | 76 | 96 |
| 002-A07 S115G | 115 | 91 |
| 002-A07 S115N | 120 | 118 |

TABLE 13

Effects of 002-A07 mutant antibodies on cell proliferation of human PBMC

| antibody | 10 μg/mL | 1 μg/mL |
|---|---|---|
| mouse IgG | 100 | 100 |
| 5A6 | 91 | 95 |
| human IgG4 | 100 | 100 |
| 002-A07 | 102 | 101 |
| 001-B06 | 125 | 102 |
| 002-B05 | 121 | 103 |
| 002-B07 | 111 | 106 |
| 002-C02 | 113 | 109 |
| 002-C09 | 136 | 105 |
| 002-D03 | 114 | 107 |
| 002-D08 | 107 | 97 |
| 002-D10 | 112 | 97 |
| 002-F01 | 109 | 100 |
| 002-F05 | 106 | 103 |
| 002-F07 | 108 | 97 |
| 002-H02 | 105 | 96 |
| 002-H03 | 118 | 103 |
| 003-A10 | 112 | 110 |
| 003-A11 | 118 | 110 |
| 003-D07 | 121 | 97 |
| 003-F08 | 120 | 110 |
| 002-A07 N113G | 117 | 103 |
| 002-A07 N113Q | 123 | 103 |
| 002-A07 N113S | 119 | 108 |
| 002-A07 S115A | 126 | 108 |
| 002-A07 S115G | 145 | 97 |
| 002-A07 S115N | 121 | 87 |

Experimental Example 12

Epitope Mapping of 002-A07 Mutant Antibodies Using Alanine Scanning

This experiment was performed in the same manner as Experimental Example 8. Since the 1st to 43rd, 63rd to 112th, 202nd and subsequent residues are transmembrane or intracellular domains [Levy, S. et al., Annu. Rev. Immunol. (1998) 16, 89-109], no alanine mutant was generated. Since the 156th, 157th, 175th, and 190th residues are cysteine residues, no alanine mutant was generated. The relative binding affinity for alanine mutants not listed in Table 14 was equal or slightly weak in all 002-A07 mutant antibodies compared to wild type human CD81 (relative binding affinity is ranged 40-100).

TABLE 14

Epitope mapping of 002-A07 mutant antibodies by alanine scanning

| substitution | Y127F | V135A | D137A | A143T | H151A | G158S | T163A | A164T | L165A |
|---|---|---|---|---|---|---|---|---|---|
| 002-A07 | ○ | X | X | Δ | X | X | X | X | X |
| 002-A07 N113G | ○ | X | X | ○ | X | X | X | X | X |
| 002-A07 N113Q | ○ | X | X | ○ | X | X | X | X | X |
| 002-A07 N113S | ○ | X | X | ○ | X | X | X | X | X |
| 002-A07 S115A | Δ | X | X | Δ | X | X | X | X | X |
| 002-A07 S115G | ○ | X | X | ○ | Δ | X | X | X | X |
| 002-A07 S115N | ○ | X | Δ | ○ | ○ | Δ | ○ | X | X |
| 001-B06 | ○ | Δ | ○ | ○ | ○ | ○ | ○ | Δ | Δ |
| 002-B05 | ○ | X | X | ○ | Δ | X | Δ | X | X |
| 002-B07 | ○ | X | Δ | ○ | ○ | Δ | ○ | X | X |
| 002-C02 | ○ | X | X | ○ | ○ | Δ | ○ | X | X |
| 002-C09 | ○ | X | Δ | ○ | ○ | Δ | ○ | X | X |
| 002-D03 | ○ | X | X | ○ | ○ | Δ | ○ | X | X |
| 002-D08 | ○ | X | Δ | ○ | ○ | Δ | ○ | X | X |
| 002-D10 | ○ | X | ○ | ○ | ○ | ○ | ○ | X | X |
| 002-F01 | ○ | X | Δ | ○ | ○ | Δ | ○ | X | X |
| 002-F05 | ○ | X | Δ | ○ | ○ | Δ | ○ | X | X |
| 002-F07 | ○ | X | Δ | ○ | ○ | Δ | ○ | X | X |
| 002-H02 | ○ | X | Δ | ○ | ○ | ○ | ○ | X | X |
| 002-H03 | ○ | X | ○ | ○ | ○ | ○ | ○ | X | X |
| 003-A10 | ○ | Δ | ○ | ○ | ○ | ○ | ○ | Δ | Δ |
| 003-A11 | ○ | X | Δ | ○ | ○ | Δ | ○ | X | X |
| 003-D07 | ○ | X | X | ○ | Δ | X | Δ | X | X |
| 003-F08 | ○ | X | X | ○ | Δ | X | Δ | X | X |

| substitution | S168A | V169A | L170A | K171A | N172A | L174A | I194A |
|---|---|---|---|---|---|---|---|
| 002-A07 | Δ | X | Δ | Δ | Δ | Δ | X |
| 002-A07 N113G | Δ | X | X | ○ | ○ | ○ | X |
| 002-A07 N113Q | Δ | X | Δ | ○ | ○ | ○ | X |
| 002-A07 N113S | Δ | X | X | ○ | ○ | ○ | X |
| 002-A07 S115A | Δ | X | X | ○ | ○ | ○ | X |
| 002-A07 S115G | Δ | X | Δ | ○ | Δ | ○ | X |
| 002-A07 S115N | Δ | X | ○ | ○ | ○ | ○ | Δ |
| 001-B06 | ○ | X | ○ | ○ | ○ | ○ | Δ |
| 002-B05 | ○ | X | Δ | ○ | ○ | ○ | Δ |
| 002-B07 | ○ | X | ○ | ○ | ○ | ○ | Δ |
| 002-C02 | ○ | X | ○ | ○ | ○ | ○ | Δ |
| 002-C09 | ○ | X | ○ | ○ | ○ | ○ | Δ |
| 002-D03 | ○ | X | ○ | ○ | ○ | ○ | Δ |
| 002-D08 | ○ | X | Δ | ○ | ○ | ○ | ○ |
| 002-D10 | ○ | X | ○ | ○ | ○ | ○ | Δ |
| 002-F01 | Δ | X | Δ | ○ | ○ | ○ | X |
| 002-F05 | X | X | ○ | ○ | ○ | ○ | X |
| 002-F07 | ○ | X | ○ | ○ | Δ | Δ | X |
| 002-H02 | ○ | X | ○ | ○ | ○ | ○ | Δ |
| 002-H03 | ○ | X | ○ | ○ | ○ | ○ | Δ |
| 003-A10 | ○ | X | ○ | Δ | X | Δ | Δ |
| 003-A11 | ○ | X | ○ | ○ | Δ | Δ | X |
| 003-D07 | ○ | X | Δ | ○ | X | Δ | X |
| 003-F08 | ○ | X | Δ | ○ | Δ | Δ | Δ |

Each symbol shows;

○: relative binding affinity is equal or slightly weak compared to wild type human CD81 (relative binding affinity is ranged 40-100%).

Δ: relative binding affinity is significantly weak compared to wild type human CD81 (relative binding affinity is ranged 20-40%).

X: relative binding affinity is quite weak compared to wild type human CD81 (relative binding affinity is ranged under 20%).

Experimental Example 13

Epitope Mapping of 002-A07 Mutant Antibodies Using Homolog-Scanning

Amino acid residues thought to be important to the binding of 002-A07 mutant antibodies, judging from the results of alanine scanning, were subjected to homolog-scanning in the same manner as Experimental Example 9. As a result, the amino acid residues important to the binding shown below were identified respectively for the 002-A07 mutant antibodies. It was found that all 002-A07 mutant antibodies bind to the same epitope as with 002-A07.

002-A07 N113G: V135, D137, H151, G158, A164, S168, V169, L170

002-A07 N113Q: V135, D137, H151, G158, A164, S168, V169, L170

002-A07 N113S: V135, D137, H151, G158, A164, S168, V169, L170

002-A07 S115A Y127, V135, D137, A143, H151, G158, A164, S168, V169, L170

002-A07 S115G: V135, D137, H151, G158, A164, S168, V169, L170, N172

002-A07 S115N: V135, D137, A164, S168, V169

001-B06: A164, V169

002-B05: V135, D137, H151, 6158, A164, V169, L170

002-B07: V135, A164, V169

002-002: V135, D137, A164, V169

002-009: A164, V169

002-003: V135, D137, A164, V169

002-D08: A164, V169

002-D10: A164, V169

002-F01: V135, D137, G158, A164, S168, V169

002-F05: V135, D137, A164, S168, V169

002-F07: V135, D137, A164, V169

002-H02: A164, V169

002-H03: A164, V169

003-A10: A164, V169

003-A11: A164, V169

003-D07: V135, D137, H151, G158, A164, V169

003-F08: V135, D137, H151, G158, A164, V169, L170

TABLE 15

Epitope mapping of 002-A07 mutant antibodies by homolog-scanning

| substitution | Y127W | V135L | D137E | A143V | H151R | G158A | T163S | A164V | L165I |
|---|---|---|---|---|---|---|---|---|---|
| 002-A07 | — | X | X | ○ | X | X | ○ | X | ○ |
| 002-A07 N113G | — | X | X | — | X | X | ○ | X | ○ |
| 002-A07 N113Q | — | X | X | — | X | X | ○ | X | ○ |
| 002-A07 N113S | — | X | X | — | X | X | ○ | X | ○ |
| 002-A07 S115A | X | X | X | Δ | X | X | ○ | X | ○ |
| 002-A07 S115G | — | X | X | — | X | X | ○ | X | ○ |
| 002-A07 S115N | — | Δ | Δ | — | — | ○ | — | X | ○ |
| 001-B06 | — | ○ | — | — | — | — | — | Δ | ○ |
| 002-B05 | — | X | Δ | — | X | Δ | ○ | X | ○ |
| 002-B07 | — | Δ | ○ | — | — | ○ | — | X | ○ |
| 002-C02 | — | Δ | X | — | — | ○ | — | X | ○ |
| 002-C09 | — | ○ | ○ | — | — | ○ | — | X | ○ |
| 002-D03 | — | Δ | Δ | — | — | ○ | — | X | ○ |
| 002-D08 | — | ○ | ○ | — | — | ○ | — | X | ○ |
| 002-D10 | — | ○ | — | — | — | — | — | X | ○ |
| 002-F01 | — | Δ | Δ | — | — | Δ | — | X | ○ |
| 002-F05 | — | Δ | Δ | — | — | ○ | — | X | ○ |
| 002-F07 | — | Δ | Δ | — | — | ○ | — | X | ○ |
| 002-H02 | — | ○ | ○ | — | — | — | — | X | ○ |
| 002-H03 | — | ○ | — | — | — | — | — | X | ○ |
| 003-A10 | — | ○ | — | — | — | — | — | Δ | ○ |
| 003-A11 | — | ○ | ○ | — | — | ○ | — | X | ○ |
| 003-D07 | — | X | Δ | — | X | Δ | ○ | X | ○ |
| 003-F08 | — | X | X | — | X | Δ | ○ | X | ○ |

| substitution | S168T | V169L | L170I | K171R | N172Q | L174I | I194L |
|---|---|---|---|---|---|---|---|
| 002-A07 | X | X | Δ | ○ | Δ | ○ | ○ |
| 002-A07 N113G | X | X | Δ | — | — | — | ○ |
| 002-A07 N113Q | X | X | Δ | — | — | — | ○ |
| 002-A07 H113S | X | X | Δ | — | — | — | ○ |
| 002-A07 S115A | X | X | Δ | — | — | — | ○ |
| 002-A07 S115G | X | X | Δ | — | Δ | — | ○ |
| 002-A07 S115N | X | X | — | — | — | — | ○ |
| 001-B06 | — | Δ | — | — | — | — | ○ |
| 002-B05 | — | X | Δ | — | — | — | ○ |
| 002-B07 | — | X | — | — | — | — | ○ |

TABLE 15-continued

| Epitope mapping of 002-A07 mutant antibodies by homolog-scanning | | | | | | | |
|---|---|---|---|---|---|---|---|
| 002-C02 | — | X | — | — | — | — | ○ |
| 002-C09 | — | X | — | — | — | — | ○ |
| 002-D03 | — | X | — | — | — | — | ○ |
| 002-D08 | — | Δ | ○ | — | — | — | — |
| 002-D10 | — | X | — | — | — | — | ○ |
| 002-F01 | X | X | ○ | — | — | — | ○ |
| 002-F05 | X | X | — | — | — | — | ○ |
| 002-F07 | — | X | — | — | ○ | ○ | ○ |
| 002-H02 | — | X | — | — | — | — | ○ |
| 002-H03 | — | Δ | — | — | — | — | ○ |
| 003-A10 | — | Δ | — | ○ | ○ | ○ | ○ |
| 003-A11 | — | X | — | — | ○ | ○ | ○ |
| 003-D07 | — | X | ○ | — | ○ | ○ | ○ |
| 003-F08 | — | X | Δ | — | ○ | ○ | ○ |

Each symbol shows;
○: relative binding affinity is equal or slightly weak compared to wild type human CD81 (relative binding affinity is ranged 40-100%).
Δ: relative binding affinity is significantly weak compared to wild type human CD81 (relative binding affinity is ranged 20-40%).
X: relative binding affinity is quite weak compared to wild type human CD81 (relative binding affinity is ranged under 20%).
—: Not tested (since the mutant was judged to be unimportant to the binding based on the results of alanine scanning).

Example 3

Generating Human IgG1-Type Anti-CD81 Antibody

An EcoRI site and an XhoI site were added to each ends of the DNA fragment encodes L-chain peptide sequence of 002-A07 having a human IL-2 signal sequence added to the N-terminal portion thereof, and the fragment was inserted into the EcoRI-XhoI site of pcDNA3.1(+) (Invitrogen Co.) (a). Likewise, an EcoRI site and an XhoI site were added to each ends of the DNA fragment encodes H-chain peptide sequence of 002-A07 having a human IL-2 signal sequence added to the N-terminal portion thereof, and the fragment was inserted into the EcoRI-XhoI Site of pcDNA3.1(+). Furthermore, the DNA fragment was amplified by PCR with the above-described plasmid incorporating the H-chain gene as the template, using the DNA primers shown below.

5' side DNA primer (a sequence containing EcoRI site portion): 5'-GGTGGAATTCCCACCATGTACAGGATGCAAC-3' (SEQ ID NO:161)

3' side DNA primer (a sequence containing XhoI site on pFUSE-CHIg-hG1 (Invitrogen Co.) and a partial sequence encoding the C-terminal region of the variable region of the H-chain of 002-A07): 5'-TGCACTCGAGACGGTGACCAGTGTACCTTGGCCCC-3' (SEQ ID NO:162)

After digestion with EcoRI and XhoI, the amplified DNA was inserted into the EcoRI-XhoI site of pFUSE-CHIg-hG1 to yield a converted-to-IgG1 H-chain expression plasmid (b). To prepare a human IgG1-type anti-CD81 antibody protein, the plasmids (a) and (b) were transiently introduced into CHO—S cells, and the cells were subjected to suspension culture. The culture supernatant was recovered, and the human IgG1-type anti-CD81 antibody was purified using a Protein A column. The nucleotide and amino acid sequences of L- and H-chains of the antibody are shown in the Sequence Listing.

L-Chain:
Nucleotide sequence: SEQ ID NO:163
Amino acid sequence: SEQ ID NO:164
H-Chain:
Nucleotide sequence: SEQ ID NO:165
Amino acid sequence: SEQ ID NO:166

Experimental Example 14

Binding Activity of Human IgG1-Type Anti-CD81 Antibody on Cancer Cells

Binding of a human IgG1-type anti-CD81 antibody to Jurkat E6.1 cells (Cat No. 88042803) derived from a human acute lymphatic leukemia patient and Ramos (RAI) cells (Cat No. EC85030802) derived from a human Burkitt's lymphoma patient was examined in the same manner as Experimental Example 1, except that human IgG (AbD Serotec Co.) was used as a control, and that a PE (phycoerythrin)-labeled anti-human Ig antibody (Beckman Coulter Co.) was used for the staining. The results of an analysis using FACS Calibur (BD Biosciences Co.) are shown in Table 16. The numerical values in the table are geometric means for FL2 in the FACS Calibur. As a result, human IgG1-type anti-CD81 antibody was confirmed as binding to Jurkat cells and Ramos cells.

TABLE 16

Binding of human IgG1-type anti-CD81 antibody to Jurkat cells and Ramos cells

| | cell | | | | | | | |
|---|---|---|---|---|---|---|---|---|
| | Jurkat | | | | Ramos | | | |
| | Antibody (μg/mL) | | | | | | | |
| | 10 | 1 | 0.1 | 0.01 | 10 | 1 | 0.1 | 0.01 |
| control IgG | 8 | 4 | 4 | 4 | 8 | 5 | 4 | 4 |
| human IgG1-type anti-human CD81 antibody | 2310 | 930 | 144 | 32 | 2129 | 1183 | 712 | 584 |

Experimental Example 15

Cytotoxic Effect (CDC: Complement-Dependent Cytotoxicity) of Human IgG1-Type Anti-CD81 Antibody on Cancer Cells After centrifugation at 4,000 rpm (4° C., 3 minutes), Jurkat cells and Ramos cells were recovered and suspended in CDC assay buffer (an RPMI1640 medium containing 20 mM Hepes and 0.1% bovine serum albumin). Viable cells were counted using Trypan Blue (GIBCO Co.); the cells were suspended in the CDC assay buffer to obtain a cell density of $10^6$ cells/mL. The cells suspended were dispended to a 96-well cell culture plate at 50 μL per well; the antibody shown in Table 17 was added at 50 μL per well, and the plate was incubated at 37° C. for 30 minutes. A dry rabbit complement (CEDARRLANE Co.) was rehydrated with sterile distilled water and diluted 10 fold with the CDC assay buffer, after which 50 μL of the dilution was added to each well, and the plate was incubated at 37° C. for 2 more hours. A 100 μL aliquot of the culture supernatant was mixed with 100 μL of the reaction liquid in an LDH assay kit (Cat. No. 744934001, Roche Co.), and they were reacted at room temperature for 30 minutes, after which absorbance at 490 nm wavelength was measured using a plate reader. CDC activity was calculated as the percent ratio to the LDH activity value obtained when the cells were completely killed by Triton X-100 treatment. As a result, the complement-dependent cytotoxic activity of the human IgG1-type anti-CD81 antibody on Jurkat cells and Ramos cells was confirmed.

TABLE 17

Cytotoxic effects of human IgG1-type anti-CD81 antibody on Jurkat cells

| | cell Jurkat antibody (ng/mL) | | | | | |
|---|---|---|---|---|---|---|
| | 10000 | 1000 | 100 | 10 | 1 | 0.1 |
| control IgG | 5.8 | 4.6 | 4.1 | 4.6 | 3.7 | 4.7 |
| human IgG1-type anti-human CD81 antibody | 84.9 | 73.3 | 42.6 | 6.4 | 5.9 | 6.3 |

TABLE 18

Cytotoxic effects of human IgG1-type anti-CD81 antibody on Ramos cells

| | cell Ramos antibody (ng/mL) | | | | | |
|---|---|---|---|---|---|---|
| | 10000 | 1000 | 100 | 10 | 1 | 0.1 |
| control IgG | 0.2 | 1.7 | 1.0 | 1.9 | 0.4 | −1.1 |
| human IgG1-type anti-human CD81 antibody | 71.7 | 71.4 | 69.4 | 49.3 | 26.0 | 9.9 |

INDUSTRIAL APPLICABILITY

The anti-human CD81 antibody of the present invention is useful for preventing, improving or treating inflammatory bowel diseases (IBD), diseases associated with T cell migration such as multiple sclerosis and psoriasis, or hematological cancer.

The invention claimed is:

1. An isolated anti-human CD81 antibody that binds to a peptide region consisting of the amino acid sequence of residues 80 to 175 in the amino acid sequence of SEQ ID NO: 22, wherein the binding affinity of the antibody to at least one human CD81 variant selected from the group consisting of the following (1) to (13) is less than 40% of that to the human CD81 polypeptide comprising the amino acid sequence of SEQ ID NO:22;

(1) CD81 variant comprising the amino acid sequence of SEQ ID NO:22 except that tyrosine at residue 127 is substituted with phenylalanine or tryptophan;

(2) CD81 variant comprising the amino acid sequence of SEQ ID NO:22 except that alanine at residue 130 is substituted with threonine or valine;

(3) CD81 variant comprising the amino acid sequence of SEQ ID NO:22 except that valine at residue 135 is substituted with alanine or leucine;

(4) CD81 variant comprising the amino acid sequence of SEQ ID NO:22 except that aspartic acid at residue 137 is substituted with alanine or glutamic acid;

(5) CD81 variant comprising the amino acid sequence of SEQ ID NO:22 except that alanine at residue 143 is substituted with threonine or valine;

(6) CD81 variant comprising the amino acid sequence of SEQ ID NO:22 except that histidine at residue 151 is substituted with alanine or arginine;

(7) CD81 variant comprising the amino acid sequence of SEQ ID NO:22 except that leucine at residue 154 is substituted with alanine or isoleucine;

(8) CD81 variant comprising the amino acid sequence of SEQ ID NO:22 except that glycine at residue 158 is substituted with alanine or serine;

(9) CD81 variant comprising the amino acid sequence of SEQ ID NO:22 except that alanine at residue 164 is substituted with threonine or valine;

(10) CD81 variant comprising the amino acid sequence of SEQ ID NO:22 except that serine at residue 168 is substituted with alanine or threonine;

(11) CD81 variant comprising the amino acid sequence of SEQ ID NO:22 except that valine at residue 169 is substituted with alanine or leucine;

(12) CD81 variant comprising the amino acid sequence of SEQ ID NO:22 except that leucine at residue 170 is substituted with alanine or isoleucine; and

(13) CD81 variant comprising the amino acid sequence of SEQ ID NO:22 except that asparagine at residue 172 is substituted with alanine or glutamine.

2. The antibody of claim 1, wherein the binding affinity of the antibody to each of the above-identified human CD81 variants (9) and (11) is less than 40% of that to the human CD81 polypeptide comprising the amino acid sequence of SEQ ID NO:22.

3. An isolated antibody that binds to the human CD81 polypeptide comprising the amino acid sequence of SEQ ID NO:22, wherein binding of the antibody to the human CD81 polypeptide is competitively inhibited by the antibody of claim 1.

4. An isolated antibody that binds to the human CD81 polypeptide comprising the amino acid sequence of SEQ ID NO:22, wherein binding of the antibody to the human CD81 polypeptide is competitively inhibited by the antibody of claim 1, and wherein the antibody has a suppressive effect on T cell migration.

5. An isolated anti-human CD81 antibody, which comprises all 6 complementary determining regions (CDRs) described in any one of the following groups 1 to 24:

Group 1

(a-1) a CDR comprising the amino acid sequence of SEQ ID NO:1,
(b-1) a CDR comprising the amino acid sequence of SEQ ID NO:2,
(c-1) a CDR comprising the amino acid sequence of SEQ ID NO:3,
(d-1) a CDR comprising the amino acid sequence of SEQ ID NO:4,
(e-1) a CDR comprising the amino acid sequence of SEQ ID NO:5, and
(f-1) a CDR comprising the amino acid sequence of SEQ ID NO:6

Group 2

(a-2) a CDR comprising the amino acid sequence of SEQ ID NO:1,
(b-2) a CDR comprising the amino acid sequence of SEQ ID NO:2,
(c-2) a CDR comprising the amino acid sequence of SEQ ID NO:37,
(d-2) a CDR comprising the amino acid sequence of SEQ ID NO:4,
(e-2) a CDR comprising the amino acid sequence of SEQ ID NO:5, and
(f-2) a CDR comprising the amino acid sequence of SEQ ID NO:6

Group 3

(a-3) a CDR comprising the amino acid sequence of SEQ ID NO:1,
(b-3) a CDR comprising the amino acid sequence of SEQ ID NO:2,
(c-3) a CDR comprising the amino acid sequence of SEQ ID NO:40,
(d-3) a CDR comprising the amino acid sequence of SEQ ID NO:4,
(e-3) a CDR comprising the amino acid sequence of SEQ ID NO:5, and
(f-3) a CDR comprising the amino acid sequence of SEQ ID NO:6

Group 4

(a-4) a CDR comprising the amino acid sequence of SEQ ID NO:1,
(b-4) a CDR comprising the amino acid sequence of SEQ ID NO:2,
(c-4) a CDR comprising the amino acid sequence of SEQ ID NO:43,
(d-4) a CDR comprising the amino acid sequence of SEQ ID NO:4,
(e-4) a CDR comprising the amino acid sequence of SEQ ID NO:5, and
(f-4) a CDR comprising the amino acid sequence of SEQ ID NO:6

Group 5

(a-5) a CDR comprising the amino acid sequence of SEQ ID NO:1,
(b-5) a CDR comprising the amino acid sequence of SEQ ID NO:2,
(c-5) a CDR comprising the amino acid sequence of SEQ ID NO:46,
(d-5) a CDR comprising the amino acid sequence of SEQ ID NO:4,
(e-5) a CDR comprising the amino acid sequence of SEQ ID NO:5, and
(t-5) a CDR comprising the amino acid sequence of SEQ ID NO:6

Group 6

(a-6) a CDR comprising the amino acid sequence of SEQ ID NO:1,
(b-6) a CDR comprising the amino acid sequence of SEQ ID NO:2,
(c-6) a CDR comprising the amino acid sequence of SEQ ID NO:49,
(d-6) a CDR comprising the amino acid sequence of SEQ ID NO:4,
(e-6) a CDR comprising the amino acid sequence of SEQ ID NO:5, and
(f-6) a CDR comprising the amino acid sequence of SEQ ID NO:6

Group 7

(a-7) a CDR comprising the amino acid sequence of SEQ ID NO:1,
(b-7) a CDR comprising the amino acid sequence of SEQ ID NO:2,
(c-7) a CDR comprising the amino acid sequence of SEQ ID NO:52,
(d-7) a CDR comprising the amino acid sequence of SEQ ID NO:4,
(e-7) a CDR comprising the amino acid sequence of SEQ ID NO:5, and
(f-7) a CDR comprising the amino acid sequence of SEQ ID NO:6

Group 8

(a-8) a CDR comprising the amino acid sequence of SEQ ID NO:1,
(b-8) a CDR comprising the amino acid sequence of SEQ ID NO:2,
(c-8) a CDR comprising the amino acid sequence of SEQ ID NO:43,
(d-8) a CDR comprising the amino acid sequence of SEQ ID NO:4,
(e-8) a CDR comprising the amino acid sequence of SEQ ID NO:5, and
(f-8) a CDR comprising the amino acid sequence of SEQ ID NO:55

Group 9

(a-9) a CDR comprising the amino acid sequence of SEQ ID NO:60,
(b-9) a CDR comprising the amino acid sequence of SEQ ID NO:2,
(c-9) a CDR comprising the amino acid sequence of SEQ ID NO:3,
(d-9) a CDR comprising the amino acid sequence of SEQ ID NO:4,
(e-9) a CDR comprising the amino acid sequence of SEQ ID NO:5, and
(f-9) a CDR comprising the amino acid sequence of SEQ ID NO:61

Group 10

(a-10) a CDR comprising the amino acid sequence of SEQ ID NO:1,
(b-10) a CDR comprising the amino acid sequence of SEQ ID NO:2,
(c-10) a CDR comprising the amino acid sequence of SEQ ID NO:66,
(d-10) a CDR comprising the amino acid sequence of SEQ ID NO:4, (e-10) a CDR comprising the amino acid sequence of SEQ ID NO:5, and (f-10) a CDR comprising the amino acid sequence of SEQ ID NO:6

Group 11

(a-11) a CDR comprising the amino acid sequence of SEQ ID NO:1, (b-11) a CDR comprising the amino acid sequence of SEQ ID NO:2, (c-11) a CDR comprising the amino acid sequence of SEQ ID NO:3, (d-11) a CDR comprising the amino acid sequence of SEQ ID NO:4, (e-11) a CDR comprising the amino acid sequence of SEQ ID NO:69, and (f-11) a CDR comprising the amino acid sequence of SEQ ID NO:70

Group 12

(a-12) a CDR comprising the amino acid sequence of SEQ ID NO:60, (b-12) a CDR comprising the amino acid sequence of SEQ ID NO:2, (c-12) a CDR comprising the amino acid sequence of SEQ ID NO:66, (d-12) a CDR comprising the amino acid sequence of SEQ ID NO:4, (e-12) a CDR comprising the amino acid sequence of SEQ ID NO:5, and (f-12) a CDR comprising the amino acid sequence of SEQ ID NO:6

Group 13

(a-13) a CDR comprising the amino acid sequence of SEQ ID NO:1, (b-13) a CDR comprising the amino acid sequence of SEQ ID NO:2, (c-13) a CDR comprising the amino acid sequence of SEQ ID NO:3, (d-13) a CDR comprising the amino acid sequence of SEQ ID NO:77, (e-13) a CDR comprising the amino acid sequence of SEQ ID NO:5, and (f-13) a CDR comprising the amino acid sequence of SEQ ID NO:6

Group 14

(a-14) a CDR comprising the amino acid sequence of SEQ ID NO:80, (b-14) a CDR comprising the amino acid sequence of SEQ ID NO:2, (c-14) a CDR comprising the amino acid sequence of SEQ ID NO:3, (d-14) a CDR comprising the amino acid sequence of SEQ ID NO:4, (e-14) a CDR comprising the amino acid sequence of SEQ ID NO:81, and (f-14) a CDR comprising the amino acid sequence of SEQ ID NO:6

Group 15

(a-15) a CDR comprising the amino acid sequence of SEQ ID NO:1, (b-15) a CDR comprising the amino acid sequence of SEQ ID NO:2, (c-15) a CDR comprising the amino acid sequence of SEQ ID NO:66, (d-15) a CDR comprising the amino acid sequence of SEQ ID NO:4, (e-15) a CDR comprising the amino acid sequence of SEQ ID NO:5, and (f-15) a CDR comprising the amino acid sequence of SEQ ID NO:6

Group 16

(a-16) a CDR comprising the amino acid sequence of SEQ ID NO:1, (b-16) a CDR comprising the amino acid sequence of SEQ ID NO:2, (c-16) a CDR comprising the amino acid sequence of SEQ ID NO:90, (d-16) a CDR comprising the amino acid sequence of SEQ ID NO:4, (e-16) a CDR comprising the amino acid sequence of SEQ ID NO:5, and (f-16) a CDR comprising the amino acid sequence of SEQ ID NO:6

Group 17

(a-17) a CDR comprising the amino acid sequence of SEQ ID NO:1, (b-17) a CDR comprising the amino acid sequence of SEQ ID NO:2, (c-17) a CDR comprising the amino acid sequence of SEQ ID NO:52, (d-17) a CDR comprising the amino acid sequence of SEQ ID NO:4, (e-17) a CDR comprising the amino acid sequence of SEQ ID NO:5, and (f-17) a CDR comprising the amino acid sequence of SEQ ID NO:93

Group 18

(a-18) a CDR comprising the amino acid sequence of SEQ ID NO:98, (b-18) a CDR comprising the amino acid sequence of SEQ ID NO:2, (c-18) a CDR comprising the amino acid sequence of SEQ ID NO:3, (d-18) a CDR comprising the amino acid sequence of SEQ ID NO:4, (e-18) a CDR comprising the amino acid sequence of SEQ ID NO:5, and (f-18) a CDR comprising the amino acid sequence of SEQ ID NO:99

Group 19

(a-19) a CDR comprising the amino acid sequence of SEQ ID NO:60, (b-19) a CDR comprising the amino acid sequence of SEQ ID NO:2, (c-19) a CDR comprising the amino acid sequence of SEQ ID NO:3, (d-19) a CDR comprising the amino acid sequence of SEQ ID NO:4, (e-19) a CDR comprising the amino acid sequence of SEQ ID NO:5, and (f-19) a CDR comprising the amino acid sequence of SEQ ID NO:99

Group 20

(a-20) a CDR comprising the amino acid sequence of SEQ ID NO:1, (b-20) a CDR comprising the amino acid sequence of SEQ ID NO:2, (c-20) a CDR comprising the amino acid sequence of SEQ ID NO:90, (d-20) a CDR comprising the amino acid sequence of SEQ ID NO:4, (e-20) a CDR comprising the amino acid sequence of SEQ ID NO:5, and (f-20) a CDR comprising the amino acid sequence of SEQ ID NO:6

Group 21

(a-21) a CDR comprising the amino acid sequence of SEQ ID NO:1, (b-21) a CDR comprising the amino acid sequence of SEQ ID NO:2, (c-21) a CDR comprising the amino acid sequence of SEQ ID NO:3, (d-21) a CDR comprising the amino acid sequence of SEQ ID NO:4, (e-21) a CDR comprising the amino acid sequence of SEQ ID NO:5, and (f-21) a CDR comprising the amino acid sequence of SEQ ID NO:55

Group 22

(a-22) a CDR comprising the amino acid sequence of SEQ ID NO:1, (b-22) a CDR comprising the amino acid sequence of SEQ ID NO:2, (c-22) a CDR comprising the amino acid sequence of SEQ ID NO:66, (d-22) a CDR comprising the amino acid sequence of SEQ ID NO:110, (e-22) a CDR comprising the amino acid sequence of SEQ ID NO:5, and (f-22) a CDR comprising the amino acid sequence of SEQ ID NO:6

Group 23

(a-23) a CDR comprising the amino acid sequence of SEQ ID NO:1, (b-23) a CDR comprising the amino acid sequence of SEQ ID NO:2, (c-23) a CDR comprising the amino acid sequence of SEQ ID NO:3, (d-23) a CDR comprising the amino acid sequence of SEQ ID NO:4, (e-23) a CDR comprising the amino acid sequence of SEQ ID NO:5, and (f-23) a CDR comprising the amino acid sequence of SEQ ID NO:115

Group 24

(a-24) a CDR comprising the amino acid sequence of SEQ ID NO:1, (b-24) a CDR comprising the amino acid sequence of SEQ ID NO:2, (c-24) a CDR comprising the amino acid sequence of SEQ ID NO:90, (d-24) a CDR comprising the amino acid sequence of SEQ ID NO:4, (e-24) a CDR comprising the amino acid sequence of SEQ ID NO:120, and (f-24) a CDR comprising the amino acid sequence of SEQ ID NO:6.

6. The antibody of claim 5, which comprises the combination of the light chain variable region and the heavy chain variable region described in any one of the following groups 25 to 48:

Group 25

(g-1) a light chain variable region comprising the above-identified CDRs (a-1) to (c-1); and (h-1) a heavy chain variable region comprising the above-identified CDRs (d-1) to (f-1), Group 26

(g-2) a light chain variable region comprising the above-identified CDRs (a-2) to (c-2); and (h-2) a heavy chain variable region comprising the above-identified CDRs (d-2) to (f-2), Group 27

(g-3) a light chain variable region comprising the above-identified CDRs (a-3) to (c-3); and (h-3) a heavy chain variable region comprising the above-identified CDRs (d-3) to (f-3), Group 28

(g-4) a light chain variable region comprising the above-identified CDRs (a-4) to (c-4); and (h-4) a heavy chain variable region comprising the above-identified CDRs (d-4) to (f-4), Group 29

(g-5) a light chain variable region comprising the above-identified CDRs (a-5) to (c-5); and (h-5) a heavy chain variable region comprising the above-identified CDRs (d-5) to (f-5), Group 30

(g-6) a light chain variable region comprising the above-identified CDRs (a-6) to (c-6); and (h-6) a heavy chain variable region comprising the above-identified CDRs (d-6) to (f-6), Group 31

(g-7) a light chain variable region comprising the above-identified CDRs (a-7) to (c-7); and (h-7) a heavy chain variable region comprising the above-identified CDRs (d-7) to (f-7), Group 32

(g-8) a light chain variable region comprising the above-identified CDRs (a-8) to (c-8); and (h-8) a heavy chain variable region comprising the above-identified CDRs (d-8) to (f-8), Group 33

(g-9) a light chain variable region comprising the above-identified CDRs (a-9) to (c-9); and (h-9) a heavy chain variable region comprising the above-identified CDRs (d-9) to (f-9), Group 34

(g-10) a light chain variable region comprising the above-identified CDRs (a-10) to (c-10); and (h-10) a heavy chain variable region comprising the above-identified CDRs (d-10) to (f-10), Group 35

(g-11) a light chain variable region comprising the above-identified CDRs (a-11) to (c-11); and (h-11) a heavy chain variable region comprising the above-identified CDRs (d-11) to (f-11), Group 36

(g-12) a light chain variable region comprising the above-identified CDRs (a-12) to (c-12); and (h-12) a heavy chain variable region comprising the above-identified CDRs (d-12) to (f-12), Group 37

(g-13) a light chain variable region comprising the above-identified CDRs (a-13) to (c-13); and (h-13) a heavy chain variable region comprising the above-identified CDRs (d-13) to (f-13), Group 38

(g-14) a light chain variable region comprising the above-identified CDRs (a-14) to (c-14); and (h-14) a heavy chain variable region comprising the above-identified CDRs (d-14) to (f-14), Group 39

(g-15) a light chain variable region comprising the above-identified CDRs (a-15) to (c-15); and (h-15) a heavy chain variable region comprising the above-identified CDRs (d-15) to (f-15), Group 40

(g-16) a light chain variable region comprising the above-identified CDRs (a-16) to (c-16); and (h-16) a heavy chain variable region comprising the above-identified CDRs (d-16) to (f-16), Group 41

(g-17) a light chain variable region comprising the above-identified CDRs (a-17) to (c-17); and (h-17) a heavy chain variable region comprising the above-identified CDRs (d-17) to (f-17), Group 42

(g-18) a light chain variable region comprising the above-identified CDRs (a-18) to (c-18); and (h-18) a heavy chain variable region comprising the above-identified CDRs (d-18) to (f-18), Group 43

(g-19) a light chain variable region comprising the above-identified CDRs (a-19) to (c-19); and (h-19) a heavy chain variable region comprising the above-identified CDRs (d-19) to (f-19), Group 44

(g-20) a light chain variable region comprising the above-identified CDRs (a-20) to (c-20); and (h-20) a heavy chain variable region comprising the above-identified CDRs (d-20) to (f-20), Group 45

(g-21) a light chain variable region comprising the above-identified CDRs (a-21) to (c-21); and (h-21) a heavy chain variable region comprising the above-identified CDRs (d-21) to (f-21), Group 46

(g-22) a light chain variable region comprising the above-identified CDRs (a-22) to (c-22); and (h-22) a heavy chain variable region comprising the above-identified CDRs (d-22) to (f-22), Group 47

(g-23) a light chain variable region comprising the above-identified CDRs (a-23) to (c-23); and (h-23) a heavy chain variable region comprising the above-identified CDRs (d-23) to (f-23), Group 48

(g-24) a light chain variable region comprising the above-identified CDRs (a-24) to (c-24); and (h-24) a heavy chain variable region comprising the above-identified CDRs (d-24) to (f-24).

7. The antibody of claim 6, which comprises the combination of the light chain variable region and the heavy chain variable region described in any one of the following groups 49 to 72:

Group 49

(i-1) a light chain variable region comprising the amino acid sequence of SEQ ID NO:8; and (j-1) a heavy chain variable region comprising amino acid sequence of SEQ ID NO:10, Group 50

(i-2) a light chain variable region comprising the amino acid sequence of SEQ ID NO:38; and (j-2) a heavy chain variable region comprising amino acid sequence of SEQ ID NO:10, Group 51

(i-3) a light chain variable region comprising the amino acid sequence of SEQ ID NO:41; and (j-3) a heavy chain variable region comprising amino acid sequence of SEQ ID NO:10, Group 52

(i-4) a light chain variable region comprising the amino acid sequence of SEQ ID NO:44; and (j-4) a heavy chain variable region comprising amino acid sequence of SEQ ID NO:10, Group 53

(i-5) a light chain variable region comprising the amino acid sequence of SEQ ID NO:47; and (j-5) a heavy chain variable region comprising amino acid sequence of SEQ ID NO:10, Group 54

(i-6) a light chain variable region comprising amino acid sequence of SEQ ID NO:50; and (j-6) a heavy chain variable region comprising amino acid sequence of SEQ ID NO:10, Group 55

(i-7) a light chain variable region comprising amino acid sequence of SEQ ID NO:53; and (j-7) a heavy chain variable region comprising amino acid sequence of SEQ ID NO:10, Group 56

(i-8) a light chain variable region comprising amino acid sequence of SEQ ID NO:56; and (j-8) a heavy chain variable region comprising amino acid sequence of SEQ ID NO:57, Group 57

(i-9) a light chain variable region comprising amino acid sequence of SEQ ID NO:62; and (j-9) a heavy chain variable region comprising amino acid sequence of SEQ ID NO:63, Group 58

(i-10) a light chain variable region comprising amino acid sequence of SEQ ID NO:67; and (j-10) a heavy chain variable region comprising amino acid sequence of SEQ ID NO:10, Group 59

(i-11) a light chain variable region comprising amino acid sequence of SEQ ID NO:71; and (j-11) a heavy chain variable region comprising amino acid sequence of SEQ ID NO:72, Group 60

(i-12) a light chain variable region comprising amino acid sequence of SEQ ID NO:75; and (j-12) a heavy chain variable region comprising amino acid sequence of SEQ ID NO:10, Group 61

(i-13) a light chain variable region comprising amino acid sequence of SEQ ID NO:8; and (j-13) a heavy chain variable region comprising amino acid sequence of SEQ ID NO:78, Group 62

(i-14) a light chain variable region comprising amino acid sequence of SEQ ID NO:82; and (j-14) a heavy chain variable region comprising amino acid sequence of SEQ ID NO:83, Group 63

(i-15) a light chain variable region comprising amino acid sequence of SEQ ID NO:86; and (j-15) a heavy chain variable region comprising amino acid sequence of SEQ ID NO:87, Group 64

(i-16) a light chain variable region comprising amino acid sequence of SEQ ID NO:91; and (j-16) a heavy chain variable region comprising amino acid sequence of SEQ ID NO:10, Group 65

(i-17) a light chain variable region comprising amino acid sequence of SEQ ID NO:94; and (j-17) a heavy chain variable region comprising amino acid sequence of SEQ ID NO:95, Group 66

(i-18) a light chain variable region comprising amino acid sequence of SEQ ID NO:100; and (j-18) a heavy chain variable region comprising amino acid sequence of SEQ ID NO:101, Group 67

(i-19) a light chain variable region comprising amino acid sequence of SEQ ID NO:104; and (j-19) a heavy chain variable region comprising amino acid sequence of SEQ ID NO:101, Group 68

(i-20) a light chain variable region comprising amino acid sequence of SEQ ID NO:106; and (j-20) a heavy chain variable region comprising amino acid sequence of SEQ ID NO:10, Group 69

(i-21) a light chain variable region comprising amino acid sequence of SEQ ID NO:108; and (j-21) a heavy chain variable region comprising amino acid sequence of SEQ ID NO:57, Group 70

(i-22) a light chain variable region comprising amino acid sequence of SEQ ID NO:111; and (j-22) a heavy chain variable region comprising amino acid sequence of SEQ ID NO:112, Group 71

(i-23) a light chain variable region comprising amino acid sequence of SEQ ID NO:116; and (j-23) a heavy chain variable region comprising amino acid sequence of SEQ ID NO:117, Group 72

(i-24) a light chain variable region comprising amino acid sequence of SEQ ID NO:121; and (j-24) a heavy chain variable region comprising amino acid sequence of SEQ ID NO:122.

8. The antibody of claim 6, which comprises the combination of the light chain and the heavy chain described in any one of the following groups 73 to 96:

Group 73

(k-1) a light chain comprising the amino acid sequence of SEQ ID NO:26; and (l-1) a heavy chain comprising the amino acid sequence of SEQ ID NO:28, Group 74

(k-2) a light chain comprising the amino acid sequence of SEQ ID NO:39; and (l-2) a heavy chain comprising the amino acid sequence of SEQ ID NO:28, Group 75

(k-3) a light chain comprising the amino acid sequence of SEQ ID NO:42; and (l-3) a heavy chain comprising the amino acid sequence of SEQ ID NO:28, Group 76

(k-4) a light chain comprising the amino acid sequence of SEQ ID NO:45; and (l-4) a heavy chain comprising the amino acid sequence of SEQ ID NO:28, Group 77

(k-5) a light chain comprising the amino acid sequence of SEQ ID NO:48; and (l-5) a heavy chain comprising the amino acid sequence of SEQ ID NO:28, Group 78

(k-6) a light chain comprising the amino acid sequence of SEQ ID NO:51; and (l-6) a heavy chain comprising the amino acid sequence of SEQ ID NO:28, Group 79

(k-7) a light chain comprising the amino acid sequence of SEQ ID NO:54; and (l-7) a heavy chain comprising the amino acid sequence of SEQ ID NO:28, Group 80

(k-8) a light chain comprising the amino acid sequence of SEQ ID NO:58; and (l-8) a heavy chain comprising the amino acid sequence of SEQ ID NO:59, Group 81

(k-9) a light chain comprising the amino acid sequence of SEQ ID NO:64; and (l-9) a heavy chain comprising the amino acid sequence of SEQ ID NO:65, Group 82

(k-10) a light chain comprising the amino acid sequence of SEQ ID NO:68; and (l-10) a heavy chain comprising the amino acid sequence of SEQ ID NO: 28, Group 83

(k-11) a light chain comprising the amino acid sequence of SEQ ID NO:73; and (l-11) a heavy chain comprising the amino acid sequence of SEQ ID NO: 74, Group 84

(k-12) a light chain comprising the amino acid sequence of SEQ ID NO:76; and (l-12) a heavy chain comprising the amino acid sequence of SEQ ID NO: 28, Group 85

(k-13) a light chain comprising the amino acid sequence of SEQ ID NO:26; and (l-13) a heavy chain comprising the amino acid sequence of SEQ ID NO: 79, Group 86

(k-14) a light chain comprising the amino acid sequence of SEQ ID NO:84; and (l-14) a heavy chain comprising the amino acid sequence of SEQ ID NO: 85, Group 87

(k-15) a light chain comprising the amino acid sequence of SEQ ID NO:88; and (l-15) a heavy chain comprising the amino acid sequence of SEQ ID NO: 89, Group 88

(k-16) a light chain comprising the amino acid sequence of SEQ ID NO:92; and (l-16) a heavy chain comprising the amino acid sequence of SEQ ID NO: 28, Group 89

(k-17) a light chain comprising the amino acid sequence of SEQ ID NO:96; and (l-17) a heavy chain comprising the amino acid sequence of SEQ ID NO: 97, Group 90

(k-18) a light chain comprising the amino acid sequence of SEQ ID NO: 102; and (l-18) a heavy chain comprising the amino acid sequence of SEQ ID NO: 103, Group 91

(k-19) a light chain comprising the amino acid sequence of SEQ ID NO: 105; and (l-19) a heavy chain comprising the amino acid sequence of SEQ ID NO: 103, Group 92
(k-20) a light chain comprising the amino acid sequence of SEQ ID NO: 107; and
(l-20) a heavy chain comprising the amino acid sequence of SEQ ID NO: 28, Group 93
(k-21) a light chain comprising the amino acid sequence of SEQ ID NO: 109; and
(l-21) a heavy chain comprising the amino acid sequence of SEQ ID NO: 59, Group 94
(k-22) a light chain comprising the amino acid sequence of SEQ ID NO: 113; and
(l-22) a heavy chain comprising the amino acid sequence of SEQ ID NO: 114, Group 95
(k-23) a light chain comprising the amino acid sequence of SEQ ID NO: 118; and
(l-23) a heavy chain comprising the amino acid sequence of SEQ ID NO: 119, Group 96
(k-24) a light chain comprising the amino acid sequence of SEQ ID NO: 123; and
(l-24) a heavy chain comprising the amino acid sequence of SEQ ID NO: 124.

9. An isolated antibody binding to the human CD81 polypeptide comprising the amino acid sequence of SEQ ID NO:22, wherein biding of the antibody to the human CD81 polypeptide is competitively inhibited by the antibody of claim 5.

10. The antibody of claim 9, which has a suppressive effect on T cell migration.

11. An isolated anti-human CD81 antibody comprising:
(a-25) a complementarity determining region (CDR) comprising the amino acid sequence SEQ ID NO:11;
(b-25) a CDR comprising the amino acid sequence of SEQ ID NO:12;
(c-25) a CDR comprising the amino acid sequence of SEQ ID NO:13;
(d-25) a CDR comprising the amino acid sequence of SEQ ID NO:14;
(e-25) a CDR comprising the amino acid sequence of SEQ ID NO:15; and
(f-25) a CDR comprising the amino acid sequence of SEQ ID NO:16.

12. The antibody of claim 11, which comprises:
(g-25) a light chain variable region comprising the above-identified CDRs (a-25) to (c-25); and
(h-25) a heavy chain variable region comprising the above-identified CDRs (d-25) to (f-25).

13. The antibody of claim 12, which comprises:
(i-25) a light chain variable region comprising the amino acid sequence of SEQ ID NO:18; and
(j-25) a heavy chain variable region comprising the amino acid sequence of SEQ ID NO:20.

14. The antibody of claim 12, which comprises:
(k-25) a light chain comprising the amino acid sequence of SEQ ID NO:30; and
(l-25) a heavy chain comprising the amino acid sequence of SEQ ID NO:32.

15. An isolated antibody binding to the human CD81 polypeptide comprising the amino acid sequence of SEQ ID NO:22, wherein biding of the antibody to the human CD81 polypeptide is competitively inhibited by the antibody of claim 11.

16. The antibody of claim 15, which has a suppressive effect on T cell migration.

17. The antibody of claim 1 which is a humanized or human antibody.

18. A pharmaceutical composition comprising the antibody of claim 1.

* * * * *

UNITED STATES PATENT AND TRADEMARK OFFICE

CERTIFICATE OF CORRECTION

PATENT NO. : 8,440,797 B2
APPLICATION NO. : 13/311124
DATED : May 14, 2013
INVENTOR(S) : Watanabe et al.

It is certified that error appears in the above-identified patent and that said Letters Patent is hereby corrected as shown below:

IN THE CLAIMS

Claim 5, column 228, line 5, "(t-5)" should read "(f-5)"

Claim 7, column 233, lines 53, 58, and 63, "comprising amino acid" should read "comprising the amino acid"

Claim 7, column 234, lines 1, 6, 9, 11, 14, 16, 19, 21, 24, 26, 29, 31, 34, 36, 39, 41, 44, 46, 49, 51, 54, 56, 59, 61, 64, and 66, "comprising amino acid" should read "comprising the amino acid"

Claim 7, column 235, lines 2, 4, 7, 9, 12, 15, 18, 20, 23, 25, 28, 30, 33, and 35, "comprising amino acid" should read "comprising the amino acid"

Claim 9, column 237, line 28, "biding" should read "binding"

Claim 11, column 237, line 35, "the amino acid sequence SEQ ID NO: 11;" should read "the amino acid sequence of SEQ ID NO: 11;"

Claim 15, column 238, line 27, "biding" should read "binding"

Signed and Sealed this
Twenty-second Day of October, 2013

Teresa Stanek Rea
*Deputy Director of the United States Patent and Trademark Office*